US012760037B2

(12) United States Patent
Cernaka et al.

(10) Patent No.: US 12,760,037 B2
(45) Date of Patent: Oct. 13, 2026

(54) PLASMA KALLIKREIN INHIBITORS

(71) Applicant: Merck Sharp & Dohme LLC, Rahway, NJ (US)

(72) Inventors: Natalija Cernaka, Redwood City, CA (US); Anthony K. Ogawa, San Mateo, CA (US); Alan C. Cheng, San Francisco, CA (US); Jianming Bao, Princeton, NJ (US); Phillip Patrick Sharp, San Francisco, CA (US); Jovan Alexander Lopez, New Haven, CT (US); Dong Xiao, Warren, NJ (US); Haiqun Tang, Belle Mead, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 405 days.

(21) Appl. No.: 18/550,332

(22) PCT Filed: Mar. 16, 2022

(86) PCT No.: PCT/US2022/020487
§ 371 (c)(1),
(2) Date: Sep. 13, 2023

(87) PCT Pub. No.: WO2022/197761
PCT Pub. Date: Sep. 22, 2022

(65) Prior Publication Data
US 2024/0190892 A1 Jun. 13, 2024

Related U.S. Application Data

(60) Provisional application No. 63/162,915, filed on Mar. 18, 2021.

(51) Int. Cl.
*C07D 498/20* (2006.01)
*A61K 31/5386* (2006.01)
*A61K 45/06* (2006.01)
*C07D 519/00* (2006.01)

(52) U.S. Cl.
CPC ........ *C07D 498/20* (2013.01); *A61K 31/5386* (2013.01); *A61K 45/06* (2013.01); *C07D 519/00* (2013.01)

(58) Field of Classification Search
None
See application file for complete search history.

(56) References Cited

U.S. PATENT DOCUMENTS 9,957,229 B2 5/2018 Yao et al.

FOREIGN PATENT DOCUMENTS

WO 2015164308 A1 10/2015
WO 2017074833 A1 5/2017

OTHER PUBLICATIONS

Yousef. Endocrine Reviews, 2001, 22(2), 184-204 (Year: 2001).*
Abdel-Magid. ACS Medicinal Chemistry Letters, 2023, 14, 129-130 (Year: 2023).*
Chou, Ting-Chao et al., Quantitative Analysis of Dose-Effect Relationships: the Combined Effects of Multiple Drugs or Enzyme Inhibitors, Adv. Enzyme Regul., 1984, 27-55, 22.
Clermont, Allen et al., Plasma Kallikrein Mediates Retinal Vascular Dysfunction and Induces Retinal Thickening in Diabetic Rats, Diabetes, 2011, 1590-1598, 60.
Daiss, Jurgen, O. et al., Sila-venlafaxine, a Sila-Analogue of the Serotonin/Noradrenaline Reuptake Inhibitor Venlafaxine: Synthesis, Crystal Structure Analysis, and Pharmacological Characterization, Organometallics, 2006, pp. 1188-1198, vol. 25.
Kelemen, Àdàm A. et al., Spiro[pyrrolidine-3,30-oxindoles] and Their Indoline Analogues as New 5-HT6 Receptor Chemotypes, Molecules, 2017, 1-25, 22, 2221.
Schneider, Lynda et al., Critical role of kallikrein in hereditary angioedema pathogenesis: A clinical trial of ecallantide, a novel kallikrein inhibitor, J Allergy Clin Immunol, 2007, 416-422, 120(2).
(Continued)

*Primary Examiner* — Noble E Jarrell
(74) *Attorney, Agent, or Firm* — Daniel Woods; John C. Todaro

(57) ABSTRACT

The present invention provides a compound of formula I and pharmaceutical compositions comprising one or more said compounds, and methods for using said compounds for treating or preventing one or more disease states that could benefit from inhibition of plasma kallikrein, including hereditary angioedema, uveitis, posterior uveitis, wet age-related macular degeneration, diabetic macular edema, diabetic retinopathy and retinal vein occlusion. The compounds are selective inhibitors of plasma kallikrein.

I

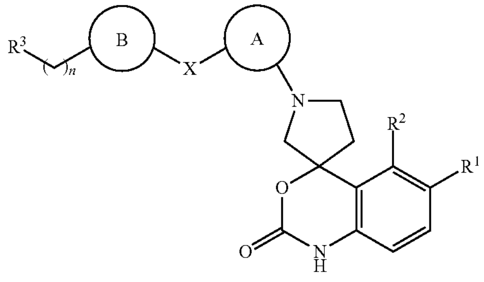

13 Claims, No Drawings

(56) References Cited

OTHER PUBLICATIONS

Showell, Graham, A. et al., (R)-Sila-venlafaxine: A selective noradrenaline reuptake inhibitor for the treatment of emesis, Bioorganic & Medicinal Chemistry Letters, 2006, pp. 2555-2558, vol. 16.

Zuraw, Bruce et al., Oral once-daily berotralstat for the prevention of hereditary angioedema attacks: A randomized, double-blind, placebo-controlled phase 3 trial, J Allergy Clin Immunol, 2021, 164-172, 148.

* cited by examiner

PLASMA KALLIKREIN INHIBITORS

CROSS REFERENCE TO RELATED APPLICATIONS

The present application is a 371 national phase application of International Application No. PCT/US2022/020487, filed Mar. 16, 2022, which claims the benefit of U.S. Provisional Application No. 63/162,915, filed Mar. 18, 2021, hereby incorporated by reference in its entirety.

BACKGROUND OF THE INVENTION

Patients presenting genetic deficiency on C1-inhibitor suffer from hereditary angioedema (HAE), a lifelong disease that results in intermittent swelling throughout the body, including the hands, feet, face, throat, genitals and gastrointestinal tract. Analysis of blisters arising from acute episodes have been shown to contain high levels of plasma kallikrein, and treatment with a protein-based reversible plasma kallikrein inhibitor, Ecallantide (Kalbitor), has been approved by the FDA for the treatment of acute attacks of HAE (Schneider, L, et al., J. Allergy Clin. Immunol., 120: p. 416 (2007)). Recently, an oral plasma kallikrein inhibitor, Berotralstat, gained FDA approval for the prevention of HAE attacks (Zuraw, B., et al., J. Allergy Clin. Immunol. (2020).

Additionally, the plasma kallikrein-kinin system is abnormally abundant in patients diagnosed with advanced diabetic macular edema (DME). Recent publications have shown that plasma kallikrein contributes to observed retinal vascular leakage and dysfunction in diabetic rodent models (A. Clermont, et al., Diabetes, 60:1590 (2011)), and that treatment with a small molecule plasma kallikrein inhibitor ameliorated the observed retinal vascular permeability and other abnormalities related to retinal blood flow.

It would be desirable in the art to develop plasma kallikrein inhibitors having utility to treat a wide range of disorders, including hereditary angioedema, diabetic macular edema and diabetic retinopathy.

SUMMARY OF THE INVENTION

The present invention relates to compounds of Formula I:

I

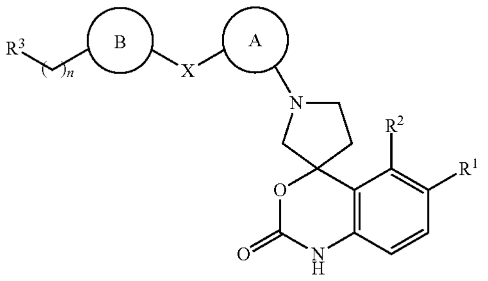

and pharmaceutically acceptable salts thereof. The compounds of Formula I are inhibitors of plasma kallikrein, and as such may be useful in the treatment, inhibition or amelioration of one or more disease states that could benefit from inhibition of plasma kallikrein, including hereditary angioedema, uveitis, posterior uveitis, wet age-related macular degeneration, diabetic macular edema, diabetic retinopathy and retinal vein occlusion. The compounds of this invention could further be used in combination with other therapeutically effective agents, including but not limited to, other drugs useful for the treatment of hereditary angioedema, uveitis, posterior uveitis, wet age-related macular degeneration, diabetic macular edema, diabetic retinopathy and retinal vein occlusion. The invention furthermore relates to processes for preparing compounds of Formula I, and pharmaceutical compositions which comprise compounds of Formula I and pharmaceutically acceptable salts thereof.

DETAILED DESCRIPTION OF THE INVENTION

The present invention relates to compounds of Formula I:

I

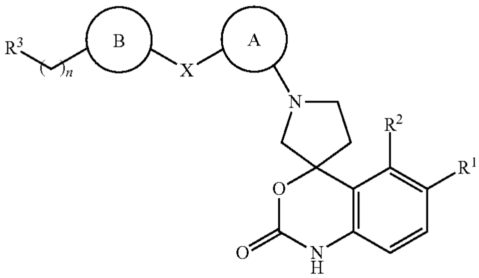

wherein X is —$CH_2$—, —NH(C═O)$CH_2$— or —(C═O)$NHCH_2$—;

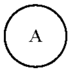 is 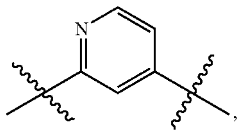,

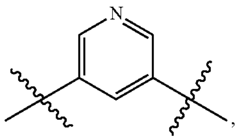, 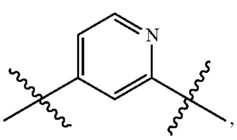,

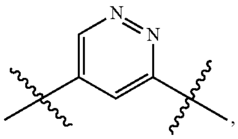, 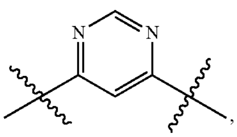,

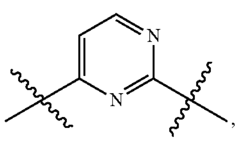, 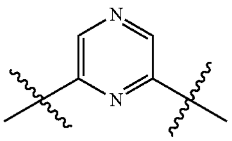 or

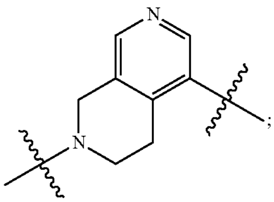;

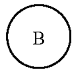

is phenyl or heteroaryl, which can be monocyclic or bicyclic, wherein said phenyl is optionally substituted with halo and said heteroaryl is optionally substituted with halo, hydroxy, $C_{1-6}$ alkyl or oxo;

$R^1$ is selected from the group consisting of hydrogen, halo, hydroxy and $C_{1-6}$ alkyl;

$R^2$ is selected from the group consisting of hydrogen, halo, hydroxy and $C_{1-6}$ alkyl;

$R^3$ is selected from the group consisting of hydrogen, heterocyclyl, which can be monocyclic or bicyclic, heteroaryl and $NR^4R^5$, wherein said heteroaryl is optionally substituted with one or two substituents independently selected from the group consisting of oxo and $C_{1-6}$ alkyl and said heterocyclyl is optionally substituted with one to three substituents independently selected from the group consisting of halo, hydroxy, cyano and $R^x$;

$R^4$ is selected from the group consisting of hydrogen, cyclopropyl and $C_{1-6}$ alkyl;

$R^5$ is selected from the group consisting of hydrogen and $C_{1-6}$ alkyl, which is optionally substituted with one to three substituents selected from the group consisting of halo, hydroxy and cyano;

$R^x$ is hydrogen or $C_{1-6}$ alkyl, which is optionally substituted with one to three substituents selected from the group consisting of halo, hydroxy and methoxy;

n is an integer from zero to two;

or a pharmaceutically acceptable salt thereof.

In an embodiment of the invention, X is $—CH_2—$. In another embodiment of the invention, X is $—NH(C{=}O)CH_2—$. In another embodiment of the invention, X is $—(C{=}O)NHCH_2—$.

The present invention also relates to compounds of Formula Ia:

Ia

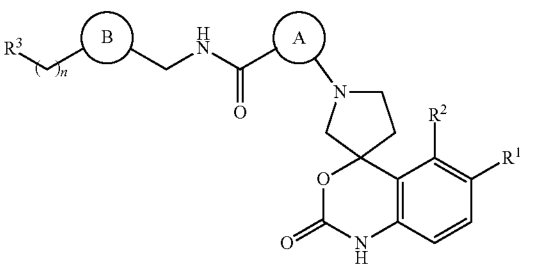

wherein 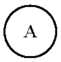 is 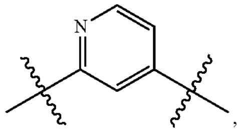,

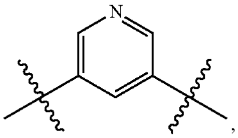, 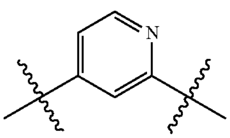,

-continued

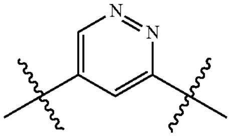, 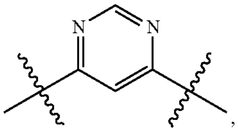,

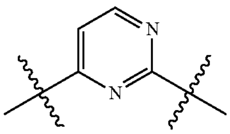, 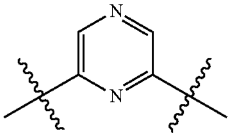 or

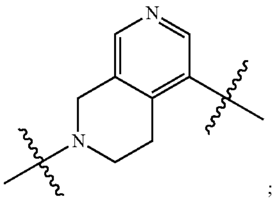; 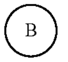 is 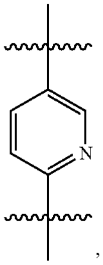,

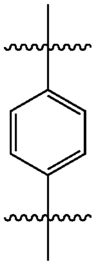, 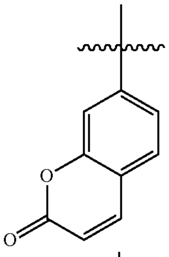, 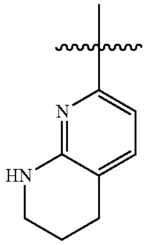 or

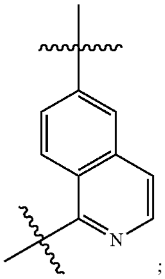;

$R^1$ is selected from the group consisting of hydrogen, halo, hydroxy and $C_{1-6}$ alkyl;

$R^2$ is selected from the group consisting of hydrogen, halo, hydroxy and $C_{1-6}$ alkyl;

$R^3$ is selected from the group consisting of hydrogen, heterocyclyl, which can be monocyclic or bicyclic, heteroaryl and $NR^4R^5$, wherein said heteroaryl is optionally substituted with one or two substituents independently selected from the group consisting of oxo and $C_{1-6}$ alkyl and said heterocyclyl is optionally substituted with one to three substituents independently selected from the group consisting of halo, hydroxy, cyano and $R^x$;

$R^4$ is selected from the group consisting of hydrogen, cyclopropyl and $C_{1-6}$ alkyl;

$R^5$ is selected from the group consisting of hydrogen and $C_{1-6}$ alkyl, which is optionally substituted with one to three substituents selected from the group consisting of halo, hydroxy and cyano;

$R^x$ is hydrogen or $C_{1-6}$ alkyl, which is optionally substituted with one to three substituents selected from the group consisting of halo, hydroxy and methoxy;

n is an integer from zero to two;

or a pharmaceutically acceptable salt thereof.

The present invention also relates to compounds of Formula 1b:

Ib

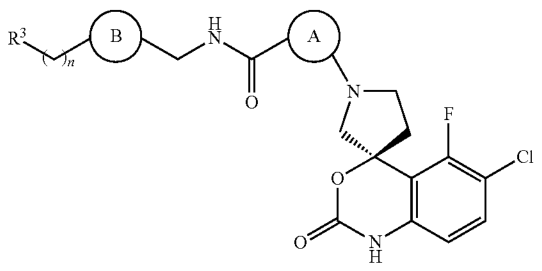

wherein A is

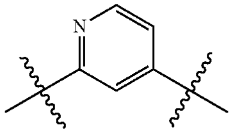

,

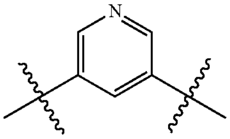

,

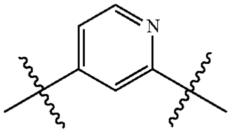

,

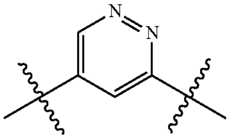

,

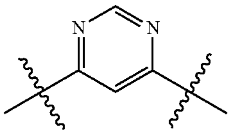

,

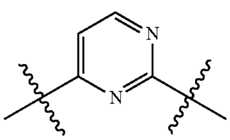

,

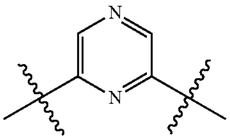

or

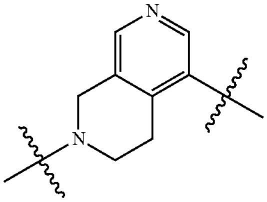

;

B is

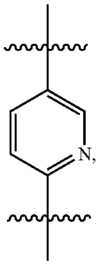

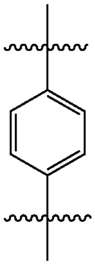

,

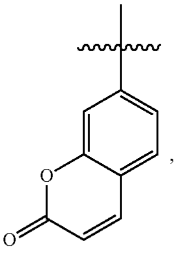

,

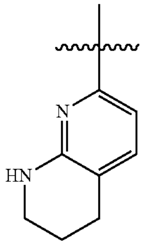

or

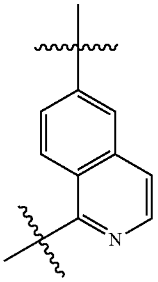

;

$R^3$ is selected from the group consisting of hydrogen, heterocyclyl, which can be monocyclic or bicyclic, heteroaryl and $NR^4R^5$, wherein said heteroaryl is optionally substituted with one or two substituents independently selected from the group consisting of oxo and $C_{1-6}$ alkyl and said heterocyclyl is optionally substituted with one to three substituents independently selected from the group consisting of halo, hydroxy, cyano and $R^x$;

$R^4$ is selected from the group consisting of hydrogen, cyclopropyl and $C_{1-6}$ alkyl;

$R^5$ is selected from the group consisting of hydrogen and $C_{1-6}$ alkyl, which is optionally substituted with one to three substituents selected from the group consisting of halo, hydroxy and cyano;

$R^x$ is hydrogen or $C_{1-6}$ alkyl, which is optionally substituted with one to three substituents selected from the group consisting of halo, hydroxy and methoxy;

n is an integer from zero to two;

or a pharmaceutically acceptable salt thereof

In an embodiment of the invention,

A is

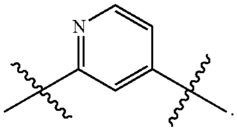

.

In another embodiment of the invention,

A is

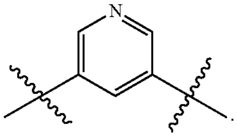

.

In another embodiment of the invention

A is

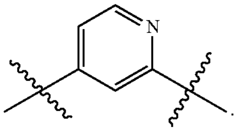

.

In another embodiment of the invention,

A is

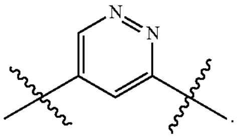

.

In another embodiment of the invention,

A is

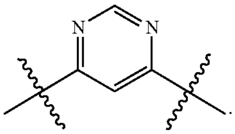

.

In another embodiment of the invention,
 is 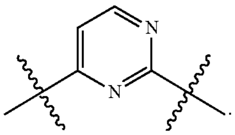
In another embodiment of the invention,
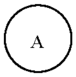 is 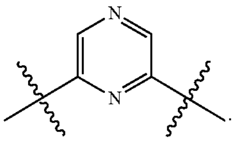
In another embodiment of the invention,
 is 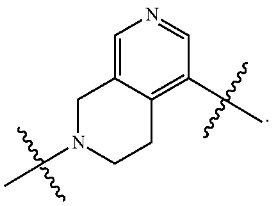
In an embodiment of the invention,
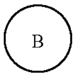 is 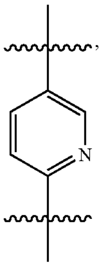 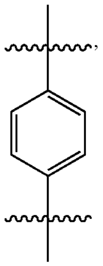 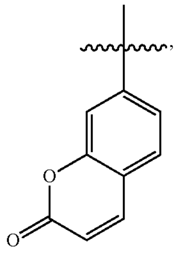
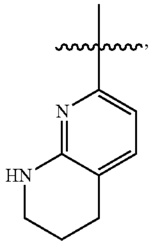 or 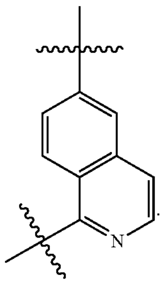
In a class of the embodiment,
 is 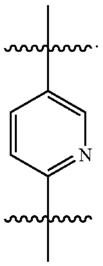
In another class of the embodiment,
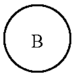 is 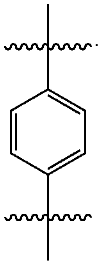
In another class of the embodiment,
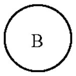 is 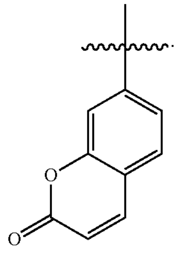
In another class of the embodiment.
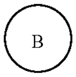 is 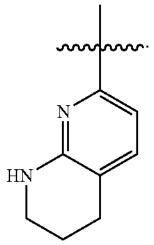

In another class of the embodiment,

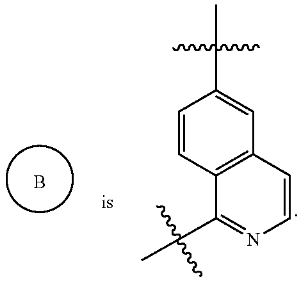

In an embodiment of the invention, $R^1$ is halo. In a class of the embodiment, $R^1$ is chloro. In another class of the embodiment, $R^1$ is fluoro.

In an embodiment of the invention, $R^2$ is halo. In a class of the embodiment, $R^2$ is chloro. In another class of the embodiment, $R^2$ is fluoro.

In an embodiment of the invention, $R^3$ is heterocyclyl, which is optionally substituted with one to three halo, or $R^x$. In another embodiment of the invention, $R^3$ is heteroaryl, which is optionally substituted with methyl or oxo.

In an embodiment of the invention, $R^4$ is hydrogen, cyclopropyl or methyl.

In an embodiment of the invention, $R^5$ is $C_{1-6}$ alkyl, which is optionally substituted with one to three halo, or cyano.

In an embodiment of the invention, n is zero. In another embodiment of the invention, n is one. In another embodiment of the invention, n is two.

In an embodiment of the invention, n is one, and $R^3$ is heteroaryl, which is optionally substituted with methyl or oxo.

In an embodiment of the invention, $R^4$ is hydrogen, cyclopropyl or methyl, and $R^5$ is $C_{1-6}$ alkyl, which is optionally substituted with one to three halo, or cyano.

Reference to the preferred classes and subclasses set forth above is meant to include all combinations of particular and preferred groups unless stated otherwise.

Specific embodiments of the present invention include, but are not limited to the compounds identified herein as Examples 1 to 52 or pharmaceutically acceptable salts thereof.

Also included within the scope of the present invention is a pharmaceutical composition which is comprised of a compound of Formula I, Ia or Ib as described above and a pharmaceutically acceptable carrier. The invention is also contemplated to encompass a pharmaceutical composition which is comprised of a pharmaceutically acceptable carrier and any of the compounds specifically disclosed in the present application. These and other aspects of the invention will be apparent from the teachings contained herein.

The invention includes compositions for treating diseases or condition in which plasma kallikrein activity is implicated. Accordingly the invention includes compositions for treating impaired visual activity, diabetic retinopathy, wet age-related macular degeneration, diabetic macular edema, retinal vein occlusion, hereditary angioedema, diabetes, pancreatitis, cerebral hemorrhage, nephropathy, cardiomyopathy, neuropathy, inflammatory bowel disease, arthritis, inflammation, septic shock, hypotension, cancer, adult respiratory distress syndrome, disseminated intravascular coagulation, blood coagulation during cardiopulmonary bypass surgery, and bleeding from postoperative surgery in a mammal, comprising a compound of the invention in a pharmaceutically acceptable carrier. A class of the invention includes compositions for treating hereditary angioedema, uveitis, posterior uveitis, wet age-related macular degeneration, diabetic macular edema, diabetic retinopathy and retinal vein occlusion. These compositions may optionally include anti-inflammatory agents, anti-VEGF agents, immunosuppressive agents, anticoagulants, antiplatelet agents, and thrombolytic agents. The compositions can be added to blood, blood products, or mammalian organs in order to effect the desired inhibitions.

The invention also includes compositions for preventing or treating retinal vascular permeability associated with diabetic retinopathy and diabetic macular edema in a mammal, comprising a compound of the invention in a pharmaceutically acceptable carrier. These compositions may optionally include anti-inflammatory agents, anti-VEGF agents, immunosuppressive agents, anticoagulants, antiplatelet agents, and thrombolytic agents.

The invention also includes compositions for treating inflammatory conditions of the eye, which includes, but is not limited to, uveitis, posterior uveitis, macular edema, acute macular degeneration, wet age-related macular degeneration, retinal detachments, retinal vein occlusion, ocular tumors, fungal infections, viral infections, multifocal choroiditis, diabetic uveitis, diabetic macular edema, diabetic retinopathy, proliferative vitreoretinopathy, sympathetic opthalmia, Vogt Koyanagi-Harada syndrome, histoplasmosis and uveal diffusion. These compositions may optionally include anti-inflammatory agents, anti-VEGF agents, immunosuppressive agents, anticoagulants, antiplatelet agents, and thrombolytic agents.

The invention also includes compositions treating posterior eye disease, which includes, but is not limited to, uveitis, posterior uveitis, wet age-related macular degeneration, diabetic macular edema, diabetic retinopathy and retinal vein occlusion. These compositions may optionally include anti-inflammatory agents, anti-VEGF agents, immunosuppressive agents, anticoagulants, antiplatelet agents, and thrombolytic agents.

It will be understood that the invention is directed to the compounds of structural Formula I, Ia and Ib described herein, as well as the pharmaceutically acceptable salts of the compounds of structural Formula I, Ia and Ib and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, butyrate, camphorate, camphorsulfonate, camsylate, carbonate, chloride, clavulanate, citrate, cyclopentane propionate, diethylacetic, digluconate, dihydrochloride, dodecylsulfanate, edetate, edisylate, estolate, esylate, ethanesulfonate, formic, fumarate, gluceptate, glucoheptanoate, gluconate, glutamate, glycerophosphate, glycollylarsanilate, hemisulfate, heptanoate, hexanoate, hexylresorcinate, hydrabamine, hydrobromide, hydrochloride, 2-hydroxyethanesulfonate, hydroxynaphthoate, iodide, isonicotinic, isothionate, lactate, lactobionate, laurate, malate, maleate, mandelate, mesylate, methylbromide, methylnitrate, methylsulfate, methanesulfonate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, phosphate/diphosphate, pimelic, phenylpropionic, polygalacturonate, propionate, salicylate, stearate, sulfate, subacetate, succinate, tannate, tartrate, teoclate, thiocyanate, tosylate, triethiodide, trifluoroacetate, undeconate, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also, included are the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

These salts can be obtained by known methods, for example, by mixing a compound of the present invention with an equivalent amount and a solution containing a desired acid, base, or the like, and then collecting the desired salt by filtering the salt or distilling off the solvent. The compounds of the present invention and salts thereof may form solvates with a solvent such as water, ethanol, or glycerol. The compounds of the present invention may form an acid addition salt and a salt with a base at the same time according to the type of substituent of the side chain.

If the compounds of Formula I, Ia or Ib simultaneously contain acidic and basic groups in the molecule the invention also includes, in addition to the salt forms mentioned, inner salts or betaines (zwitterions).

The present invention encompasses all stereoisomeric forms of the compounds of Formula I, Ia and Ib. Unless a specific stereochemistry is indicated, the present invention is meant to comprehend all such isomeric forms of these compounds. Centers of asymmetry that are present in the compounds of Formula I, Ia and Ib can all independently of one another have (R) configuration or (S) configuration. When bonds to the chiral carbon are depicted as straight lines in the structural Formulas of the invention, it is understood that both the (R) and (S) configurations of the chiral carbon, and hence both each individual enantiomer and mixtures thereof, are embraced within the Formula. When a particular configuration is depicted, that entantiomer (either (R) or (S), at that center) is intended. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

Unless a specific enantionmer or diastereomer is indicated, the invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I, Ia or Ib, or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (including hydrates) and solvated salts of such racemates, enantiomers, diastereomers and tautomers and mixtures thereof.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the specifically and generically described compounds. For example, different isotopic forms of hydrogen (H) include protium ($1_H$) and deuterium ($2_H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the general process schemes and examples herein using appropriate isotopically-enriched reagents and/or intermediates.

When any variable (e.g. $R^x$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off-target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted" (with one or more substituents) should be understood as meaning that the group in question is either unsubstituted or may be substituted with one or more substituents.

Furthermore, compounds of the present invention may exist in amorphous form and/or one or more crystalline forms, and as such all amorphous and crystalline forms and mixtures thereof of the compounds of Formula I, Ia and Ib are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with unsolvated and anhydrous forms.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$ alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

Except where noted herein, the terms "alkyl" and "alkylene" are intended to include both branched- and straight-chain saturated aliphatic hydrocarbon groups having the specified number of carbon atoms. Commonly used abbreviations for alkyl groups are used throughout the specification, e.g. methyl, may be represented by conventional abbreviations including "Me" or $CH_3$ or a symbol that is an extended bond as the terminal group, e.g.

"  ", ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-4}$ alkyl" (or "$C_1$-$C_4$ alkyl") for example, means linear or branched chain alkyl groups, including all isomers, having the specified number of carbon atoms. For example, the structures

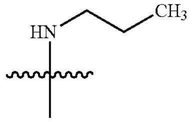 and 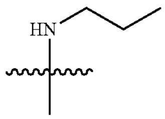

have equivalent meanings. $C_{1-4}$ alkyl includes n-, iso-, sec- and t-butyl, n- and isopropyl, ethyl and methyl. If no number is specified, 1-4 carbon atoms are intended for linear or branched alkyl groups.

Except where noted, the term "heteroaryl", as used herein, represents a stable monocyclic or bicyclic ring system of up to 10 atoms in each ring, wherein at least one ring is aromatic, and at least one ring contains from 1 to 4 heteroatoms selected from the group consisting of O, N and S. Bicyclic heteroaryl ring systems include fused ring systems, where two rings share two atoms, and spiro ring systems, where two rings share one atom. Heteroaryl groups within the scope of this definition include but are not limited to: azaindolyl, benzoimidazolyl, benzisoxazolyl, benzofuranyl, benzofurazanyl, benzopyrazolyl, benzotriazolyl, benzothiophenyl, benzoxazolyl, carbazolyl, carbolinyl, cinnolinyl, dihydroindenyl, furanyl, indolinyl, indolyl, indolazinyl, indazolyl, isobenzofuranyl, isoindolyl, isoquinolyl, isothiazolyl, isoxazolyl, naphthalenyl, naphthpyridinyl, oxadiazolyl, oxazolyl, oxazoline, isoxazoline, pyranyl, pyrazinyl, pyrazolyl, pyrazolopyrimidinyl, pyridazinyl, pyridopyridinyl, pyridinyl, pyridyl, pyrimidinyl, pyrrolyl, quinazolinyl, quinolyl, quinoxalinyl, tetrahydronaphthyridinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, dihydrobenzodioxinyl, dihydropyrazoloxazinyl, dihydropyrazolyothiazinedioxidyl, methylenedioxybenzene, benzothiazolyl, benzothienyl, quinolinyl, isoquinolinyl, oxazolyl, tetra-hydroquinoline, sulfolanyl, 1,3-benzodioxolyl, 3-oxo-3,4dihydro-2N-benzo[b][1,4]thiazine, imidazopyridinyl, 2-oxo-2,3-dihydroimidazolyl, 3,4-dihydrobenzoxazinyl, 2-oxo-2,3-dihydrooxazolyl, dihydroisobenzofuranyl, 1-oxoisoindolinyl, dioxido-2,3-dihydrobenzoisothiazolyl, 2-oxopyridyl, tetrahydroisoquinolyl, tetrahydrothiazolo[5,4-c]pyridyl, 4-oxo-dihydroquinazolinyl, dihydro-1'H-spirocyclopropane-1,4'-isoquinolyl. If the heteroaryl contains nitrogen atoms, it is understood that the corresponding N-oxides thereof are also encompassed by this definition.

The term "heterocycle" or "heterocyclyl" as used herein is intended to mean a stable nonaromatic monocyclic or bicyclic ring system of up to 10 atoms in each ring, unless otherwise specified, containing from 1 to 4 heteroatoms selected from the group consisting of 0, N, S, SO, or $SO_2$. Bicyclic heterocyclic ring systems include fused ring systems, where two rings share two atoms, and spiro ring systems, where two rings share one atom. "Heterocyclyl" therefore includes, but is not limited to the following: azabicyclohexanyl, azaspirohexanyl, azaspirononanyl, azaspirooctanyl, azetidinyl, dioxanyl, isochromanyl, oxadiazaspirodecenyl, oxaspirooctanyl, oxazolidinonyl, 2-oxo-azabicyclo[3.1.0]hexanyl, piperazinyl, piperidinyl, pyrrolidinyl, morpholinyl, thiomorpholinyl, tetrahydrofurnayl, tetrahydropyranyl, dihydropiperidinyl, tetrahydrothiophenyl and the like. If the heterocycle contains a nitrogen, it is understood that the corresponding N-oxides thereof are also encompassed by this definition.

Except where noted, the term "halogen" or "halo" means fluorine, chlorine, bromine or iodine.

"Celite®" (Fluka) diatomite is diatomaceous earth, and can be referred to as "celite".

Except where noted herein, structures containing substituent variables such as variable "R" below:

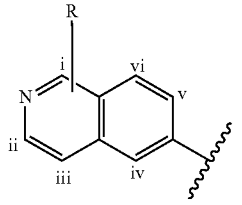

which are depicted as not being attached to any one particular bicyclic ring carbon atom, represent structures in which the variable can be optionally attached to any bicyclic ring carbon atom. For example, variable R shown in the above structure can be attached to any one of 6 bicyclic ring carbon atoms i, ii, iii, iv, v or vi.

Except where noted herein, bicyclic ring systems include fused ring systems, where two rings share two atoms, and spiro ring systems, where two rings share one atom.

The invention also relates to medicaments containing at least one compound of the Formula I, Ia and Ib and/or of a pharmaceutically acceptable salt of the compound of the Formula I, Ia and Ib and/or an optionally stereoisomeric form of the compound of the Formula I, Ia and Ib or a pharmaceutically acceptable salt of the stereoisomeric form of the compound of Formula I, Ia and Ib, together with a pharmaceutically suitable and pharmaceutically acceptable vehicle, additive and/or other active substances and auxiliaries.

The term "patient" used herein is taken to mean mammals such as primates, humans, sheep, horses, cattle, pigs, dogs, cats, rats, and mice.

The medicaments according to the invention can be administered by oral, inhalative, rectal or transdermal administration or by subcutaneous, intraarticular, intraperitoneal or intravenous injection. Oral administration is preferred. Coating of stents with compounds of the Formulas I and other surfaces which come into contact with blood in the body is possible.

The invention also relates to a process for the production of a medicament, which comprises bringing at least one compound of the Formula I or Ia into a suitable administration form using a pharmaceutically suitable and pharmaceutically acceptable carrier and optionally further suitable active substances, additives or auxiliaries.

Suitable solid or galenical preparation forms are, for example, granules, powders, coated tablets, tablets, (micro) capsules, suppositories, syrups, juices, suspensions, emulsions, drops or injectable solutions and preparations having prolonged release of active substance, in whose preparation customary excipients such as vehicles, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactose, gelatin, starch, cellulose and its derivatives, animal and plant oils such as cod liver oil, sunflower, peanut or sesame oil, polyethylene glycol and solvents such as, for example, sterile water and mono- or polyhydric alcohols such as glycerol.

The dosage regimen utilizing the plasma kallikrein inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the plasma kallikrein inhibitors, when used for the indicated effects, will range between about 0.01 mg per kg of body weight per day (mg/kg/day) to about 30 mg/kg/day, preferably 0.025-7.5 mg/kg/day, more preferably 0.1-2.5 mg/kg/day, and most preferably 0.1-0.5 mg/kg/day (unless specified otherwise, amounts of active ingredients are on free base basis). For example, an 80 kg patient would receive between about 0.8 mg/day and 2.4 g/day, preferably 2-600 mg/day, more preferably 8-200 mg/day, and most preferably 8-40 mg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the plasma kallikrein inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025-7.5 mg/kg/day, preferably 0.1-2.5 mg/kg/day, and more preferably 0.1-0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01-1.0 mg/mL, e.g. 0.1 mg/mL, 0.3 mg/mL, and 0.6 mg/mL, and administered in amounts per day of between 0.01 mL/kg patient weight and 10.0 mL/kg patient weight, e.g. 0.1 mL/kg, 0.2 mL/kg, 0.5 mL/kg. In one example, an 80 kg patient, receiving 8 mL twice a day of an intravenous formulation having a concentration of active ingredient of 0.5 mg/mL, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. The choice of appropriate buffer and pH of a formulation, depending on solubility of the drug to be administered, is readily made by a person having ordinary skill in the art.

Compounds of Formula I, Ia and Ib can be administered both as a monotherapy and in combination with other therapeutic agents, including but not limited to anti-inflammatory agents, anti-VEGF agents, immunosuppressive agents, anticoagulants, antiplatelet agents, and thrombolytic agents.

An “anti-inflammatory agent” is any agent which is directly or indirectly effective in the reduction of inflammation when administered at a therapeutically effective level. “Anti-inflammatory agent” includes, but is not limited to steroidal anti-inflammatory agents and glucocorticoids. Suitable anti-inflammatory agents include, but are not limited to, cortisone, dexamethasone, hydrocortisone, methylprednisolone, prednisolone, prednisone and triamcinolone.

An “anti-VEGF agent” is any agent which is directly or indirectly effective in inhibiting the activity of VEGF (Vascular Endothelial Growth Factor). Suitable anti-VEGF agents include, but are not limited to, bevacizumab, ranibizumab, brolucizumab and aflibercept.

An “immunosuppressant agent” is any agent which is directly or indirectly effective in suppressing, or reducing, the strength of the body’s immune system. Suitable immunosuppressant agents include, but are not limited to, corticosteroids (for example, prednisone, budesonide, prednisolone), janus kinase inhibitors (for example, tofacitinib), calcineurin inhibitors (for example, cyclosporin, tacrolimus), mTOR inhibitors (for example, sirolimus, everolimus), IMDH inhibitors (for example, azathioprine, leflunomide, mycophenolate), biologics (for example, abatacept, adalimumab, anakinra, certolizumab, etanercept, golimumab, infliximab, ixekizumab, natalizumab, rituximab, secukinumab, tocilizumab, ustekinumab, vedolizumab), and monoclonal antibodies (for example, basiliximab, daclizumab).

Suitable anticoagulants include, but are not limited to, factor XIa inhibitors, thrombin inhibitors, thrombin receptor antagonists, factor VIIa inhibitors, factor Xa inhibitors, factor IXa inhibitors, factor XIIa inhibitors, adenosine diphosphate antiplatelet agents (e.g., P2Y12 antagonists), fibrinogen receptor antagonists (e.g. to treat or prevent unstable angina or to prevent reocclusion after angioplasty and restenosis), other anticoagulants such as aspirin, and thrombolytic agents such as plasminogen activators or streptokinase to achieve synergistic effects in the treatment of various vascular pathologies. Such anticoagulants include, for example, apixaban, dabigatran, cangrelor, ticagrelor, vorapaxar, clopidogrel, edoxaban, mipomersen, prasugrel, rivaroxaban, and semuloparin. For example, patients suffering from coronary artery disease, and patients subjected to angioplasty procedures, would benefit from coadministration of fibrinogen receptor antagonists and thrombin inhibitors.

In certain embodiments the anti-inflammatory agents, anti-VEGF agents, immunosuppressant agents, anticoagulants, antiplatelet agents, and thrombolytic agents described herein are employed in their conventional dosage ranges and regimens as reported in the art, including, for example, the dosages described in editions of the *Physicians' Desk Reference*, such as the 70th edition (2016) and earlier editions. In other embodiments, the anti-inflammatory agents, anti-VEGF agents, immunosuppressant agents, anticoagulants, antiplatelet agents, and thrombolytic agents described herein are employed in lower than their conventional dosage ranges.

Alternatively or additionally, one or more additional pharmacologically active agents may be administered in combination with a compound of the invention. The additional active agent (or agents) is intended to mean a pharmaceutically active agent (or agents) that is active in the body, including pro-drugs that convert to pharmaceutically active form after administration, which is different from the compound of the invention, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of the invention in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); angiotensin II receptor antagonists also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g, olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®), etc.); potassium sparing diuretics such as amiloride HCl, spironolactone, epleranone, triamterene, each with or without HCTZ; neutral endopeptidase inhibitors (e.g., thiorphan and phosphoramidon); aldosterone antagonists; aldosterone synthase inhibitors; renin inhibitors; enalkrein; RO 42-5892; A 65317; CP 80794; ES 1005; ES 8891; SQ 34017; aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate)

SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazosin, prazosin or alpha methyldopa); central alpha adrenergic agonists; peripheral vasodilators (e.g. hydralazine); lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; inhibitors of glucose uptake, such as sodium-glucose transporter (SGLT) inhibitors and its various isoforms, such as SGLT-1, SGLT-2 (e.g., ASP-1941, TS-071, BI-10773, tofogliflozin, LX-4211, canagliflozin, dapagliflozin, ertugliflozin, ipragliflozin, remogliflozin and sotagliflozin), and SGLT-3; or with other drugs beneficial for the prevention or the treatment of the above-mentioned diseases including but not limited to diazoxide; and including the free-acid, free-base, and pharmaceutically acceptable salt forms, pro-drug forms, e.g., esters, and salts of pro-drugs of the above medicinal agents, where chemically possible. Trademark names of pharmaceutical drugs noted above are provided for exemplification of the marketed form of the active agent(s); such pharmaceutical drugs could be used in a separate dosage form for concurrent or sequential administration with a compound of the invention, or the active agent(s) therein could be used in a fixed dose drug combination including a compound of the invention.

Typical doses of the plasma kallikrein inhibitors of the invention in combination with other suitable agents may be the same as those doses of plasma kallikrein inhibitors administered without coadministration of additional agents, or may be substantially less that those doses of plasma kallikrein inhibitors administered without coadministration of additional agents, depending on a patient's therapeutic needs.

The compounds are administered to a mammal in a therapeutically effective amount. By "therapeutically effective amount" it is meant an amount of a compound of the present invention that, when administered alone or in combination with an additional therapeutic agent to a mammal, is effective to treat (i.e., prevent, inhibit or ameliorate) the disease condition or treat the progression of the disease in a host.

The compounds of the invention are preferably administered alone to a mammal in a therapeutically effective amount. However, the compounds of the invention can also be administered in combination with an additional therapeutic agent, as defined below, to a mammal in a therapeutically effective amount. When administered in a combination, the combination of compounds is preferably, but not necessarily, a synergistic combination. Synergy, as described for example by Chou and Talalay, *Adv. Enzyme Regul.* 1984, 22, 27-55, occurs when the effect (in this case, inhibition of the desired target) of the compounds when administered in combination is greater than the additive effect of each of the compounds when administered individually as a single agent. In general, a synergistic effect is most clearly demonstrated at suboptimal concentrations of the compounds. Synergy can be in terms of lower cytotoxicity, increased anticoagulant effect, or some other beneficial effect of the combination compared with the individual components.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect. The administration of each component does not need to be via the same route of administration; for example, one component can be administered orally, and another can be delivered into the vitreous of the eye.

The present invention is not limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claims.

General Methods

Compounds of the present invention may be prepared using conventional techniques or according to the methodology outlined in the following general synthetic schemes. One skilled in the art can vary the procedures and reagents shown to arrive at similar intermediates and/or final compounds.

NMR spectra were measured on VARIAN or Bruker NMR Systems (400, 500 or 600 MHz). Chemical shifts are reported in ppm downfield and up field from tetramethylsilane (TMS) and referenced to either internal TMS or solvent resonances ($^1$H NMR: δ 7.27 for $CDCl_3$, δ 2.50 for $(CD_3)(CHD_2)SO$, and $^{13}$C NMR: δ 77.02 for $CDCl_3$, δ 39.51 for $(CD_3)_2SO$. Coupling constants (J) are expressed in hertz (Hz), and spin multiplicities are given as s (singlet), d (doublet), dd (double doublet), t (triplet), m (multiplet), and br (broad). Chiral resolutions can be performed on either Waters Thar 80 SFC or Berger MG II preparative SFC systems. LC-MS data can be recorded on SHIMADAZU LC-MS-2020, SHIMADAZU LC-MS-2010, or Agilent 1100 series LC-MS, Agilent Prime-1260, or Waters Acquity LC-MS instruments using C18 columns employing a MeCN gradient in water containing 0.02 to 0.1% TFA. UV detections were at 220 and/or 254 nm and ESI ionization was used for MS detection.

When chiral resolution was achieved by chromatography using chiral columns, the chiral columns used for SFC chiral resolutions are listed in tables. Some of the chiral columns used were CHIRALPAK AD, CHIRALCEL OJ, CHIRALPAK AS, CHIRALPAK AY, CHIRALPAK IA, CHIRALPAK AD-H, and CHIRALPAK AS-H. Henceforth, they will be referred by their two or three letter abbreviations. As a convention, the fast-eluting isomer from a chiral resolution is always listed first in this table followed immediately by the slower-eluting isomer from the same resolution. If more than two isomers were separated, they will be always listed in the tables in order they were eluted, such as Peak 1 followed by Peak 2, Peak 3 and so on. A * symbol near a chiral center in a structure denotes that this chiral center was resolved by chiral resolution without its stereochemical configuration unambiguously determined.

Several catalysts and ligands are used in the following procedures. “RuPhos” is 2-Dicyclohexylphosphino-2',6'-diisopropoxybiphenyl. “RuPhos Pd G3” is (2-Dicyclohexylphosphino-2',6'-diisopropoxy-1,1'-biphenyl)[2-(2'-amino-1,1'-biphenyl]palladium(II) methanesulfonate. “Xphos” is 2-dicyclohexylphosphino-2',4',6'-triisopropylbiphenyl. “Xphos Pd G3” is (2-Dicyclohexylphosphino-2',4',6'-triisopropyl-1,1'-biphenyl)[2-(2'-amino-1,1'-biphenyl)]palladium (II) methanesulfonate. “Ni(II) pre-catalyst ([Ni(dtbbpy)$(H_2O)_4$]$Cl_2$)” is [4,4'-bis(1,1-dimethylethyl)-2,2'-bipyridine] nickel(II) dichloride. “[Ir{dF$CF_3$ppy}$_2$(dtbbpy)]$PF_6$” is [4,4'-Bis(1,1-dimethylethyl)-2,2'-bipyridine-$N^1$,$N^{1'}$]bis[3,5-difluoro-2-[5-(trifluoromethyl)-2-pyridinyl-N]phenyl-C] Iridium(III) hexafluorophosphate. These catalysts and ligands are available from Millipore Sigma.

Also, TLC is thin layer chromatography; UV is ultraviolet; W is watts; wt. % is percentage by weight; xg is times gravity; $\alpha_D$ is the specific rotation of polarized light at 589 nm; ° C. is degrees Celsius; % w/v is percentage in weight of the former agent relative to the volume of the latter agent; cpm is counts per minute; $\delta_H$ is chemical shift; Rochelle’s salt is potassium sodium tartrate; MS is mass spectrum, and a mass spectrum obtained by ES-MS may be denoted herein by “LC-MS”; m/z is mass to charge ratio.

For purposes of this specification, the following abbreviations have the indicated meanings:

Ac Acetyl
ACN Acetonitrile
AcOH acetic acid
aq. aqueous
BINAP 2,2'-bis(diphenylphosphino)-1,1'-binaphthyl
Boc or BOC tert-butoxycarbonyl
br broad
Bu or $^n$Bu Butyl (normal)
calcd. calculated
δ chemical shift
d doublet
dba dibenzylidineacetone
DCM dichloromethane
dd doublet of doublets
DIEA or N,N-diisopropylethylamine
Hüinig’s base
DMF dimethylformamide
DMSO dimethyl sulfoxide
DTT dithiothreitol
EDC 1-ethyl-3-(3-dimethylaminopropyl)carbodiimide
EDTA ethylenediamine tetraacetic acid
equiv. equivalent
ESI electrospray ionization
Et ethyl
$Et_2O$ diethyl ether
EtOH ethanol
EtOAc ethyl acetate
g grams
GST glutathione S-transferase
h hour
HATU N,N,N',N'-tetramethyl-O-(7-azabenzotriazol-1-yl) uronium hexafluorophosphate
HPLC high-performance liquid chromatography
Hz Hertz
IPA isopropanol
$^i$Pr isopropyl
J coupling constant
LC liquid chromatography
LCMS liquid chromatography mass spectrometry
LED light emitting diode
m multiplet
M molar
Me methyl
MeOH methanol
mg milligrams
MHz megahertz
min minute
μL microliters
mL milliliters
mM millimolar
mmol millimoles
MS mass spectrometry
N nitrogen substituted
nm nanometer
NMR nuclear magnetic resonance spectroscopy
OAc acetate
Ph phenyl
Pr propyl
q quartet
rac racemic mixture
RT or rt room temperature (ambient, about 25° C.)
s singlet
satd. saturated
SFC supercritical fluid chromatography
t triplet
T3P propanephosphonic acid anhydride
$^t$Bu tert-butyl
$^t$BuOH tert-butyl alcohol
TEA triethylamine ($Et_3N$)
tert tertiary
TFA trifluoroacetic acid
THF tetrahydrofuran
TLC thin layer chromatography
Tris tris(hydroxymethyl)aminomethane

General

Starting materials used were obtained from commercial sources or prepared in other examples, unless otherwise noted.

The methods used for the preparation of the compounds of this invention are illustrated by the following schemes. Unless specified otherwise, all starting materials used are commercially available.

General Schemes

Scheme A.

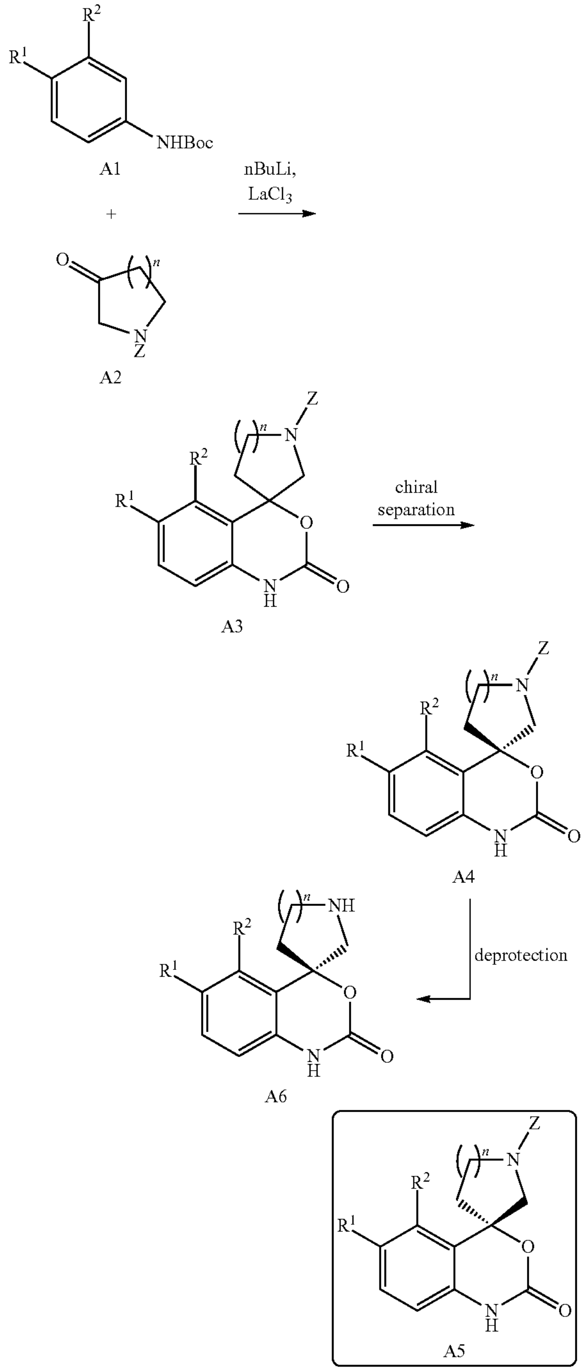

Z is any suitable protecting group

Scheme A illustrates the synthetic sequence for preparation of substituted spirocarbamates A6 from a Boc-protected aniline A1 and ketone A2. Directed lithiation of aniline A1 and addition into the heterocyclic ketone A2 occurs in the presence of Lewis acid (eg. LaCl3). The tertiary alcohol undergoes in situ cyclization onto the carbamate to give spirocarbamate derivative A3, which can be subjected to chiral separation, preferably using supercritical flow chromatography (SFC) to afford enantiomers A4 and A5. Deprotection of either enantiomer (A4, e.g.) gives the secondary amine A6.

Scheme B.

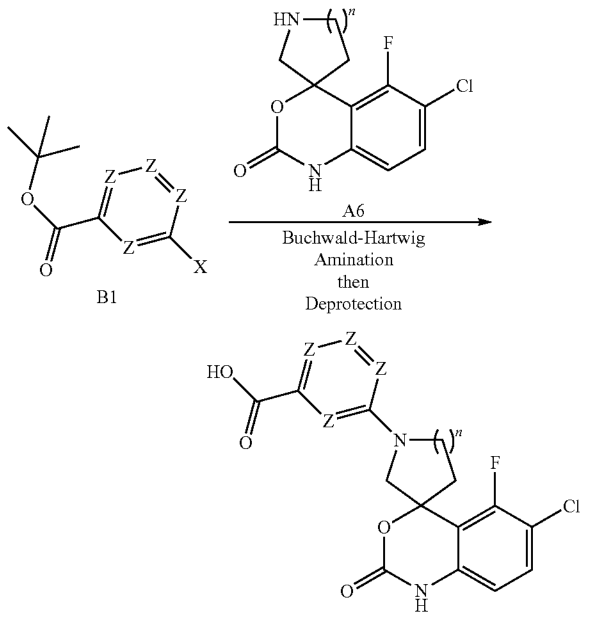

X is a suitable leaving group, such as Cl or Br
Z is N or CH

Scheme B illustrates the synthetic sequence for preparation of N-heteroarylated carboxylic acids of spirocarbamate B3 from halogen-bearing heteroaromatic tert-butyl ester B1 and spirocarbamate B2. A Buchwald-Hartwig amination between B1 and B2 can be affected using a suitable palladium pre-catalyst containing a monodentate phosphine ligand, such as RuPhos Pd G3, and suitable alkoxide base, such as NaO$^t$Bu, followed by deprotection with TFA to give spirocarbamate derivative B3.

Scheme C.

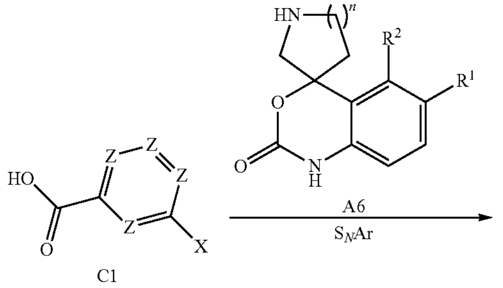

-continued

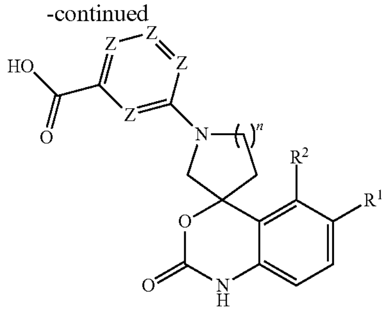

C3

X is a suitable leaving group, such as Cl or Br
Z is N or CH

Scheme C illustrates the synthetic sequence for preparation of N-heteroarylated carboxylic acids of spirocarbamate C3 from halogen-bearing heteroaromatic carboxylic acid C1 and spirocarbamate C2. $S_NAr$ between C1 and C2 can be affected using a suitable amine base, such as TEA or DIEA, or a solid base, such as $Cs_2CO_3$ or $NaO^tBu$, or the like, to give spirocarbamate derivative C3.

Scheme D.

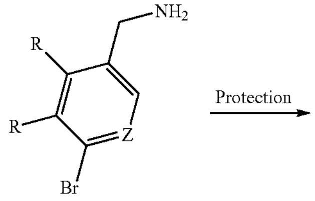

D1

-continued

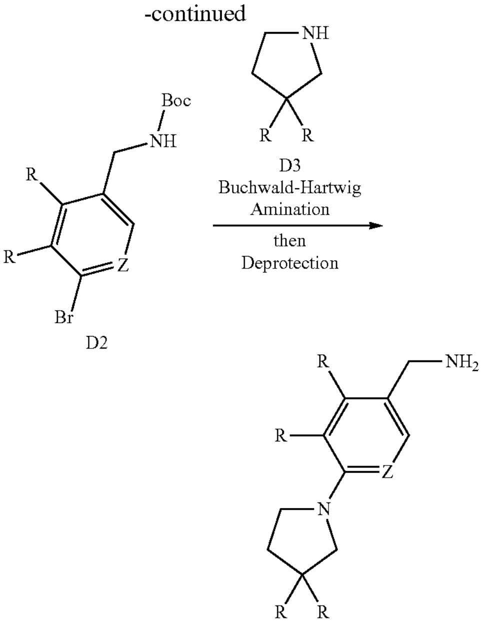

D2

D4

R is any suitable group as defined for Formula I
Z is N or CH

Scheme D illustrates the synthetic sequence for preparation of substituted N-linked pyrrolidyl benzylamine D4 from Boc-protected benzylamine D2 and substituted pyrrolidine D3. Boc-protection of benzylamine D1 afford Boc-protected intermediate D2, which can be reacted with substituted pyrrolidine D3 in a Buchwald-Hartwig amination using a suitable palladium pre-catalyst, such as RuPhos Pd 3G or XPhos Pd 3G. Alternatively, a suitable palladium (0) source can be used, such as $Pd_2(dba)_3$, in the presence of a suitable phosphine ligand, such as RuPhos, XPhos, or BINAP, to affect the transformation. In either case, the amination reaction is conducted in the presence of an appropriate base, such as $NaO^tBu$ or $Cs_2CO_3$. Deprotection using TFA affords substituted pyrrolidyl benzylamine D4.

Scheme E.

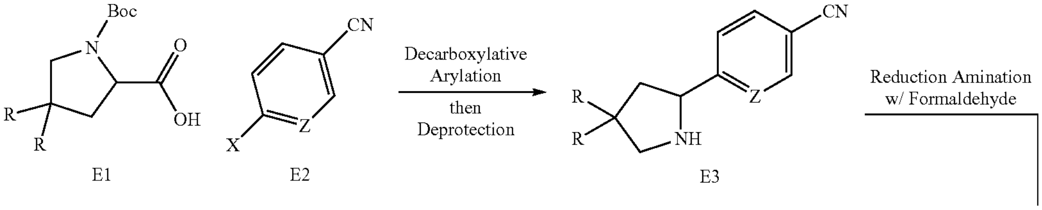

E1

E2

E3

-continued

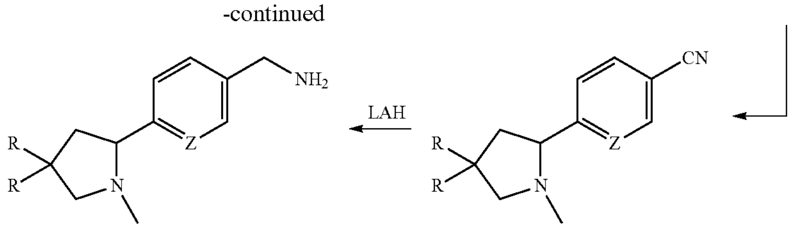

E5 E4

R is any suitable group as defined for Formula I
X is a suitable leaving group
Z is N or CH Scheme E illustrates the synthetic sequence for preparation of substituted C-2-linked pyrrolidyl benzylamine E5 from Boc-protected 2-carboxylpyrrolidine E1 and cyanoaryl halide E2. Decarboxylative arylation using dual Ir/Ni catalysis with E1 and E2 is conducted using a combination of suitable Ir-photocatalyst, such as [Ir{dF($CF_3$)ppy}$_2$(bpy)]$PF_6$, Ni(II) pre-catalyst ([Ni(dtbbpy)($H_2O$)$_4$]$Cl_2$), in the presence of a suitable base, such as $Cs_2CO_3$. Reactions can be performed in a photoreactor equipped with a blue LED. The resulting Boc-protected intermediates are deprotected with TFA to afford C-2-linked pyrrolidyl nitrile aromatic E3. N-methylation can be achieved by way of reductive amination with formaldehyde using a mild reducing agent [NaHB($OAc)_3$, e.g.] to afford intermediate E4. Reduction of the nitrile with a suitable reducing agent, such as LAH, yields substituted C-2-linked pyrrolidyl benzylamine E5.

Scheme F.

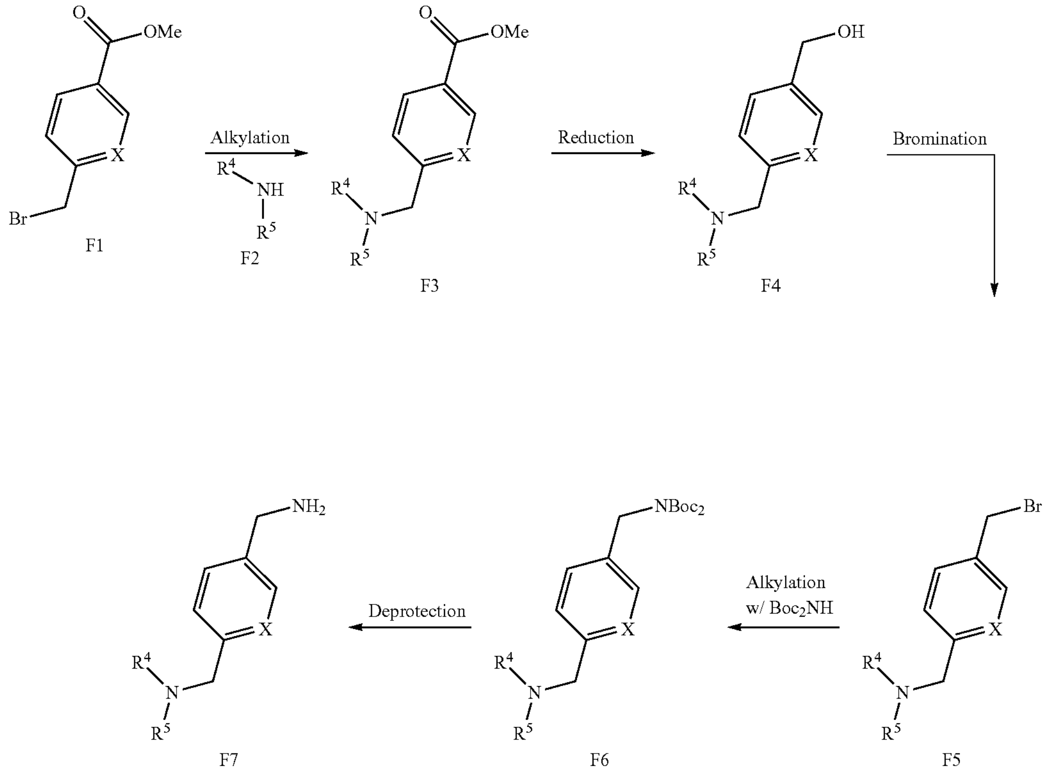

F1 F2 F3 F4 F5 F6 F7

X is N or CH

Scheme F illustrates the synthetic sequence for preparation of benzylamine F7 from benzyl bromide F1 and nitrogen heterocycle F2. Alkylation between benzyl bromide F1 and nitrogen heterocycle F2 can be carried out in the presence of a suitable base, such as $K_2CO_3$ or NaH, to give alkylated intermediate F3. The subsequent reduction of the methyl ester to the alcohol is affected with a mild reducing agent, such as $NaBH_4$, to give benzylic alcohol intermediate F4. Conversion to the benzylic bromide occurred with a suitable brominating reagent ($PBr_3$ or HBr, e.g.) affords intermediate F5, which can be subjected to alkylation with bis-Boc amine to give Boc-protected intermediate F6. Deprotection with TFA yields benzyl amine intermediate F7.

Scheme G.

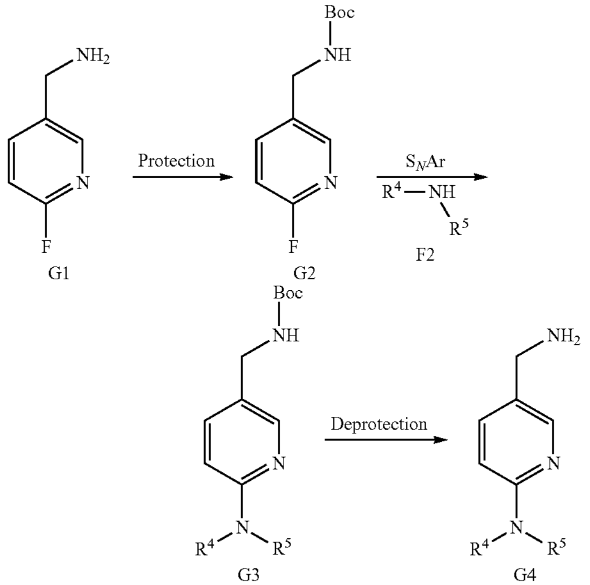

G1 G2 G3 G4

Scheme G illustrates the synthetic sequence for preparation of benzylamine G5 from fluoropyridine G1. Fluoropyridine G1 is first Boc-protected to give intermediate G2, followed by $S_NAr$ reaction with disubstituted amines such G3 using a suitable base, as indicated previously in Scheme C, to give Boc-protected intermediate G4, which can subsequently be deprotected with TFA to afford benzyl amine intermediate G5.

Scheme H.

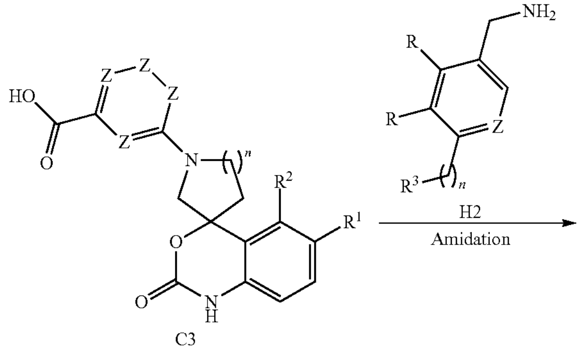

C3

-continued

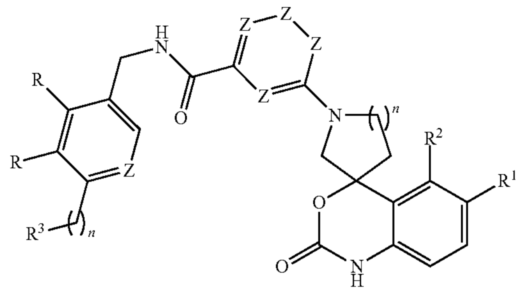

H3

R is any suitable group as defined for Formula I
Z is N or CH

Scheme H illustrates the synthetic sequence for preparation of amide H3 from carboxylic acid H1 and amine H2. Amide coupling between H1 and H2 is performed with a suitable amide coupling reagent, such as HATU or T3P, in the presence of an appropriate amine base (TEA or DIEA) to afford amide H3.

Scheme I.

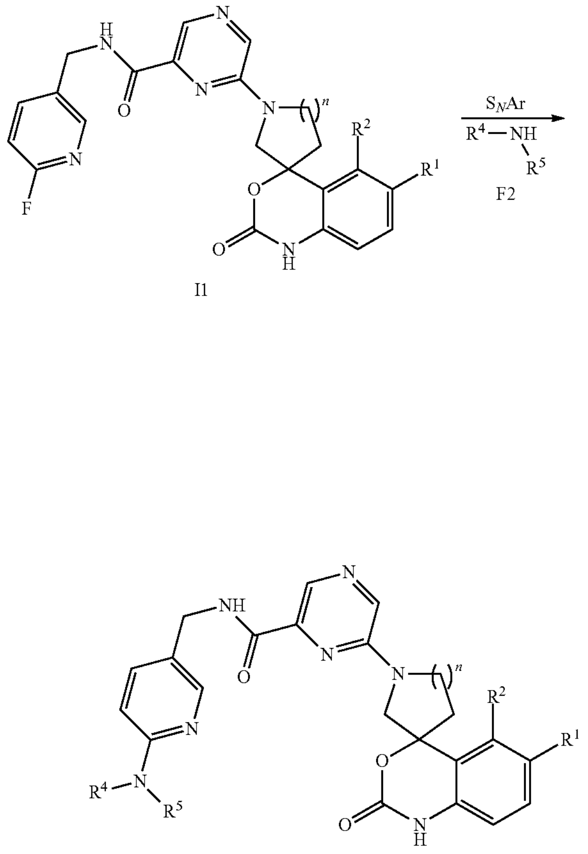

I1

I2

Scheme I illustrates the synthetic sequence for preparation of $S_NAr$ adduct I2 from fluoropyridine intermediate I1 and disubstituted amine F2. $S_NAr$ between fluoropyridine I1 and disubstituted amine F2 is performed using a suitable base, as indicated previously in Scheme C, to afford $S_NAr$ adduct I2.

Scheme J.
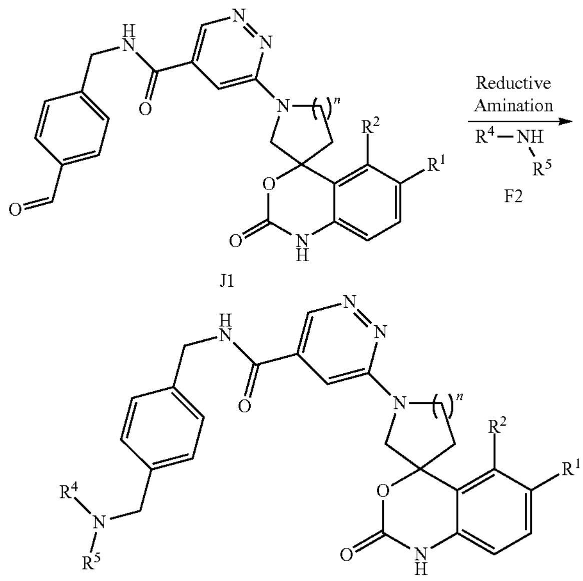
J1
J2
Scheme J illustrates the synthetic sequence for preparation of reductive amination product J2 from benzaldehyde precursor J1 and substituted amine F2. The reductive amination between J1 and F2 proceeds following similar conditions as those described above in Scheme E to afford the desired target (J2).
Scheme K.
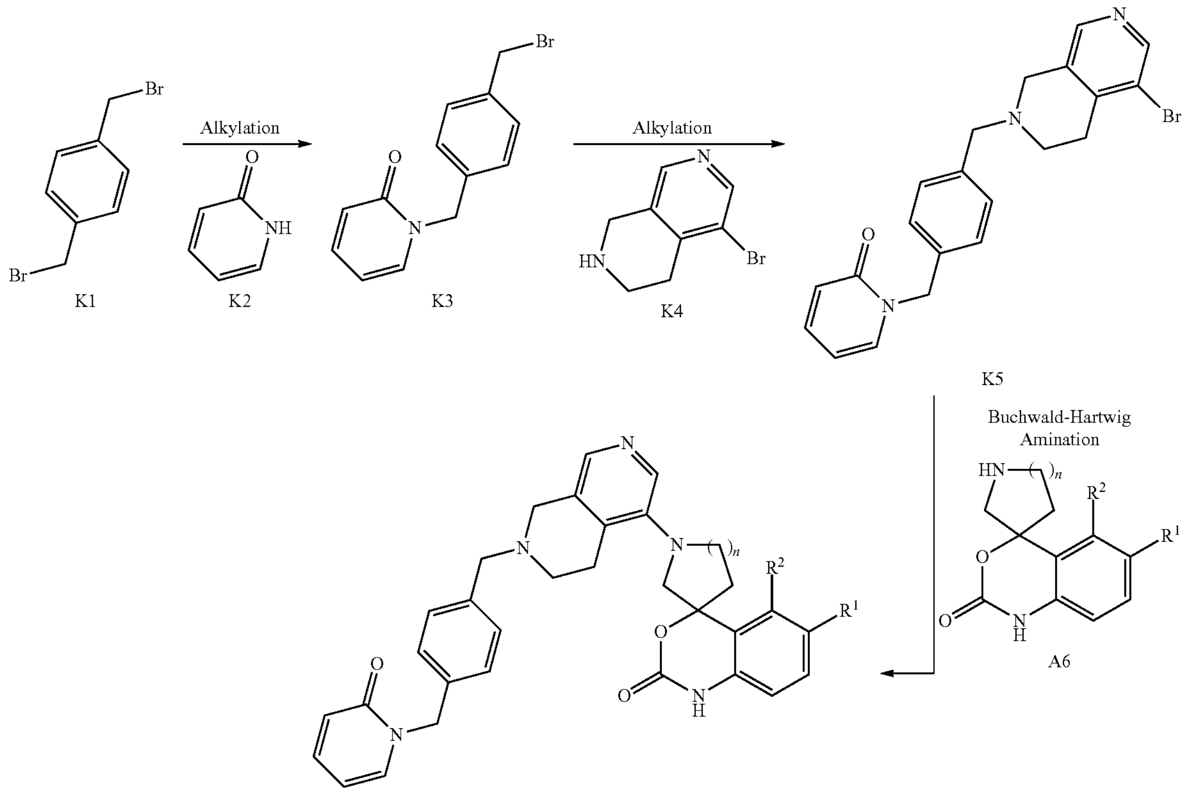
K1 K2 K3 K4 K5 A6 K7

Scheme K illustrates the synthetic sequence for the construction of napthyhydrin intermediate K7. Alkylation of dibromo xylene K1 with pyridone K2 is performed in the presence of a suitable base, such as $K_2CO_3$, to afford benzyl bromide intermediate K3, which undergoes alkylation with napthyhydrin K4 to afford napthyhydrin bromide K5. Napthyhydrin bromide K5 is coupled to spirocarbamate A6 using Buchwald-Hartwig amination conditions using conditions similar to those described above in Scheme D to afford napthyhydrin K7.

Scheme L.

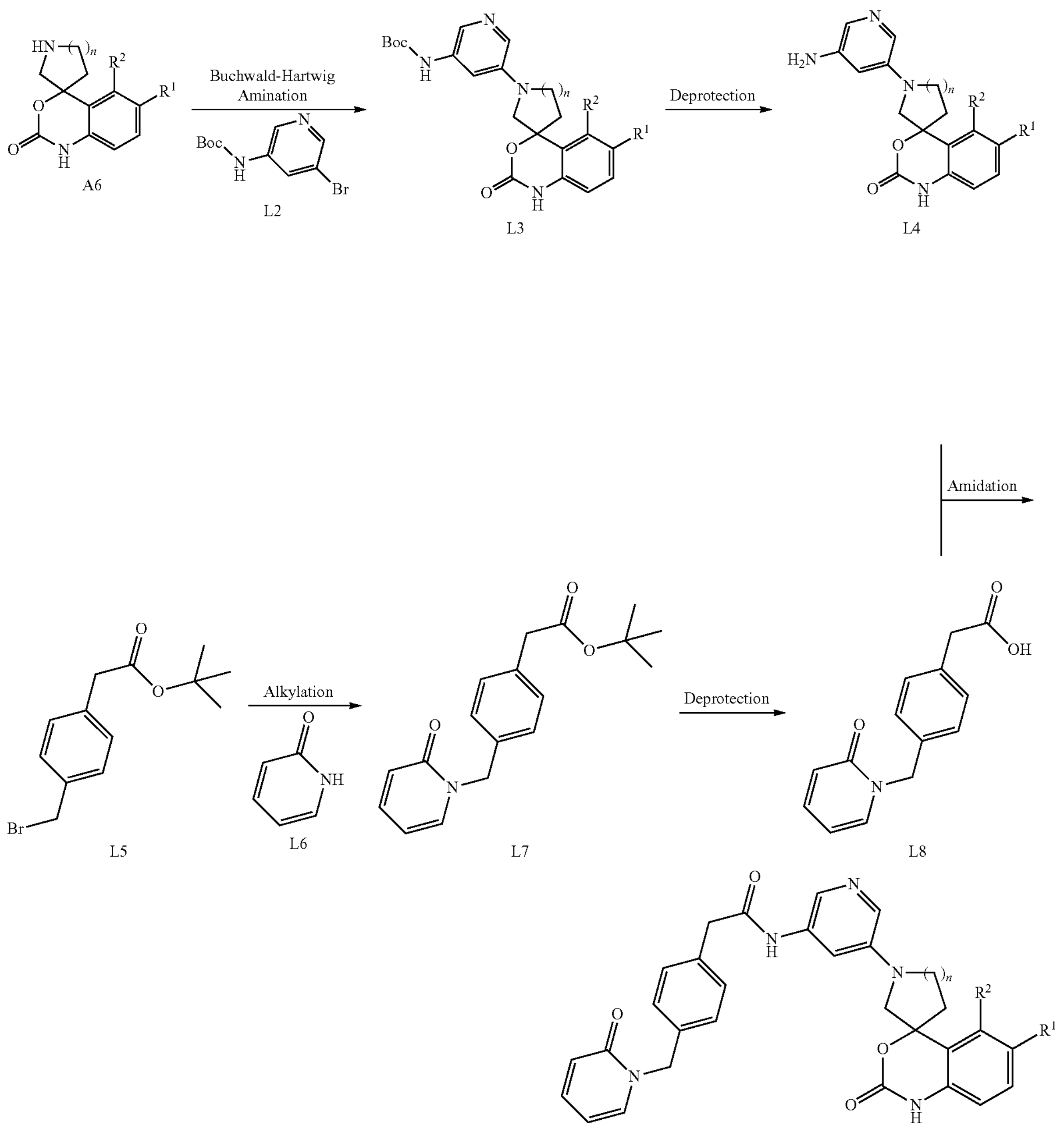

A6 L2 L3 L4

L5 L6 L7 L8

L9

Scheme L illustrates the synthetic sequence for the construction of acetamide L9. To arrive at amine L4, spirocarbamate L1 and aryl bromide L2 are coupled by way of Buchwald-Hartwig amination conditions as described above in Scheme D to afford Boc-protected intermediate L3 which can be deprotected using TFA to give amine L4. To arrive at carboxylic acid L8, pyridone L6 is alkylated with ester L5 using a suitable base, such as NaH, to afford an ester intermediate L7 that is then deprotected with TFA to give carboxylic acid L8. Amine L4 and carboxylic acid L8 are reacted under similar conditions to those described above in Scheme H to afford acetamide L9.

Intermediate i-1

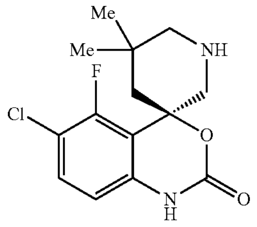

(R)-6-Chloro-5-fluoro-5',5'-dimethylspiro[benzo[d][1,3]oxazine-4,3'-piperidin]-2(1H)-one Step 1: tert-Butyl 6-chloro-5-fluoro-5',5'-dimethyl-2-oxo-1,2-dihydrospiro[benzo[d][1,3]oxazine-4,3'-piperidine]-1'-carboxylate: THF (55 mL) was added to tert-butyl (4-chloro-3-fluorophenyl)carbamate (2.21 g, 9.0 mmol) under a $N_2$ atmosphere. The solution was cooled down to −78° C. To the stirring solution, nBuLi (11 mL of a 2.5 M hexanes solution, 27.9 mmol) was added over 40 min. The reaction mixture was allowed to stir at −78° C. for an additional 45 min. Then, a solution of $LaCl_3$•2LiCl (22.5 mL of a 0.6 M THF solution, 13.5 mmol) and tert-butyl 3,3-dimethyl-5-oxopiperidine-1-carboxylate (3.1 g, 13.5 mmol) was added at −78° C. over a period of 40 min to the reaction mixture. The reaction mixture was allowed to warm to rt and stirred for 16 h. KOtBu (5.3 mL of a 1.7 M THF solution, 9.0 mmol) was added to the reaction mixture, the solution was heated to 60° C. and stirred for an additional 3 h. Then, the flask was cooled to rt, quenched with 1 M HCl and diluted with EtOAc. The layers were separated and the aq. phase extracted with EtOAc. The combined organic layers were dried over $MgSO_4$, filtered and concentrated under reduced pressure. The crude residue was purified by column chromatography (silica gel, hexanes:EtOAc) to afford mixture of enantiomers of the title compound. The enantiomeric title compounds were separated by chiral chromatography (SFC, DAICEL CHIRALPAK IC; 0.1% $NH_3H_2O$-IPA Begin B 25% End B 25%) to furnish the individual isomer compounds in pure form. The faster eluting S-enantiomer of the title compound was obtained: $[M+Na]^+$=421.2 (calcd. 421.1). The slower eluting desired isomer of the title compound was obtained (R-enantiomer): LCMS $[M+Na]^+$=421.2 (calcd. 421.1).

Step 2: (R)-6-Chloro-5-fluoro-5',5'-dimethylspiro[benzo[d][1,3]oxazine-4,3'-piperidin]-2(1H)-one: HCl (25 mL of a 4 M dioxane solution, 100 mmol) was added to a suspension of (R)-tert-butyl 6-chloro-5-fluoro-5',5'-dimethyl-2-oxo-1,2-dihydrospiro[benzo[d][1,3]oxazine-4,3'-piperidine]-1'-carboxylate (7.98 g, 20 mmol) in 1,4-dioxane (30 mL). The reaction mixture was heated to 90° C. and stirred vigorously for 12 h. Then, the flask was cooled to rt and the solvents were removed under reduced pressure to give the crude title compound. The crude product was carried forward to the next step without further purification. LCMS $[M+H]^+$=299.1 (calcd. 299.1).

Intermediate Table 1. The following compounds were prepared using procedures similar to those described for Intermediate i-1 using the appropriate starting materials.

| Intermediate | Structure | Name | LCMS $[M + H]^+$ |
|---|---|---|---|
| i-2 | 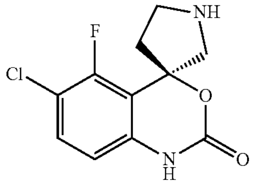 [SMILES: O=C1Nc2ccc(Cl)c(F)c2[C@@]2(CCNC2)O1] | (R)-6-Chloro-5-fluorospiro[benzo[d][1,3]oxazine-4,3'-pyrrolidin]-2(1H)-one | Calcd. 257.1, found 257.0 |
| i-3 | 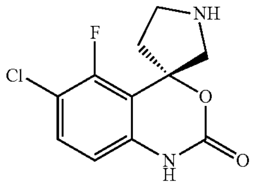 [SMILES: O=C1Nc2ccc(Cl)c(F)c2[C@]2(CCNC2)O1] | (S)-6-Chloro-5-fluorospiro[benzo[d][1,3]oxazine-4,3'-pyrrolidin]-2(1H)-one | Calcd. 257.1, found 257.0 |
| i-4 | 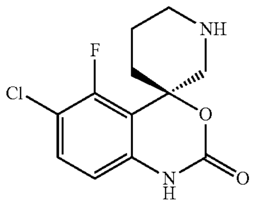 [SMILES: O=C1Nc2ccc(Cl)c(F)c2[C@@]2(CCCNC2)O1] | (R)-6-Chloro-5-fluorospiro[benzo[d][1,3]oxazine-4,3'-piperidin]-2(1H)-one | Calcd. 271.1, found 271.0 |

-continued

| Intermediate | Structure | Name | LCMS [M + H]$^+$ |
|---|---|---|---|
| i-5 | 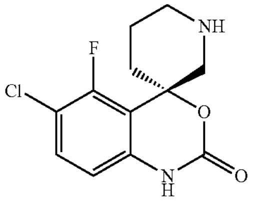 [SMILES: O=C1Nc2ccc(Cl)c(F)c2[C@]2(CCCNC2)O1] | (S)-6-Chloro-5-fluorospiro[benzo[d][1,3]oxazine-4,3'-piperidin]-2(1H)-one | Calcd. 271.1, found 271.0 |

Intermediate i-6

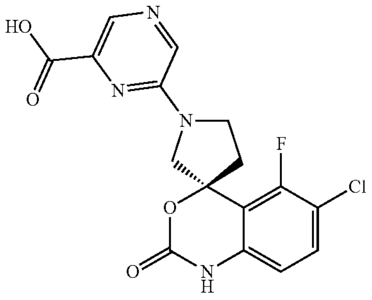

(S)-6-(6-Chloro-5-fluoro-2-oxo-1,2-dihydrospiro [benzo[d][1,3]oxazine-4,3'-pyrrolidin]-1'-yl)pyrazine-2-carboxylic acid A mixture of tert-butyl 6-chloropyrazine-2-carboxylate (254 mg, 1.18 mmol), (S)-6-chloro-5-fluorospiro[benzo[d][1,3]oxazine-4,3'-pyrrolidin]-2(1H)-one 2,2,2-trifluoroacetate (483 mg, 1.30 mmol), sodium tert-butoxide (341 mg, 3.55 mmol), and methanesulfonato(2-dicyclohexylphosphino-2',6'-di-i-propoxy-1,1'-biphenyl)(2'-amino-1,1'-biphenyl-2-yl)palladium (99 mg, 0.12 mmol) was diluted in 1,4-dioxane (3.5 mL) and sonicated for approximately 1 min. The reaction was then heated to 100° C. and allowed to stir at 100 □C overnight. The reaction was cooled to rt, TFA (2 mL) was added, and the resulting mixture was allowed to stir at rt for 1 h. The mixture was concentrated, and the crude residue was purified by reversed-phase preparatory-HPLC (C18 stationary phase, ACN/water+0.1% TFA) to afford the title compound. LCMS [M+H]$^+$=379.1 (calcd. 379.1).

Intermediate Table 2. The following compounds were prepared using procedures similar to those described for Intermediate i-6 using the appropriate starting materials.

| Intermediate | Structure | Name | LCMS [M + H]$^+$ |
|---|---|---|---|
| i-7 | 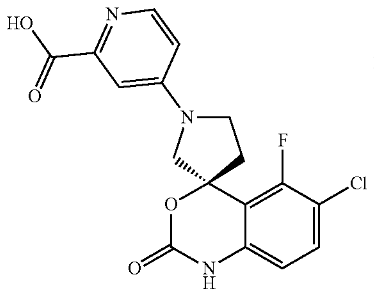 [SMILES: O=C1Nc2ccc(Cl)c(F)c2[C@]2(CCN(c3ccnc(C(=O)O)c3)C2)O1] | (S)-4-(6-Chloro-5-fluoro-2-oxo-1,2-dihydrospiro[benzo[d][1,3]oxazine-4,3'-pyrrolidin]-1'-yl)picolinic acid | Calcd. 378.1, found 378.0 |

-continued

| Intermediate | Structure | Name | LCMS [M + H]+ |
|---|---|---|---|
| i-8 | 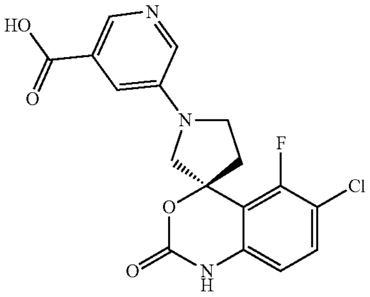 [SMILES: O=C1Nc2ccc(Cl)c(F)c2[C@]2(CCN(c3cncc(C(=O)O)c3)C2)O1] | (S)-5-(6-Chloro-5-fluoro-2-oxo-1,2-dihydrospiro[benzo[d][1,3]oxazine-4,3'-pyrrolidin]-1'-yl)nicotinic acid | Calcd. 378.1, found 378.0 |

Intermediate i-9

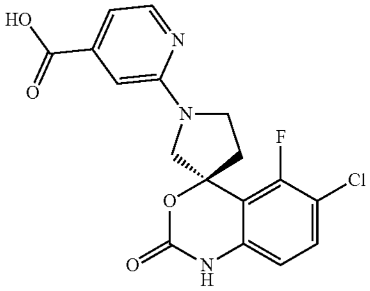

(S)-2-(6-Chloro-5-fluoro-2-oxo-1,2-dihydrospiro[benzo[d][1,3]oxazine-4,3'-pyrrolidin]-1'-yl)isonicotinic acid 1,4-Dioxane (0.3 mL) was added to a mixture of ethyl 6-chloropyrimidine-4-carboxylate (25 mg, 0.14 mmol), (S)-6-chloro-5-fluorospiro[benzo[d][1,3]oxazine-4,3'-pyrrolidin]-2(1H)-one hydrochloride (44 mg, 0.15 mmol), and sodium tert-butoxide (39 mg, 0.41 mmol), and the resulting mixture was sonicated for approximately 1 min. The reaction was heated to 100° C. for 30 min, cooled to rt, and concentrated to afford a crude residue that was purified by reversed-phase preparatory-HPLC (C18 stationary phase, ACN/water+0.1% TFA). LCMS $[M+H]^+$=378.0 (calcd. 378.1).

Intermediate Table 3. The following compounds were prepared using procedures similar to those described for Intermediate i-9 using the appropriate starting materials.

| Intermediate | Structure | Name | LCMS [M + H]+ |
|---|---|---|---|
| i-10 | 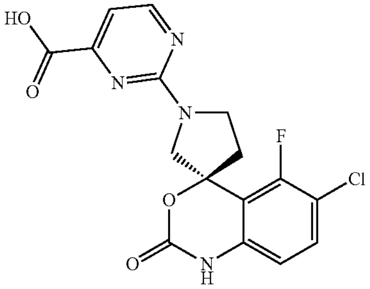 [SMILES: O=C1Nc2ccc(Cl)c(F)c2[C@]2(CCN(c3nccc(C(=O)O)n3)C2)O1] | (S)-2-(6-Chloro-5-fluoro-2-oxo-1,2-dihydrospiro[benzo[d][1,3]oxazine-4,3'-pyrrolidin]-1'-yl)pyrimidine-4-carboxylic acid | Calcd. 379.1, found 378.9 |

-continued

| Intermediate | Structure | Name | LCMS [M + H]$^+$ |
|---|---|---|---|
| i-11 | 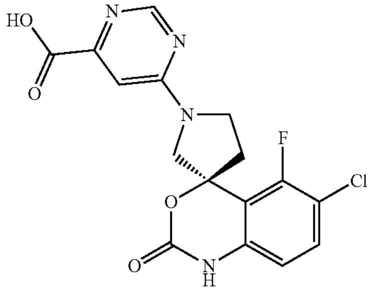 [SMILES: O=C1Nc2ccc(Cl)c(F)c2[C@]2(CCN(c3cc(C(=O)O)ncn3)C2)O1] | (S)-6-(6-Chloro-5-fluoro-2-oxo-1,2-dihydrospiro[benzo[d][1,3]oxazine-4,3'-pyrrolidin]-1'-yl)pyrimidine-4-carboxylic acid | Calcd. 379.1, found 378.9 |
| i-12 | 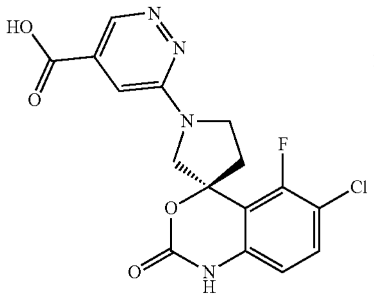 [SMILES: O=C1Nc2ccc(Cl)c(F)c2[C@]2(CCN(c3cc(C(=O)O)cnn3)C2)O1] | (S)-6-(6-Chloro-5-fluoro-2-oxo-1,2-dihydrospiro[benzo[d][1,3]oxazine-4,3'-pyrrolidin]-1'-yl)pyridazine-4-carboxylic acid | Calcd. 379.1, found 379.1 |

Intermediate i-13

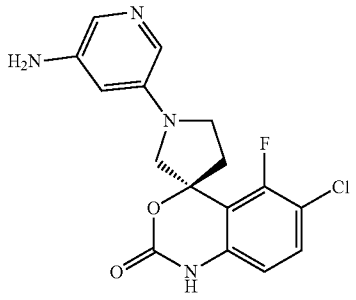

(S)-1'-(5-Aminopyridin-3-yl)-6-chloro-5-fluorospiro[benzo[d][1,3]oxazine-4,3'-pyrrolidin]-2(1H)-one 1,4-Dioxane (1.0 mL) was added to a mixture of methanesulfonato(2-dicyclohexylphosphino-2',6'-di-i-propoxy-1,1'-biphenyl)(2'-amino-1,1'-biphenyl-2-yl)palladium(II) (11 mg, 0.013 mmol), sodium tert-butoxide (52 mg, 0.54 mmol), (S)-6-chloro-5-fluorospiro[benzo[d][1,3]oxazine-4,3'-pyrrolidin]-2(1H)-one 2,2,2-trifluoroacetate (75 mg, 0.20 mmol), and tert-butyl (5-bromopyridin-3-yl)(tert-butoxycarbonyl)carbamate (50 mg, 0.13 mmol), and the resulting mixture was stirred at 100° C. for 8 h. The reaction was cooled to rt and concentrated to afford a residue that was diluted with TFA (0.5 mL) and allowed to stir at rt for 2 h. Concentration afforded a crude residue that was purified by reversed-phase preparatory-HPLC (C18 stationary phase, ACN/water+0.1% TFA) to yield the title compound. LCMS [M+H]$^+$=349.0 (calcd. 349.1).

Intermediate i-14

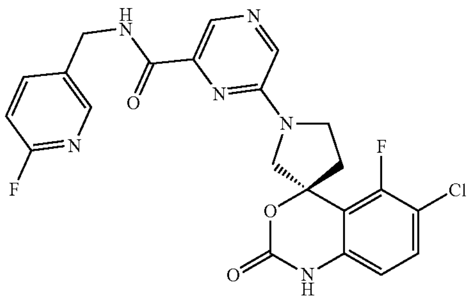

(S)-6-(6-Chloro-5-fluoro-2-oxo-1,2-dihydrospiro[benzo[d][1,3]oxazine-4,3'-pyrrolidin]-1'-yl)-N-((6-fluoropyridin-3-yl)methyl)pyrazine-2-carboxamide To a solution of (S)-6-(6-chloro-5-fluoro-2-oxo-1,2-dihydrospiro[benzo[d][1,3]oxazine-4,3'-pyrrolidin]-1'-yl)pyrazine-2-carboxylic acid (200 mg, 0.406 mmol) in DMF (4 mL) was added (6-fluoropyridin-3-yl)methanamine (102 mg, 0.812 mmol) and DIEA (350 µl, 2.03 mmol). The mixture was sonicated to dissolve the solids, HATU (30 mg, 0.079 mmol) was added, and the reaction was stirred at rt for 1 h. Satd. aq. $NH_4Cl$ was added, and the resulting suspension was filtered. The solid filter cake was washed with water, and dried to afford the title compound as a crude product that was carried on without further purification. LCMS [M+H]$^+$=487.1 (calcd. 487.1).

Intermediate Table 4. The following compounds were prepared using procedures similar to those described for Intermediate i-14 using the appropriate starting materials.

| Intermediate | Structure | Name | LCMS [M + H]+ |
|---|---|---|---|
| i-15 | 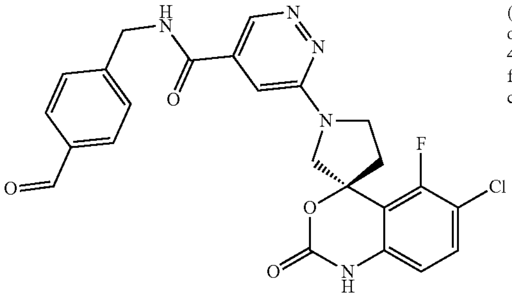 | (S)-6-(6-Chloro-5-fluoro-2-oxo-1,2-dihydrospiro[benzo[d][1,3]oxazine-4,3'-pyrrolidin]-1'-yl)-N-(4-formylbenzyl)pyridazine-4-carboxamide | Calcd. 496.1, found 496.0 |
| i-16 | 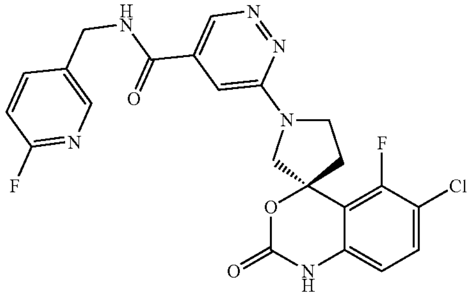 [SMILES: O=C1Nc2ccc(Cl)c(F)c2[C@]2(CCN(c3cc(C(=O)NCc4ccc(F)nc4)cnn3)C2)O1] | (S)-6-(6-Chloro-5-fluoro-2-oxo-1,2-dihydrospiro[benzo[d][1,3]oxazine-4,3'-pyrrolidin]-1'-yl)-N-((6-fluoropyridin-3-yl)methyl)pyridazine-4-carboxamide | Calcd. 487.1, found 487.1 |

Intermediate i-17

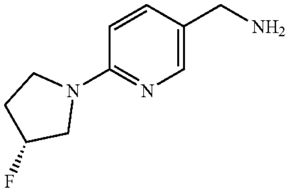

(R)-(6-(3-Fluoropyrrolidin-1-yl)pyridin-3-yl)methanamine

To a mixture containing tert-butyl ((6-bromopyridin-3-yl) methyl)carbamate (100 mg, 0.348 mmol), $Cs_2CO_3$ (113 mg, 0.348 mmol), $Pd_2(dba)_3$ (319 mg, 0.348 mmol), BINAP (217 mg, 0.348 mmol), and 3-(trifluoromethyl)pyrrolidine (73 mg, 0.52 mmol) was added 1,4-dioxane (1 mL). The reaction vial was sealed and then placed into 100° C. preheated aluminum block and heated for 12 h. The reaction mixture was then cooled to ambient temperature, concentrated to dryness, and the crude material was purified by column chromatography (silica, EtOAc/hexanes) to yield the title compound. LCMS $[M+H]^+$=196.1 (calcd. 196.1).

Intermediate Table 5. The following compounds were prepared using procedures, similar to those described for Intermediate i-17 using the appropriate starting materials.

| Intermediate | Structure | Name | LCMS [M + H]+ |
|---|---|---|---|
| i-18 | 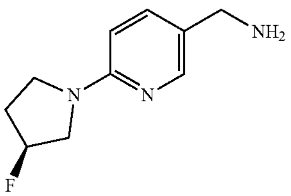 [SMILES: NCc1ccc(N2CC[C@H](F)C2)nc1] | (S)-(6-(3-Fluoropyrrolidin-1-yl)pyridin-3-yl)methanamine | Calcd. 196.1, found 196.1 |
| i-19 | 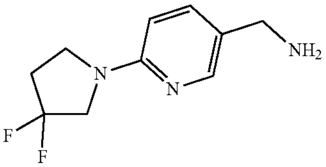 [SMILES: NCc1ccc(N2CCC(F)(F)C2)nc1] | (6-(3,3-Difluoropyrrolidin-1-yl)pyridin-3-yl)methanamine | Calcd. 214.1, found 214.1 |

-continued

| Intermediate | Structure | Name | LCMS $[M + H]^+$ |
|---|---|---|---|
| i-20 | 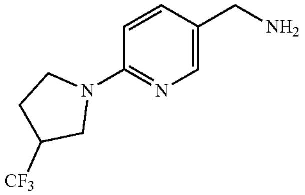 [SMILES: NCc1ccc(N2CCC(C(F)(F)F)C2)nc1] | (6-(3-(Trifluoromethyl)pyrrolidin-1-yl)pyridin-3-yl)methanamine | Calcd. 246.1, found 246.1 |

Intermediate i-21

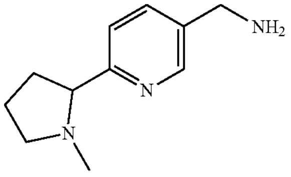

(6-(1-Methylpyrrolidin-2-yl)pyridin-3-yl)methanamine

Step 1: 6-(Pyrrolidin-2-yl)nicotinonitrile 2,2,2-trifluoroacetate. A mixture containing (tert-Butoxycarbonyl)proline (466 mg, 2.17 mmol), 6-chloronicotinonitrile (150 mg, 1.08 mmol), [4,4'-Bis(1,1-dimethylethyl)-2,2'-bipyridine-$N^1$,$N^{1'}$] bis[3,6-difluoro-2-[5-(trifluoromethyl)-2-pyridinyl-N]phenyl-C]Iridium(III) hexafluorophosphate (12 mg, 11 μmol) was purged with $N_2$, and DMF (1 mL) was added. The reaction vessel was placed into a photoreactor and irradiated for 2 h. The resulting mixture was then poured into 1 M LiCl and extracted with EtOAc. The combined organic phases were washed with water and brine, dried over $Na_2SO_4$, and concentrated to afford a crude residue that was purified by column chromatography on silica gel (0-50% EtOAc/hexanes). The resulting intermediate product was treated with TFA (1.0 mL) at rt for 10 min and concentrated to afford the title compound. LCMS $[M+H]^+$=174.1 (calc'd 174.1)

Step 2: (4-(1-Methylpyrrolidin-2-yl)phenyl)nicotinonitrile. To a solution of 6-(pyrrolidin-2-yl)nicotinonitrile 2,2,2-trifluoroacetate (375 mg, 1.31 mmol), formaldehyde (110 μl, 1.44 mmol), and DIEA (680 μl, 3.92 mmol) in DMF (1 mL) was added sodium triacetoxyborohydride (553 mg, 2.61 mmol). The reaction mixture was stirred overnight at rt. The reaction mixture was poured into 1M LiCl and adjusted to pH 10 with 1 M NaOH. The mixture was extracted with DCM, and the combined organics were dried over $Na_2SO_4$, and concentrated to afford a crude product that was carried on without further purification. LCMS $[M+H]^+$=188.1 (calc'd 188.1)

Step 3: (6-(1-Methylpyrrolidin-2-yl)pyridin-3-yl)methanamine. To a cold solution of LAH (30 mg, 0.80 mmol) in THF (2.7 mL) was added 6-(1-methylpyrrolidin-2-yl)nicotinonitrile (50 mg, 0.267 mmol). The resulting mixture was stirred at 0° C. and allowed to warm to rt and then stirred overnight. Once starting material was consumed, the mixture was chilled to 0° C. and quenched with water. DCM and 40% aqueous Rochelle's salt was then added, and the mixture was extracted with DCM. The combined organics were dried over $Na_2SO_4$, passed through Celite®, and concentrated to give a final product. LCMS $[M+H]^+$=192.1 (calcd. 192.1). Intermediate Table 6. The following compounds were prepared using procedures similar to those described for Intermediate i-21 using the appropriate starting materials.

| Intermediate | Structure | Name | LCMS $[M + H]^+$ |
|---|---|---|---|
| i-22 | 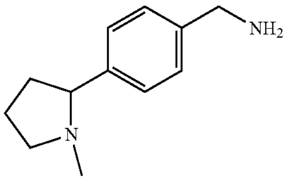 | (4-(1-Methylpyrrolidin-2-yl)phenyl)methanamine | Calcd. 191.2, found 190.1 |
| i-23 | 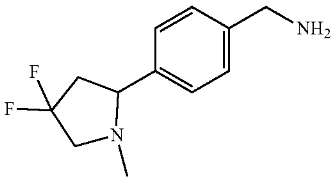 [SMILES: CN1CC(F)(F)CC1c1ccc(CN)cc1] | (4-(4,4-Difluoro-1-methylpyrrolidin-2-yl)phenyl)methanamine | Calcd. 227.1, found 226.1 |

-continued

| Intermediate | Structure | Name | LCMS [M + H]$^+$ |
|---|---|---|---|
| i-24 | 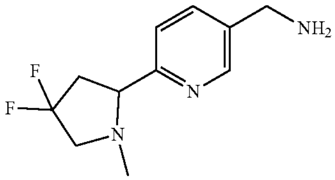 [SMILES: CN1CC(F)(F)CC1c1ccc(CN)cn1] | (6-(4,4-Difluoro-1-methylpyrrolidin-2-yl)pyridin-3-yl)methanamine | Calcd. 228.1, found 228.1 |

Intermediate i-25

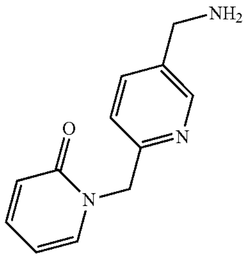

1-((5-(Aminomethyl)pyridin-2-yl)methyl)pyridin-2(2H)-one

Step 1: tert-Butyl (tert-butoxycarbonyl)((6-((2-oxopyridin-1(2H)-yl)methyl)pyridin-3-yl)methyl)carbamate: DMF (1 mL) was added to a mixture containing 1-((5-(chloromethyl)pyridin-2-yl)methyl)pyridin-2(1H)-one (0.023 g, 0.1 mmol) and di-tert-butyl iminodicarboxylate (24 mg, 0.11 mmol). Cesium carbonate (65 mg, 0.20 mmol) was then added in one portion. The resulting mixture was stirred at 40° C. for 1 h, evaporated, and the resulting residue was dissolved in water and extracted with EtOAc. The combined organics were washed with brine, dried over $Na_2SO_4$, and concentrated to dryness to give the title compound. LCMS $[M+H]^+$=416.1 (calc'd 416.2)

Step 2: 1-((5-(Aminomethyl)pyridin-2-yl)methyl)pyridin-2(1H)-one. tert-Butyl (tert-butoxycarbonyl)((6-((2-oxopyridin-1(2H)-yl)methyl)pyridin-3-yl)methyl)carbamate (42 mg, 0.10 mmol) was dissolved in TFA (100 µl, 1.30 mmol). The reaction mixture was stirred at rt for 30 min. The reaction was concentrated to give the title compound that was carried on without further purification. LCMS $[M+H]^+$ =216.1 (calcd. 216.1).

Intermediate Table 7. The following compounds were prepared using procedures similar to those described for Intermediate i-25 using the appropriate starting materials.

| Intermediate | Structure | Name | LCMS [M + H]$^+$ |
|---|---|---|---|
| i-26 | 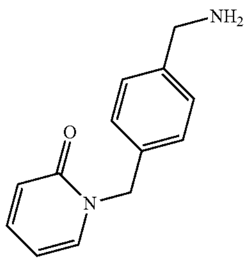 [SMILES: NCc1ccc(Cn2ccccc2=O)cc1] | 1-(4-(Aminomethyl)benzyl)pyridin-2(1H)-one | Calcd. 215.1, found 215.1 |
| i-27 | 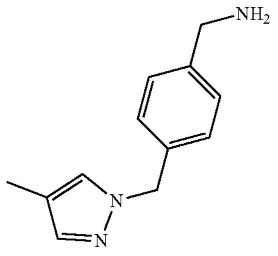 | (4-((4-Methyl-1H-pyrazol-1-yl)methyl)phenyl)methanamine | Calcd. 202.1, found 202.1 |

-continued

| Intermediate | Structure | Name | LCMS $[M + H]^+$ |
|---|---|---|---|
| i-28 | 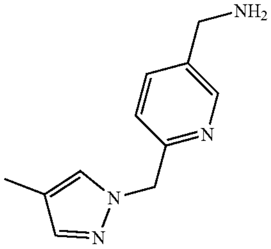 | (6-((4-Methyl-1H-pyrazol-1-yl)methyl)pyridin-3-yl)methanamine | Calcd. 203.1, found 203.1 |

Intermediate i-29

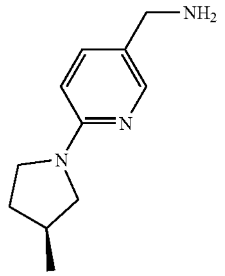

(S)-(6-(3-methylpyrrolidin-1-yl)pyridin-3-yl)methanamine

Step 1: tert-Butyl (S)-((6-(3-methylpyrrolidin-1-yl)pyridin-3-yl)methyl)carbamate: tert-Butyl ((6-fluoropyridin-3-yl)methyl)carbamate (527 mg, 2.33 mmol) and (S)-3-methylpyrrolidine hydrochloride (290 mg, 2.39 mmol) were mixed with DIEA (1.2 mL, 7.0 mmol), and the resulting mixture was then stirred overnight at 100 C for 8 h. The reaction mixture was then cooled to rt, filtered, and purified by reversed-phase preparatory-HPLC (C18 stationary phase, ACN/water+0.1% TFA) to afford the title compound. LCMS $[M+H]^+$=292.2 (calc'd 291.2)

Step 2: (S)-(6-(3-Methylpyrrolidin-1-yl)pyridin-3-yl)methanamine (S)-tert-Butyl ((6-(3-methylpyrrolidin-1-yl)pyridin-3-yl)methyl)carbamate (268 mg, 0.920 mmol) was mixed with TFA (710 μl, 9.20 mmol) and the reaction was stirred at rt for 30 min. The reaction was concentrated to afford the title compound that was carried on without further purification. LCMS $[M+H]^+$=192.1 (calcd. 192.1).

Intermediate i-30

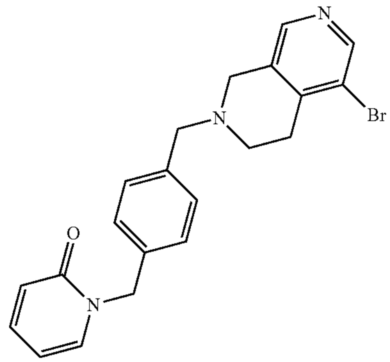

1-(4-((5-Bromo-3,4-dihydro-2,7-naphthyridin-2(1H)-yl)methyl)benzyl)pyridin-2(1H)-one DMF (3.5 mL) was added to a mixture of 5-bromo-1,2,3,4-tetrahydro-2,7-naphthyridine (70 mg, 0.33 mmol), 1-(4-(bromomethyl)benzyl)pyridin-2(1H)-one (83 mg, 0.30 mmol) and potassium carbonate (82 mg, 0.60 mmol), and the resulting mixture was stirred at 40° C. overnight. The reaction was cooled to rt, water was added, and the mixture was extracted with DCM. The combined organics were washed with brine, dried over $Na_2SO_4$, and concentrated to afford a crude residue that was purified by column chromatography on (silica; DCM/hexanes/MeOH). LCMS $[M+H]^+$= 410.0 (Calcd. 410.1)

Example 1

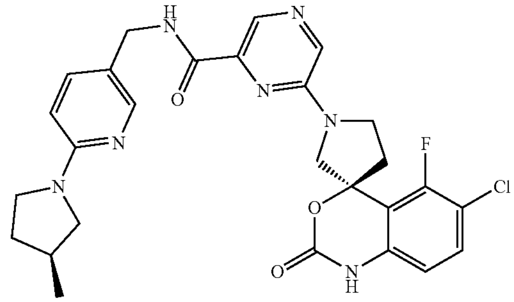 [SMILES: C[C@H]1CCN(c2ccc(CNC(=O)c3cncc(N4CC[C@]5(C4)OC(=O)Nc4ccc(Cl)c(F)c45)n3)cn2)C1]

(S)-6-(6-Chloro-5-fluoro-2-oxo-1,2-dihydrospiro[benzo[d][1,3]oxazine-4,3'-pyrrolidin]-1'-yl)-N-((6-((S)-3-methylpyrrolidin-1-yl)pyridin-3-yl)methyl)pyrazine-2-carboxamide DIEA (41 μL, 0.23 mmol) was added to a mixture of (S)-6-(6-chloro-5-fluoro-2-oxo-1,2-dihydrospiro[benzo[d][1,3]oxazine-4,3'-pyrrolidin]-1'-yl)pyrazine-2-carboxylic acid (23 mg, 0.047 mmol) and (S)-(6-(3-methylpyrrolidin-1-yl)pyridin-3-yl)methanamine 2,2,2-trifluoroacetate (17 mg, 0.056 mmol) in DMF (0.5 mL). HATU (30 mg, 0.079 mmol) was added in one portion, and the reaction was stirred at rt overnight. The crude reaction mixture was diluted with DMSO, filtered and purified by reversed-phase preparatory-HPLC (C18 stationary phase, ACN/water+0.1% TFA) to yield the title compound. $^1H$ NMR (600 MHz, $CD_3OD$) δ 8.46 (s, 1H), 8.27 (s, 1H), 8.02 (d, J=9.4 Hz, 1H), 7.84 (s, 1H), 7.51 (t, J=8.1 Hz, 1H), 7.08 (d, J=9.4 Hz, 1H), 6.82 (d, J=8.7 Hz, 1H), 4.51 (s, 2H), 4.34 (d, J=12.7 Hz, 1H), 4.17 (d, J=12.9 Hz, 1H), 4.03 (t, J=9.3 Hz, 1H), 3.91 (q, J=10.2

Hz, 1H), 3.73 (d, J=30.2 Hz, 2H), 3.57 (d, J=8.1 Hz, 1H), 3.13 (s, 1H), 2.92 (q, J=9.9 Hz, 1H), 2.72 (dd, J=13.4, 6.3 Hz, 1H), 2.55 (d, J=6.7 Hz, 1H), 2.29 (s, 1H), 1.79 (p, J=8.9 Hz, 1H), 1.20 (d, J=6.6 Hz, 3H). LCMS $[M+H]^+$=552.0 (calcd. 552.2).

Example 2

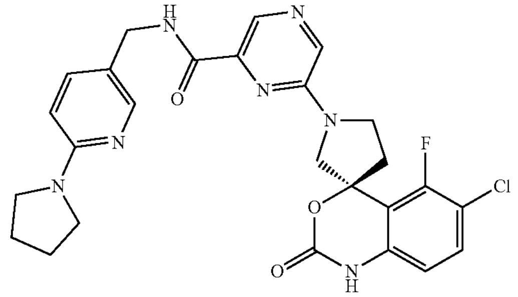 [SMILES: O=C1Nc2ccc(Cl)c(F)c2[C@]2(CCN(c3cncc(C(=O)NCc4ccc(N5CCCC5)nc4)n3)C2)O1]

(S)-6-(6-Chloro-5-fluoro-2-oxo-1,2-dihydrospiro[benzo[d][1,3]oxazine-4,3'-pyrrolidin]-1'-yl)-N-((6-(pyrrolidin-1-yl)pyridin-3-yl)methyl)pyrazine-2-carboxamide DIEA (180 μL, 1.03 mmol) was added to a mixture of azetidine (29 mg, 0.51 mmol) and (S)-6-(6-chloro-5-fluoro-2-oxo-1,2-dihydrospiro[benzo[d][1,3]oxazine-4,3'-pyrrolidin]-1'-yl)-N-((6-fluoropyridin-3-yl)methyl)pyrazine-2-carboxamide (50 mg, 0.10 mmol). The reaction was stirred at 115° C. overnight. The reaction was cooled to rt and purified by reversed-phase preparatory-HPLC (C18 stationary phase, ACN/water+0.1% TFA) to yield the title compound. $^1H$ NMR (600 MHz, $CD_3OD$) δ 8.55 (s, 1H), 8.48 (s, 1H), 8.15 (s, 1H), 8.05 (s, 1H), 7.60-7.50 (m, 1H), 7.50-7.40 (m, 1H), 6.80-6.70 (m, 1H), 6.50-6.40 (m, 1H) 4.50-4.40 (m, 2H), 2.35-2.25 (m, 1H), 4.10-4.00 (m, 1H), 4.00-3.90 (m, 1H), 3.90-3.80 (m, 1H), 3.45-3.35 (m, 1H), 3.20 (s, 1H), 2.95-2.85 (m, 1H), 2.7-2.6 (m, 1H). LCMS $[M+H]^+$=538.3 (calcd. 538.2).

The compounds below were prepared following procedures similar to those described for Examples 1 and 2 using appropriate starting materials.

| Intermediate | Structure | Name | LCMS $[M + H]^+$ |
|---|---|---|---|
| 3 | 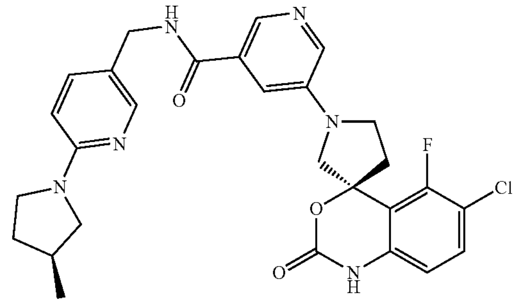 [SMILES: C[C@H]1CCN(c2ccc(CNC(=O)c3cncc(N4CC[C@]5(C4)OC(=O)Nc4ccc(Cl)c(F)c45)c3)cn2)C1] | (S)-5-(6-Chloro-5-fluoro-2-oxo-1,2-dihydrospiro[benzo[d][1,3]oxazine-4,3'-pyrrolidin]-1'-yl)-N-((6-((S)-3-methylpyrrolidin-1-yl)pyridin-3-yl)methyl)nicotinamide | Calcd. 551.2, Found 551.4 |
| 4 | 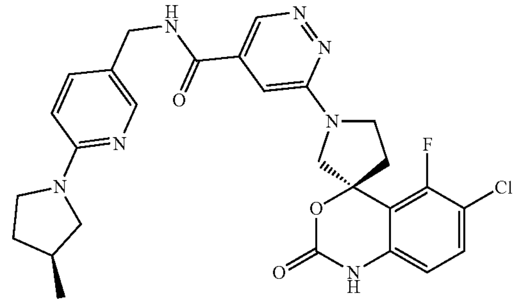 [SMILES: C[C@H]1CCN(c2ccc(CNC(=O)c3cnnc(N4CC[C@]5(C4)OC(=O)Nc4ccc(Cl)c(F)c45)c3)cn2)C1] | (S)-6-(6-Chloro-5-fluoro-2-oxo-1,2-dihydrospiro[benzo[d][1,3]oxazine-4,3'-pyrrolidin]-1'-yl)-N-((6-((S)-3-methylpyrrolidin-1-yl)pyridin-3-yl)methyl)pyridazine-4-carboxamide | Calcd. 552.2, Found 552.1 |
| 5 | 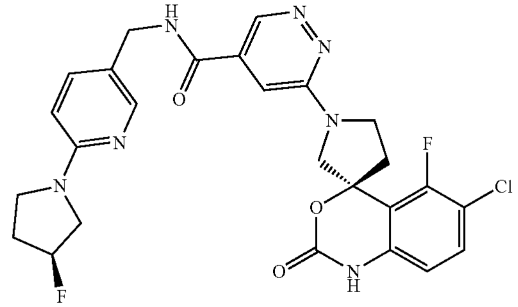 | (S)-6-(6-Chloro-5-fluoro-2-oxo-1,2-dihydrospiro[benzo[d][1,3]oxazine-4,3'-pyrrolidin]-1'-yl)-N-((6-((S)-3-fluoropyrrolidin-1-yl)pyridin-3-yl)methyl)pyridazine-4-carboxamide | Calcd. 556.2, Found 556.1 |

-continued

| Intermediate | Structure | Name | LCMS [M + H]+ |
|---|---|---|---|
| 6 | 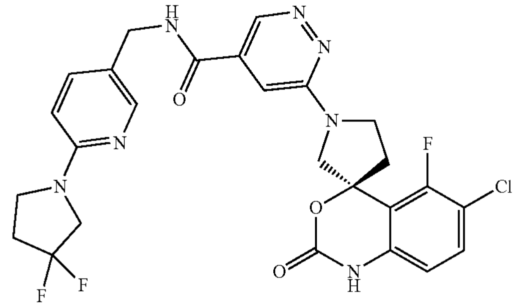 [SMILES: O=C1Nc2ccc(Cl)c(F)c2[C@]2(CCN(c3cc(C(=O)NCc4ccc(N5CCC(F)(F)C5)nc4)cnn3)C2)O1] | (S)-6-(6-Chloro-5-fluoro-2-oxo-1,2-dihydrospiro[benzo[d][1,3]oxazine-4,3'-pyrrolidin]-1'-yl)-N-((6-(3,3-difluoropyrrolidin-1-yl)pyridin-3-yl)methyl)pyridazine-4-carboxamide | Calcd. 574.2, Found 574.0 |
| 7 | 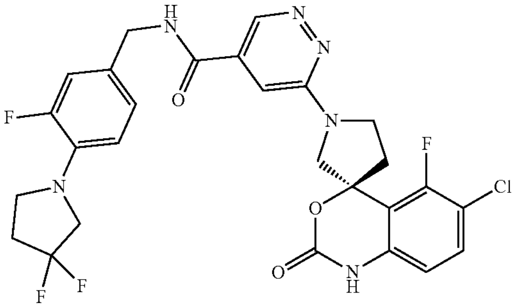 [SMILES: O=C1Nc2ccc(Cl)c(F)c2[C@]2(CCN(c3cc(C(=O)NCc4ccc(N5CCC(F)(F)C5)c(F)c4)cnn3)C2)O1] | (S)-6-(6-Chloro-5-fluoro-2-oxo-1,2-dihydrospiro[benzo[d][1,3]oxazine-4,3'-pyrrolidin]-1'-yl)-N-(4-(3,3-difluoropyrrolidin-1-yl)-3-fluorobenzyl)pyridazine-4-carboxamide | Calcd. 591.1, Found 591.0 |
| 8 | 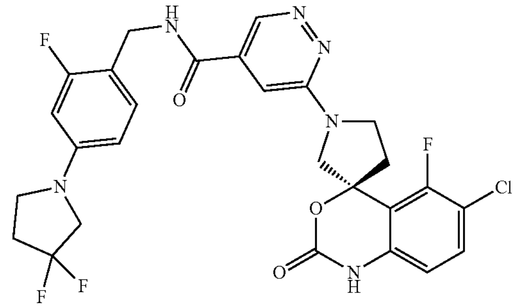 [SMILES: O=C1Nc2ccc(Cl)c(F)c2[C@]2(CCN(c3cc(C(=O)NCc4ccc(N5CCC(F)(F)C5)cc4F)cnn3)C2)O1] | (S)-6-(6-Chloro-5-fluoro-2-oxo-1,2-dihydrospiro[benzo[d][1,3]oxazine-4,3'-pyrrolidin]-1'-yl)-N-(4-(3,3-difluoropyrrolidin-1-yl)-2-fluorobenzyl)pyridazine-4-carboxamide | Calcd. 591.1, Found 591.1 |
| 9 | 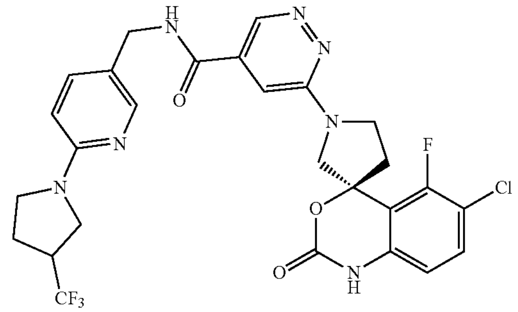 [SMILES: O=C1Nc2ccc(Cl)c(F)c2[C@]2(CCN(c3cc(C(=O)NCc4ccc(N5CCC(C(F)(F)F)C5)nc4)cnn3)C2)O1] | (S)-6-(6-Chloro-5-fluoro-2-oxo-1,2-dihydrospiro[benzo[d][1,3]oxazine-4,3'-pyrrolidin]-1'-yl)-N-((6-(3-(trifluoromethyl)pyrrolidin-1-yl)pyridin-3-yl)methyl)pyridazine-4-carboxamide | Calcd. 606.2, Found 606.1 |
| 10 | 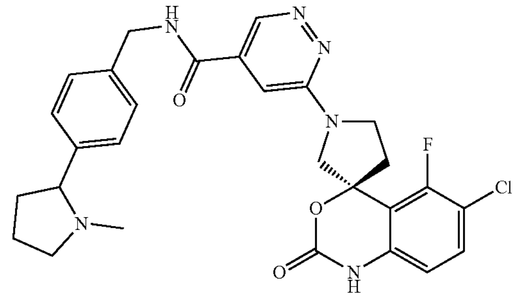 [SMILES: CN1CCCC1c1ccc(CNC(=O)c2cnnc(N3CC[C@]4(C3)OC(=O)Nc3ccc(Cl)c(F)c34)c2)cc1] | (S)-6-(6-Chloro-5-fluoro-2-oxo-1,2-dihydrospiro[benzo[d][1,3]oxazine-4,3'-pyrrolidin]-1'-yl)-N-(4-(1-methylpyrrolidin-2-yl)benzyl)pyridazine-4-carboxamide | Calcd. 551.2, Found 551.2 |

-continued

| Intermediate | Structure | Name | LCMS $[M + H]^+$ |
|---|---|---|---|
| 11 | 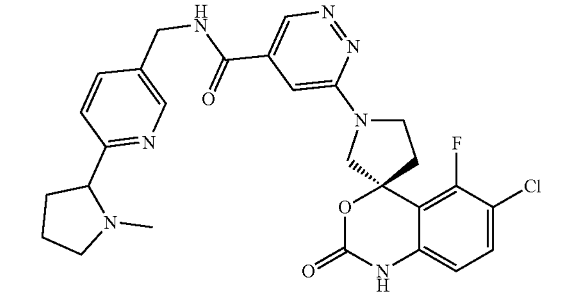 [SMILES: CN1CCCC1c1ccc(CNC(=O)c2cnnc(N3CC[C@]4(C3)OC(=O)Nc3ccc(Cl)c(F)c34)c2)cn1] | (S)-6-(6-Chloro-5-fluoro-2-oxo-1,2-dihydrospiro[benzo[d][1,3]oxazine-4,3'-pyrrolidin]-1'-yl)-N-((6-(1-methylpyrrolidin-2-yl)pyridin-3-yl)methyl)pyridazine-4-carboxamide | Calcd. 552.2, Found 552.4 |
| 12 | 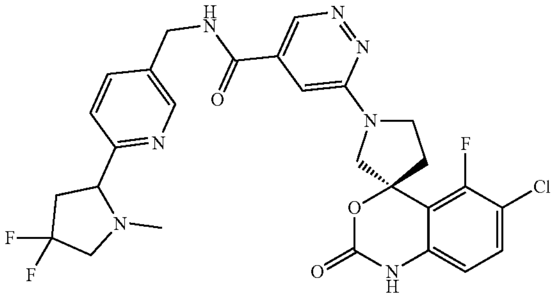 [SMILES: CN1CC(F)(F)CC1c1ccc(CNC(=O)c2cnnc(N3CC[C@]4(C3)OC(=O)Nc3ccc(Cl)c(F)c34)c2)cn1] | (S)-6-(6-Chloro-5-fluoro-2-oxo-1,2-dihydrospiro[benzo[d][1,3]oxazine-4,3'-pyrrolidin]-1'-yl)-N-(4-(4,4-difluoro-1-methylpyrrolidin-2-yl)benzyl)pyridazine-4-carboxamide | Calcd. 587.2, Found 587.1 |
| 13 | 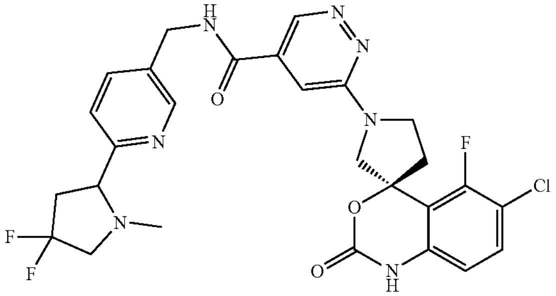 [SMILES: CN1CC(F)(F)CC1c1ccc(CNC(=O)c2cnnc(N3CC[C@]4(C3)OC(=O)Nc3ccc(Cl)c(F)c34)c2)cn1] | (S)-6-(6-Chloro-5-fluoro-2-oxo-1,2-dihydrospiro[benzo[d][1,3]oxazine-4,3'-pyrrolidin]-1'-yl)-N-((6-(4,4-difluoro-1-methylpyrrolidin-2-yl)pyridin-3-yl)methyl)pyridazine-4-carboxamide | Calcd. 588.2, Found 588.1 |
| 14 | 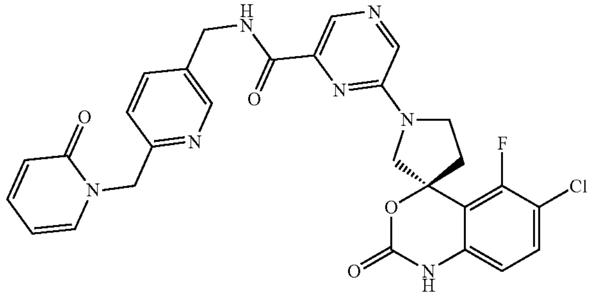 [SMILES: O=C1Nc2ccc(Cl)c(F)c2[C@]2(CCN(c3cncc(C(=O)NCc4ccc(Cn5ccccc5=O)nc4)n3)C2)O1] | (S)-6-(6-Chloro-5-fluoro-2-oxo-1,2-dihydrospiro[benzo[d][1,3]oxazine-4,3'-pyrrolidin]-1'-yl)-N-((6-((2-oxopyridin-1(2H)-yl)methyl)pyridin-3-yl)methyl)pyrazine-2-carboxamide | Calcd. 576.1, Found 576.1 |
| 15 | 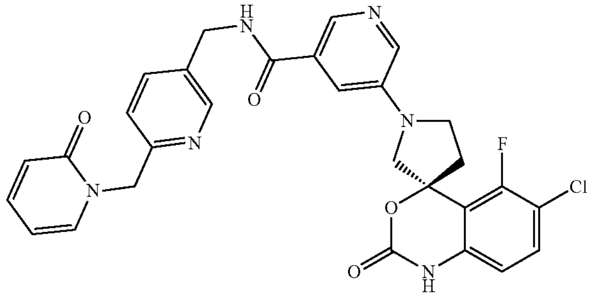 [SMILES: O=C1Nc2ccc(Cl)c(F)c2[C@]2(CCN(c3cncc(C(=O)NCc4ccc(Cn5ccccc5=O)nc4)c3)C2)O1] | (S)-5-(6-Chloro-5-fluoro-2-oxo-1,2-dihydrospiro[benzo[d][1,3]oxazine-4,3'-pyrrolidin]-1'-yl)-N-((6-((2-oxopyridin-1(2H)-yl)methyl)pyridin-3-yl)methyl)nicotinamide | Calcd. 575.2, Found 575.3 |

-continued

| Intermediate | Structure | Name | LCMS [M + H]+ |
|---|---|---|---|
| 16 | 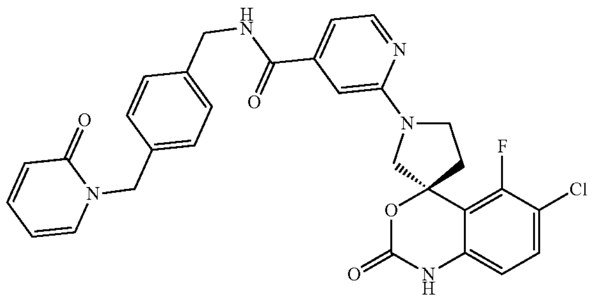 [SMILES: O=C1Nc2ccc(Cl)c(F)c2[C@]2(CCN(c3cc(C(=O)NCc4ccc(Cn5ccccc5=O)cc4)ccn3)C2)O1] | (S)-2-(6-Chloro-5-fluoro-2-oxo-1,2-dihydrospiro[benzo[d][1,3]oxazine-4,3'-pyrrolidin]-1'-yl)-N-(4-((2-oxopyridin-1(2H)-yl)methyl)benzyl)isonicotinamide | Calcd. 574.2, Found 574.0 |
| 17 | 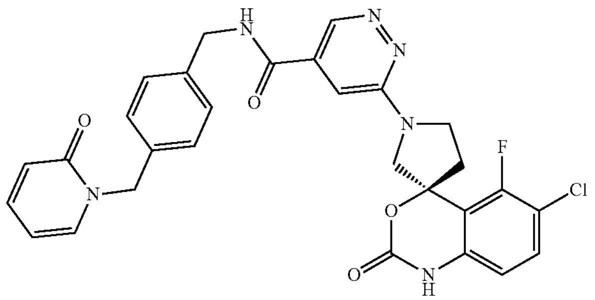 [SMILES: O=C1Nc2ccc(Cl)c(F)c2[C@]2(CCN(c3cc(C(=O)NCc4ccc(Cn5ccccc5=O)cc4)cnn3)C2)O1] | (S)-6-(6-Chloro-5-fluoro-2-oxo-1,2-dihydrospiro[benzo[d][1,3]oxazine-4,3'-pyrrolidin]-1'-yl)-N-(4-((2-oxopyridin-1(2H)-yl)methyl)benzyl)pyridazine-4-carboxamide | Calcd. 575.2, Found 575.4 |
| 18 | 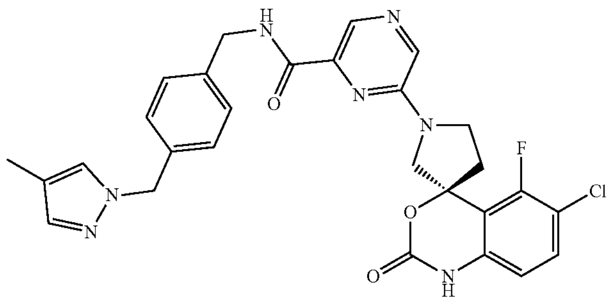 [SMILES: Cc1cnn(Cc2ccc(CNC(=O)c3cncc(N4CC[C@]5(C4)OC(=O)Nc4ccc(Cl)c(F)c45)n3)cc2)c1] | (S)-6-(6-Chloro-5-fluoro-2-oxo-1,2-dihydrospiro[benzo[d][1,3]oxazine-4,3'-pyrrolidin]-1'-yl)-N-(4-((4-methyl-1H-pyrazol-1-yl)methyl)benzyl)pyrazine-2-carboxamide | Calcd. 562.2, Found 562.1 |
| 19 | 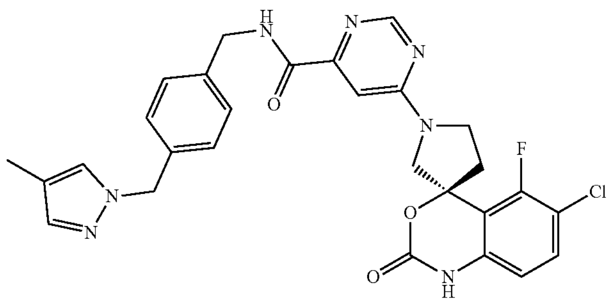 [SMILES: Cc1cnn(Cc2ccc(CNC(=O)c3cc(N4CC[C@]5(C4)OC(=O)Nc4ccc(Cl)c(F)c45)ncn3)cc2)c1] | (S)-6-(6-Chloro-5-fluoro-2-oxo-1,2-dihydrospiro[benzo[d][1,3]oxazine-4,3'-pyrrolidin]-1'-yl)-N-(4-((4-methyl-1H-pyrazol-1-yl)methyl)benzyl)pyrimidine-4-carboxamide | Calcd. 562.2, Found 562.5 |
| 20 | 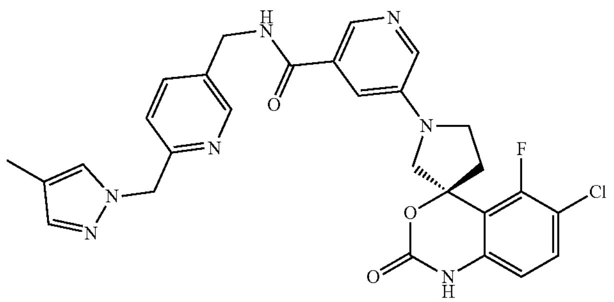 [SMILES: Cc1cnn(Cc2ccc(CNC(=O)c3cncc(N4CC[C@]5(C4)OC(=O)Nc4ccc(Cl)c(F)c45)c3)cn2)c1] | (S)-5-(6-Chloro-5-fluoro-2-oxo-1,2-dihydrospiro[benzo[d][1,3]oxazine-4,3'-pyrrolidin]-1'-yl)-N-((6-((4-methyl-1H-pyrazol-1-yl)methyl)pyridin-3-yl)methyl)nicotinamide | Calcd. 562.2, Found 562.3 |

-continued

| Intermediate | Structure | Name | LCMS [M + H]+ |
|---|---|---|---|
| 21 | 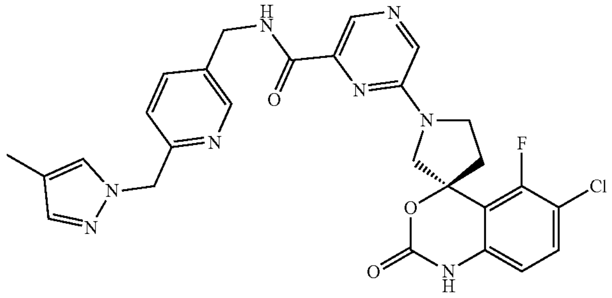 [SMILES: Cc1cnn(Cc2ccc(CNC(=O)c3cncc(N4CC[C@]5(C4)OC(=O)Nc4ccc(Cl)c(F)c45)n3)cn2)c1] | (S)-6-(6-Chloro-5-fluoro-2-oxo-1,2-dihydrospiro[benzo[d][1,3]oxazine-4,3'-pyrrolidin]-1'-yl)-N-((6-((4-methyl-1H-pyrazol-1-yl)methyl)pyridin-3-yl)methyl)pyrazine-2-carboxamide | Calcd. 563.2, Found 563.3 |
| 22 | 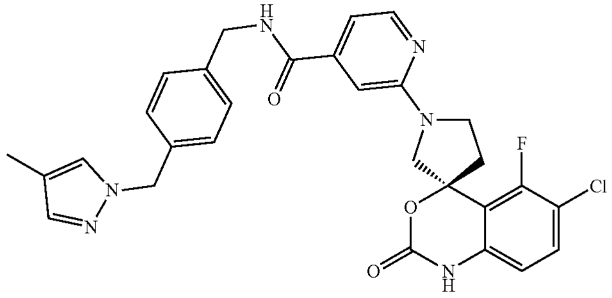 [SMILES: Cc1cnn(Cc2ccc(CNC(=O)c3ccnc(N4CC[C@]5(C4)OC(=O)Nc4ccc(Cl)c(F)c45)c3)cc2)c1] | (S)-2-(6-Chloro-5-fluoro-2-oxo-1,2-dihydrospiro[benzo[d][1,3]oxazine-4,3'-pyrrolidin]-1'-yl)-N-(4-((4-methyl-1H-pyrazol-1-yl)methyl)benzyl)isonicotinamide | Calcd. 561.2, Found 561.1 |
| 23 | 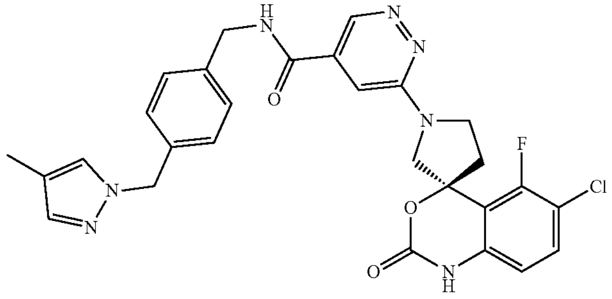 [SMILES: Cc1cnn(Cc2ccc(CNC(=O)c3cnnc(N4CC[C@]5(C4)OC(=O)Nc4ccc(Cl)c(F)c45)c3)cc2)c1] | (S)-6-(6-Chloro-5-fluoro-2-oxo-1,2-dihydrospiro[benzo[d][1,3]oxazine-4,3'-pyrrolidin]-1'-yl)-N-(4-((4-methyl-1H-pyrazol-1-yl)methyl)benzyl)pyridazine-4-carboxamide | Calcd. 562.2, Found 562.2 |
| 24 | 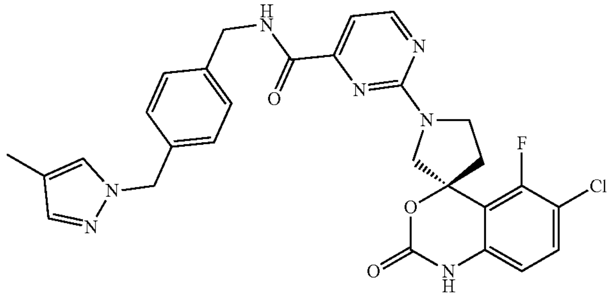 [SMILES: Cc1cnn(Cc2ccc(CNC(=O)c3ccnc(N4CC[C@]5(C4)OC(=O)Nc4ccc(Cl)c(F)c45)n3)cc2)c1] | (S)-2-(6-Chloro-5-fluoro-2-oxo-1,2-dihydrospiro[benzo[d][1,3]oxazine-4,3'-pyrrolidin]-1'-yl)-N-(4-((4-methyl-1H-pyrazol-1-yl)methyl)benzyl)pyrimidine-4-carboxamide | Calcd. 562.2, Found 562.0 |
| 25 | 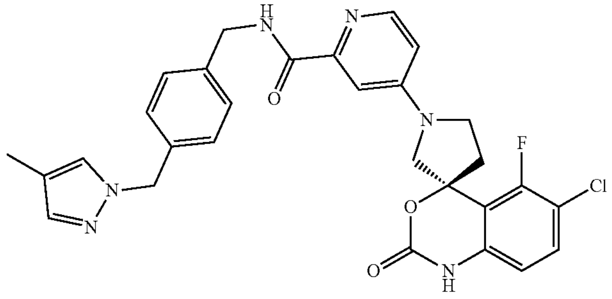 [SMILES: Cc1cnn(Cc2ccc(CNC(=O)c3cc(N4CC[C@]5(C4)OC(=O)Nc4ccc(Cl)c(F)c45)ccn3)cc2)c1] | (S)-4-(6-Chloro-5-fluoro-2-oxo-1,2-dihydrospiro[benzo[d][1,3]oxazine-4,3'-pyrrolidin]-1'-yl)-N-(4-((4-methyl-1H-pyrazol-1-yl)methyl)benzyl)picolinamide | Calcd. 561.2, Found 561.0 |

-continued

| Intermediate | Structure | Name | LCMS [M + H]+ |
|---|---|---|---|
| 26 | 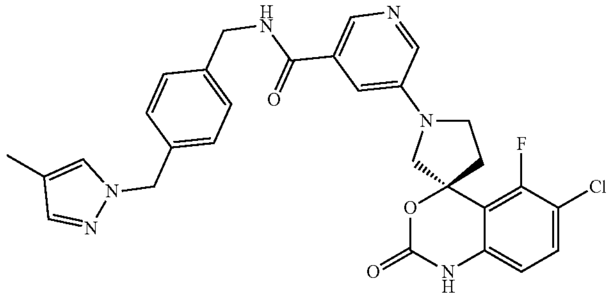 [SMILES: Cc1cnn(Cc2ccc(CNC(=O)c3cncc(N4CC[C@]5(C4)OC(=O)Nc4ccc(Cl)c(F)c45)c3)cc2)c1] | (S)-5-(6-Chloro-5-fluoro-2-oxo-1,2-dihydrospiro[benzo[d][1,3]oxazine-4,3'-pyrrolidin]-1'-yl)-N-(4-((4-methyl-1H-pyrazol-1-yl)methyl)benzyl)nicotinamide | Calcd. 561.2, Found 561.0 |
| 27 | 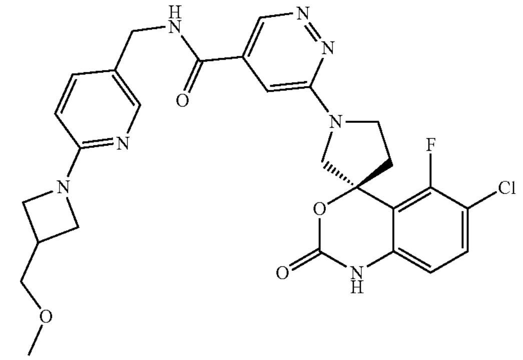 [SMILES: COCC1CN(c2ccc(CNC(=O)c3cnnc(N4CC[C@]5(C4)OC(=O)Nc4ccc(Cl)c(F)c45)c3)cn2)C1] | (S)-6-(6-Chloro-5-fluoro-2-oxo-1,2-dihydrospiro[benzo[d][1,3]oxazine-4,3'-pyrrolidin]-1'-yl)-N-((6-(3-(methoxymethyl)azetidin-1-yl)pyridin-3-yl)methyl)pyridazine-4-carboxamide | Calcd. 568.2, Found 568.3 |
| 28 | 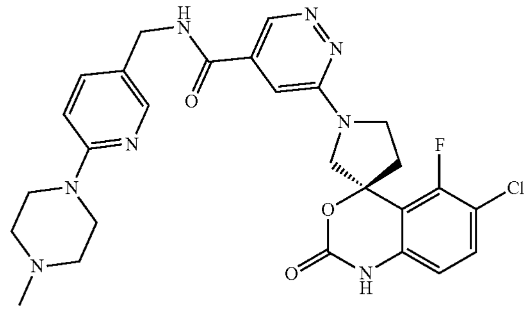 [SMILES: CN1CCN(c2ccc(CNC(=O)c3cnnc(N4CC[C@]5(C4)OC(=O)Nc4ccc(Cl)c(F)c45)c3)cn2)CC1] | (S)-6-(6-Chloro-5-fluoro-2-oxo-1,2-dihydrospiro[benzo[d][1,3]oxazine-4,3'-pyrrolidin]-1'-yl)-N-((6-(4-methylpiperazin-1-yl)pyridin-3-yl)methyl)pyridazine-4-carboxamide | Calcd. 567.20, Found 567.3 |
| 29 | 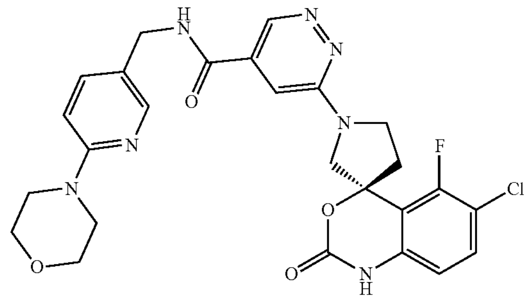 [SMILES: O=C1Nc2ccc(Cl)c(F)c2[C@]2(CCN(c3cc(C(=O)NCc4ccc(N5CCOCC5)nc4)cnn3)C2)O1] | (S)-6-(6-Chloro-5-fluoro-2-oxo-1,2-dihydrospiro[benzo[d][1,3]oxazine-4,3'-pyrrolidin]-1'-yl)-N-((6-morpholinopyridin-3-yl)methyl)pyridazine-4-carboxamide | Calcd. 554.2, Found 554.3 |
| 30 | 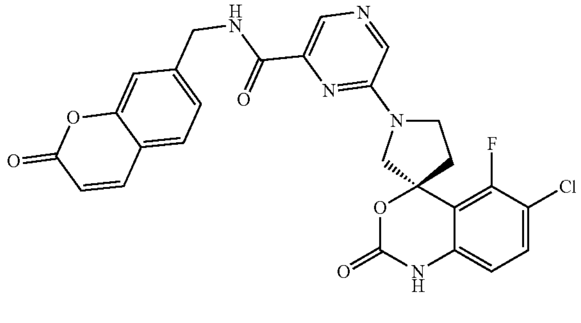 [SMILES: O=C1Nc2ccc(Cl)c(F)c2[C@]2(CCN(c3cncc(C(=O)NCc4ccc5ccc(=O)oc5c4)n3)C2)O1] | (S)-6-(6-Chloro-5-fluoro-2-oxo-1,2-dihydrospiro[benzo[d][1,3]oxazine-4,3'-pyrrolidin]-1'-yl)-N-((2-oxo-2H-chromen-7-yl)methyl)pyrazine-2-carboxamide | Calcd. 536.1, Found 536.0 |

-continued

| Intermediate | Structure | Name | LCMS [M + H]$^+$ |
|---|---|---|---|
| 31 | 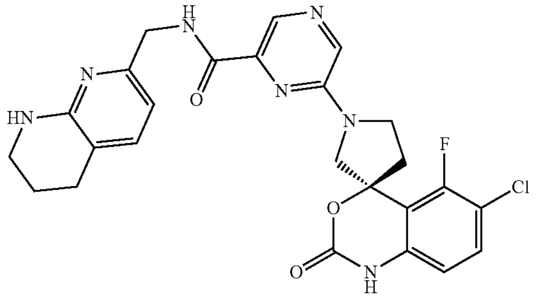 [SMILES: O=C1Nc2ccc(Cl)c(F)c2[C@]2(CCN(c3cncc(C(=O)NCc4ccc5c(n4)NCCC5)n3)C2)O1] | (S)-6-(6-Chloro-5-fluoro-2-oxo-1,2-dihydrospiro[benzo[d][1,3]oxazine-4,3'-pyrrolidin]-1'-yl)-N-((5,6,7,8-tetrahydro-1,8-naphthyridin-2-yl)methyl)pyrazine-2-carboxamide | Calcd. 524.2, Found 524.0 |
| 32 | 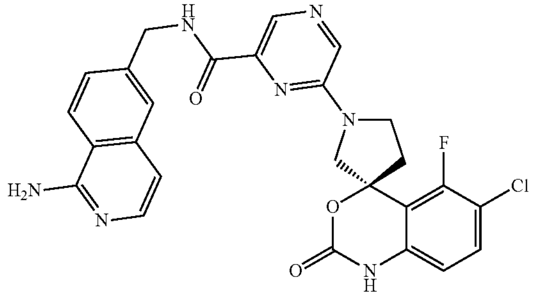 [SMILES: Nc1nccc2cc(CNC(=O)c3cncc(N4CC[C@]5(C4)OC(=O)Nc4ccc(Cl)c(F)c45)n3)ccc12] | (S)-N-((1-Aminoisoquinolin-6-yl)methyl)-6-(6-chloro-5-fluoro-2-oxo-1,2-dihydrospiro[benzo[d][1,3]oxazine-4,3'-pyrrolidin]-1'-yl)pyrazine-2-carboxamide | Calcd. 534.1, Found 534.0 |
| 33 | 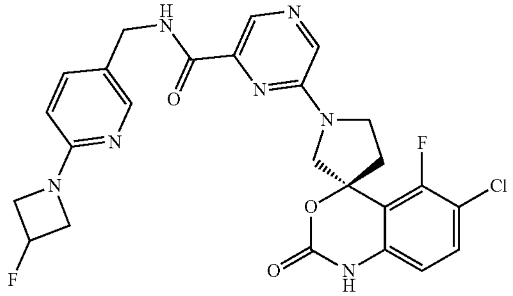 [SMILES: O=C1Nc2ccc(Cl)c(F)c2[C@]2(CCN(c3cncc(C(=O)NCc4ccc(N5CC(F)C5)nc4)n3)C2)O1] | (S)-6-(6-Chloro-5-fluoro-2-oxo-1,2-dihydrospiro[benzo[d][1,3]oxazine-4,3'-pyrrolidin]-1'-yl)-N-((6-(3-fluoroazetidin-1-yl)pyridin-3-yl)methyl)pyrazine-2-carboxamide | Calcd. 542.1, Found 542.3 |
| 34 | 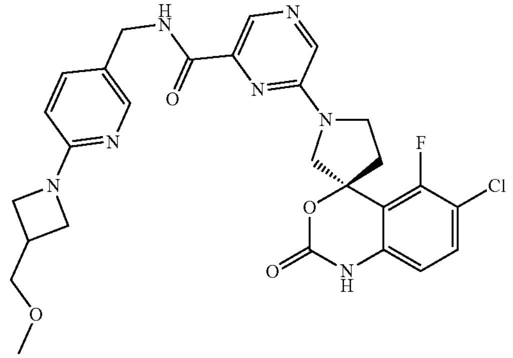 [SMILES: COCC1CN(c2ccc(CNC(=O)c3cncc(N4CC[C@]5(C4)OC(=O)Nc4ccc(Cl)c(F)c45)n3)cn2)C1] | (S)-6-(6-Chloro-5-fluoro-2-oxo-1,2-dihydrospiro[benzo[d][1,3]oxazine-4,3'-pyrrolidin]-1'-yl)-N-((6-(3-(methoxymethyl)azetidin-1-yl)pyridin-3-yl)methyl)pyrazine-2-carboxamide | Calcd. 568.2, Found 568.3 |

-continued

| Intermediate | Structure | Name | LCMS [M + H]+ |
|---|---|---|---|
| 35 | 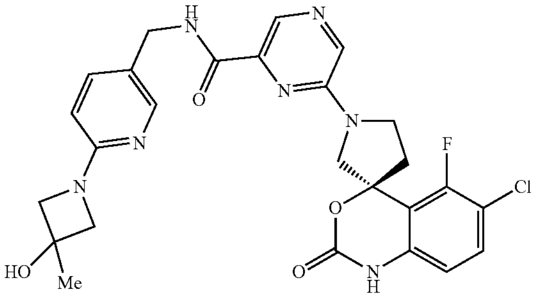 [SMILES: CC1(O)CN(c2ccc(CNC(=O)c3cncc(N4CC[C@]5(C4)OC(=O)Nc4ccc(Cl)c(F)c45)n3)cn2)C1] | (S)-6-(6-chloro-5-fluoro-2-oxo-1,2-dihydrospiro[benzo[d][1,3]oxazine-4,3'-pyrrolidin]-1'-yl)-N-((6-(3-hydroxy-3-methylazetidin-1-yl)pyridin-3-yl)methyl)pyrazine-2-carboxamide | Calcd. 568.2, Found 568.3 |
| 36 | 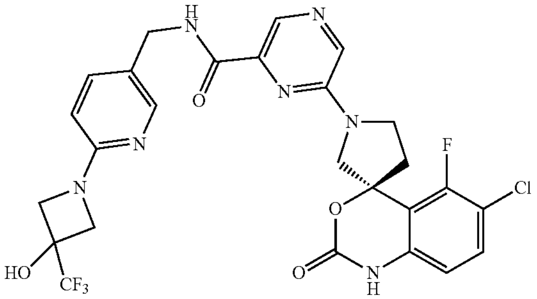 [SMILES: O=C1Nc2ccc(Cl)c(F)c2[C@]2(CCN(c3cncc(C(=O)NCc4ccc(N5CC(O)(C(F)(F)F)C5)nc4)n3)C2)O1] | (S)-6-(6-Chloro-5-fluoro-2-oxo-1,2-dihydrospiro[benzo[d][1,3]oxazine-4,3'-pyrrolidin]-1'-yl)-N-((6-(3-hydroxy-3-(trifluoromethyl)azetidin-1-yl)pyridin-3-yl)methyl)pyrazine-2-carboxamide | Calcd. 608.1, Found 608.2 |
| 37 | 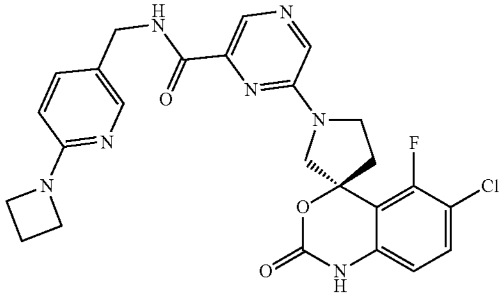 [SMILES: O=C1Nc2ccc(Cl)c(F)c2[C@]2(CCN(c3cncc(C(=O)NCc4ccc(N5CCC5)nc4)n3)C2)O1] | (S)-N-((6-(Azetidin-1-yl)pyridin-3-yl)methyl)-6-(6-chloro-5-fluoro-2-oxo-1,2dihydrospiro[benzo[d][1,3]oxazine-4,3'-pyrrolidin]-1'-yl)pyrazine-2-carboxamide | Calcd. 524.2, Found 524.0 |
| 38 | 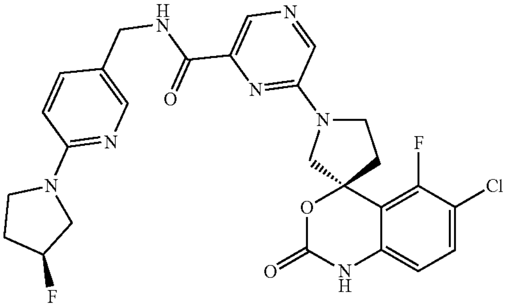 [SMILES: O=C1Nc2ccc(Cl)c(F)c2[C@]2(CCN(c3cncc(C(=O)NCc4ccc(N5CC[C@H](F)C5)nc4)n3)C2)O1] | (S)-6-(6-Chloro-5-fluoro-2-oxo-1,2-dihydrospiro[benzo[d][1,3]oxazine-4,3'-pyrrolidin]-1'-yl)-N-((6-((S)-3-fluoropyrrolidin-1-yl)pyridin-3-yl)methyl)pyrazine-2-carboxamide | Calcd. 556.2, Found 557.1 |
| 39 | 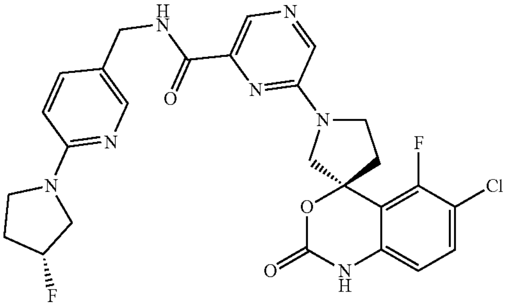 [SMILES: O=C1Nc2ccc(Cl)c(F)c2[C@]2(CCN(c3cncc(C(=O)NCc4ccc(N5CC[C@@H](F)C5)nc4)n3)C2)O1] | (S)-6-(6-Chloro-5-fluoro-2-oxo-1,2-dihydrospiro[benzo[d][1,3]oxazine-4,3'-pyrrolidin]-1'-yl)-N-((6-((R)-3-fluoropyrrolidin-1-yl)pyridin-3-yl)methyl)pyrazine-2-carboxamide | Calcd. 556.2, Found 556.3 |

-continued

| Intermediate | Structure | Name | LCMS [M + H]$^+$ |
|---|---|---|---|
| 40 | 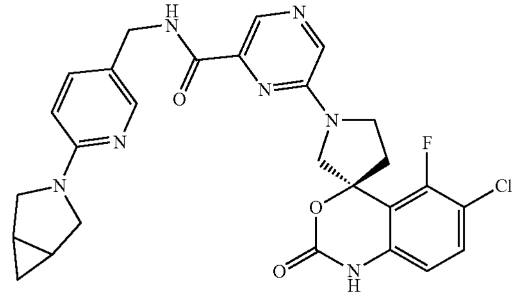 [SMILES: O=C1Nc2ccc(Cl)c(F)c2[C@]2(CCN(c3cncc(C(=O)NCc4ccc(N5CC6CC6C5)nc4)n3)C2)O1] | N-((6-(3-Azabicyclo[3.1.0]hexan-3-yl)pyridin-3-yl)methyl)-6-((S)-6-chloro-5-fluoro-2-oxo-1,2-dihydrospiro[benzo[d][1,3]oxazine-4,3'-pyrrolidin]-1'-yl)pyrazine-2-carboxamide | Calcd. 550.2, Found 550.4 |
| 41 | 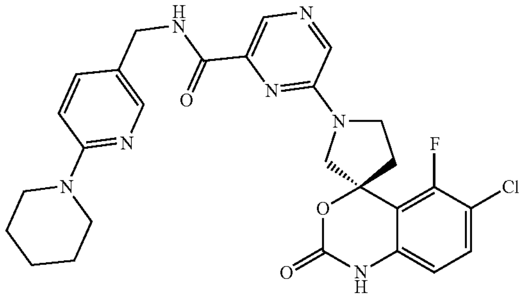 [SMILES: O=C1Nc2ccc(Cl)c(F)c2[C@]2(CCN(c3cncc(C(=O)NCc4ccc(N5CCCCC5)nc4)n3)C2)O1] | (S)-6-(6-Chloro-5-fluoro-2-oxo-1,2-dihydrospiro[benzo[d][1,3]oxazine-4,3'-pyrrolidin]-1'-yl)-N-((6-(piperidin-1-yl)pyridin-3-yl)methyl)pyrazine-2-carboxamide | Calcd. 552.2, Found 552.3 |
| 42 | 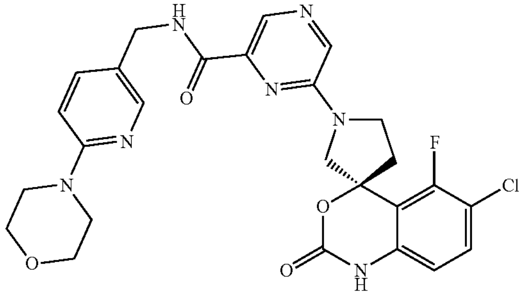 [SMILES: O=C1Nc2ccc(Cl)c(F)c2[C@]2(CCN(c3cncc(C(=O)NCc4ccc(N5CCOCC5)nc4)n3)C2)O1] | (S)-6-(6-Chloro-5-fluoro-2-oxo-1,2-dihydrospiro[benzo[d][1,3]oxazine-4,3'-pyrrolidin]-1'-yl)-N-((6-morpholinopyridin-3-yl)methyl)pyrazine-2-carboxamide | Calcd. 554.2, Found 554.3 |
| 43 | 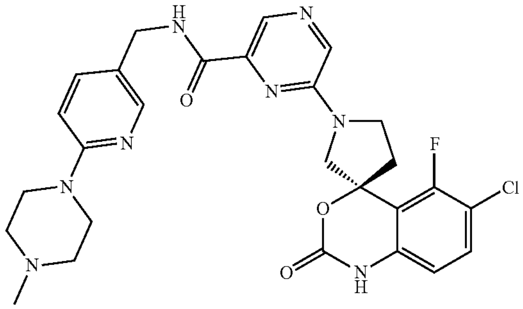 [SMILES: CN1CCN(c2ccc(CNC(=O)c3cncc(N4CC[C@]5(C4)OC(=O)Nc4ccc(Cl)c(F)c45)n3)cn2)CC1] | (S)-6-(6-Chloro-5-fluoro-2-oxo-1,2-dihydrospiro[benzo[d][1,3]oxazine-4,3'-pyrrolidin]-1'-yl)-N-((6-(4-methylpiperazin-1-yl)pyridin-3-yl)methyl)pyrazine-2-carboxamide | Calcd. 567.2, Found 567.4 |

Example 44

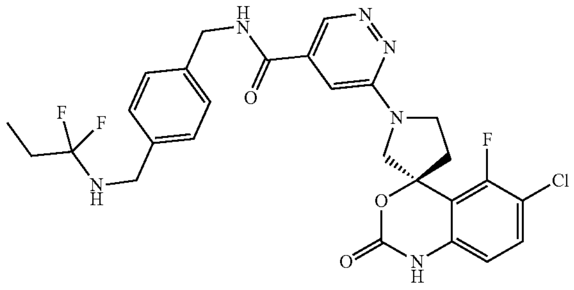 [SMILES: CCC(F)(F)NCc1ccc(CNC(=O)c2cnnc(N3CC[C@]4(C3)OC(=O)Nc3ccc(Cl)c(F)c34)c2)cc1]

(S)-6-(6-Chloro-5-fluoro-2-oxo-1,2-dihydrospiro[benzo[d][1,3]oxazine-4,3'-pyrrolidin]-1'-yl)-N-(4-(((1,1-difluoropropyl)amino)methyl)benzyl)pyridazine-4-carboxamide DCE (1 mL) was added to a mixture of (S)-6-(6-chloro-5-fluoro-2-oxo-1,2-dihydrospiro[benzo[d][1,3]oxazine-4,3'-pyrrolidin]-1'-yl)-N-(4-formylbenzyl)pyridazine-4-carboxamide (30 mg, 0.060 mmol) and 1,1-difluoropropan-1-amine (12 mg, 0.12 mmol). Sodium triacetoxyborohydride (51 mg, 0.24 mmol)) was added in one portion, and the resulting mixture was stirred at rt for 3 h. The reaction mixture was diluted with MeOH and concentrated to afford a crude residue that was purified by reversed-phase preparatory-HPLC (C18 stationary phase, ACN/water+0.1% TFA) to yield the title compound. $^1$H NMR (400 MHz, $CD_3OD$) δ 10.98 (s, 1H), 9.47 (t, J=5 Hz, 1H), 8.87 (s, 1H), 7.58-7.56 (m, 2H), 7.48-7.46 (m, 3H), 7.45-7.39 (m, 3H), 6.84-6.84 (m, 2H), 4.50 (d, J=10 Hz, 2H), 4.34 (s, 1H), 4.1 (s, 3H), 4.03 (d, J=15 Hz, 1H), 2.78-2.62 (m, 2H), 1.71 (t, J=20 Hz, 3H). LCMS $[M+H]^+$=575.1 (calcd. 575.2).

The compounds below were prepared following procedures similar to those described for Example 44 using appropriate starting materials.

| Example | Structure | Name | LCMS $[M + H]^+$ |
|---|---|---|---|
| 45 | 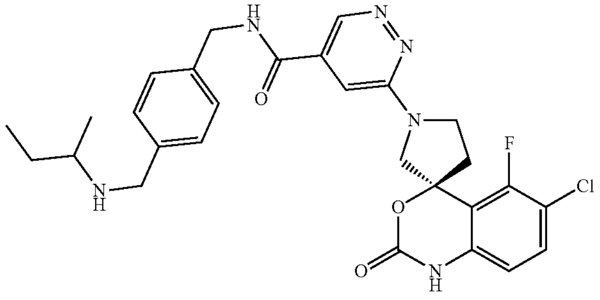 [SMILES: CCC(C)NCc1ccc(CNC(=O)c2cnnc(N3CC[C@]4(C3)OC(=O)Nc3ccc(Cl)c(F)c34)c2)cc1] | N-(4-((sec-Butylamino)methyl)benzyl)-6-((S)-6-chloro-5-fluoro-2-oxo-1,2-dihydrospiro[benzo[d][1,3]oxazine-4,3'-pyrrolidin]-1'-yl)pyridazine-4-carboxamide | Calcd. 553.2, Found 553.1 |
| 46 | 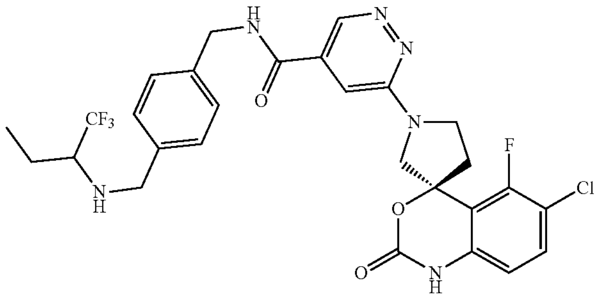 [SMILES: CCC(NCc1ccc(CNC(=O)c2cnnc(N3CC[C@]4(C3)OC(=O)Nc3ccc(Cl)c(F)c34)c2)cc1)C(F)(F)F] | (S)-6-(6-Chloro-5-fluoro-2-oxo-1,2-dihydrospiro[benzo[d][1,3]oxazine-4,3'-pyrrolidin]-1'-yl)-N-(4-(((1,1,1-trifluorobutan-2-yl)amino)methyl)benzyl)pyridazine-4-carboxamide | Calcd. 607.2, Found 608.0 |
| 47 | 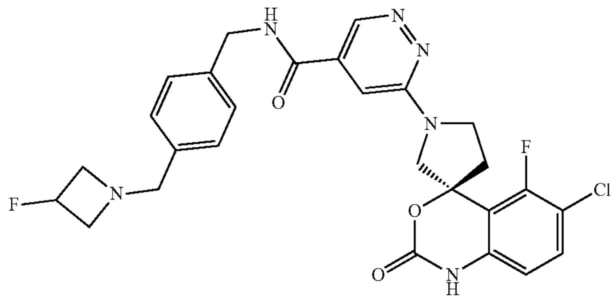 [SMILES: O=C1Nc2ccc(Cl)c(F)c2[C@]2(CCN(c3cc(C(=O)NCc4ccc(CN5CC(F)C5)cc4)cnn3)C2)O1] | (S)-6-(6-chloro-5-fluoro-2-oxo-1,2-dihydrospiro[benzo[d][1,3]oxazine-4,3'-pyrrolidin]-1'-yl)-N-(4-((3-fluoroazetidin-1-yl)methyl)benzyl)pyridazine-4-carboxamide | Calcd. 555.2, Found 555.0 |

-continued

| Example | Structure | Name | LCMS [M + H]+ |
|---|---|---|---|
| 48 | 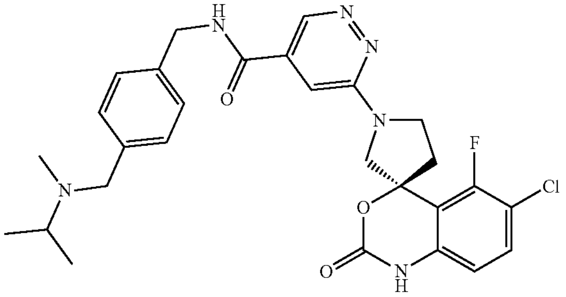 [SMILES: CC(C)N(C)Cc1ccc(CNC(=O)c2cnnc(N3CC[C@]4(C3)OC(=O)Nc3ccc(Cl)c(F)c34)c2)cc1] | (S)-6-(6-Chloro-5-fluoro-2-oxo-1,2-dihydrospiro[benzo[d][1,3]oxazine-4,3'-pyrrolidin]-1'-yl)-N-(4-((isopropyl(methyl)amino)methyl)benzyl)pyridazine-4-carboxamide | Calcd. 553.2, Found 553.0 |
| 49 | 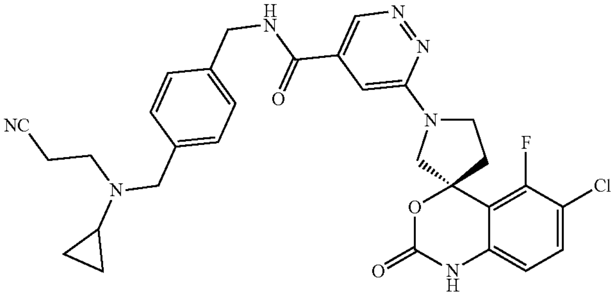 [SMILES: N#CCCN(Cc1ccc(CNC(=O)c2cnnc(N3CC[C@]4(C3)OC(=O)Nc3ccc(Cl)c(F)c34)c2)cc1)C1CC1] | (S)-6-(6-Chloro-5-fluoro-2-oxo-1,2-dihydrospiro[benzo[d][1,3]oxazine-4,3'-pyrrolidin]-1'-yl)-N-(4-(((2-cyanoethyl)(cyclopropyl)amino)methyl)benzyl)pyridazine-4-carboxamide | Calcd. 590.2, Found 590.1 |
| 50 | 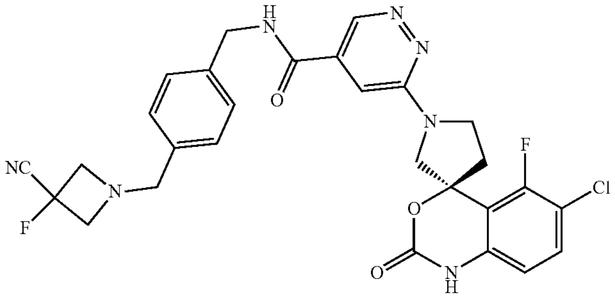 [SMILES: N#CC1(F)CN(Cc2ccc(CNC(=O)c3cnnc(N4CC[C@]5(C4)OC(=O)Nc4ccc(Cl)c(F)c45)c3)cc2)C1] | (S)-6-(6-Chloro-5-fluoro-2-oxo-1,2-dihydrospiro[benzo[d][1,3]oxazine-4,3'-pyrrolidin]-1'-yl)-N-(4-((3-cyano-3-fluoroazetidin-1-yl)methyl)benzyl)pyridazine-4-carboxamide | Calcd. 580.2, Found 580.1 |

Example 51

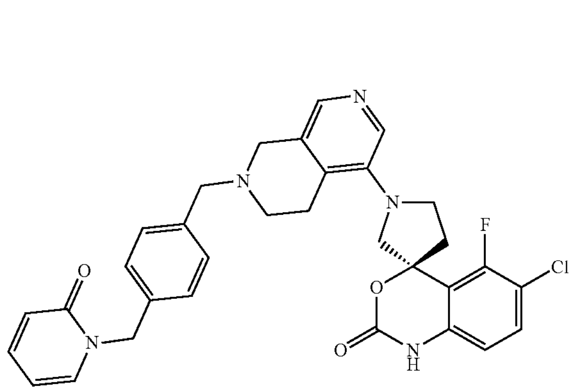 [SMILES: O=C1Nc2ccc(Cl)c(F)c2[C@]2(CCN(c3cncc4c3CCN(Cc3ccc(Cn5ccccc5=O)cc3)C4)C2)O1]

(S)-6-Chloro-5-fluoro-1'-(7-(4-((2-oxopyridin-1(2H)-yl)methyl)benzyl)-5,6,7,8-tetrahydro-2,7-naphthyridin-4-yl)spiro[benzo[d][1,3]oxazine-4,3'-pyrrolidin]-2(1H)-one DMA (0.7 mL) was added to a mixture of 1-(4-((5-bromo-3,4-dihydro-2,7-naphthyridin-2(1H)-yl)methyl)benzyl)pyridin-2(1H)-one (87 mg, 0.21 mmol), (S)-6-chloro-5-fluorospiro[benzo[d][1,3]oxazine-4,3'-pyrrolidin]-2(1H)-one 2,2,2-trifluoroacetate (79 mg, 0.21 mmol), (2-Dicyclohexylphosphino-2',6'-diisopropoxy-1,1'-biphenyl)[2-(2'-amino-1,1'-biphenyl]palladium(II) methanesulfonate (27 mg, 0.032 mmol), and sodium tert-butoxide (61 mg, 0.64 mmol). The resulting mixture was heated to 100° C. for 12 h. The reaction mixture was cooled to rt and purified by reversed-phase preparatory-HPLC (C18 stationary phase, ACN/water+0.1% TFA) to yield the title compound. $^1$H NMR (500 MHz, $d_6$-DMSO) δ 7.99 (s, 1H), 7.86 (s, 1H), 7.79 (d, J=6.6 Hz, 1H), 7.54 (t, J=8.2 Hz, 1H), 7.46-7.39 (m, 2H), 7.34 (d, J=7.9 Hz, 3H), 7.26 (d, J=8.2 Hz, 3H), 6.78 (d, J=8.5 Hz, 1H), 6.55 (s, 3H), 6.42 (d, J=8.8 Hz, 1H), 6.25 (t, J=6.3 Hz, 1H), 3.84 (d, J=11.2 Hz, 1H), 3.70 (d, J=14.4 Hz, 2H), 3.66-3.59 (m, 2H), 2.79 (s, 2H), 2.64 (d, J=4.8 Hz, 2H). LCMS $[M+H]^+$=586.0 (calcd. 586.2).

Example 52

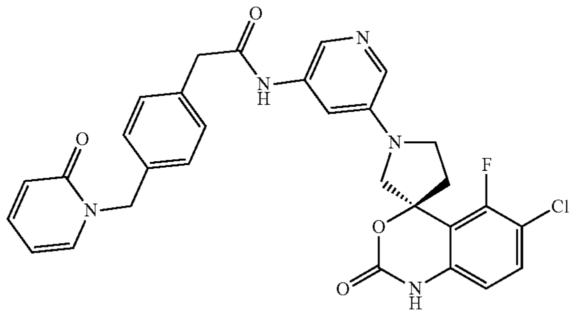 [SMILES: O=C(Cc1ccc(Cn2ccccc2=O)cc1)Nc1cncc(N2CC[C@]3(C2)OC(=O)Nc2ccc(Cl)c(F)c23)c1]

(S)—N-(5-(6-Chloro-5-fluoro-2-oxo-1,2-dihydrospiro[benzo[d][1,3]oxazine-4,3'-pyrrolidin]-1'-yl)pyridin-3-yl)-2-(4-((2-oxopyridin-1(2H)-yl)methyl)phenyl)acetamide DMA (0.2 mL) was added to a mixture of (S)-1'-(5-aminopyridin-3-yl)-6-chloro-5-fluorospiro[benzo[d][1,3]oxazine-4,3'-pyrrolidin]-2(1H)-one (25 mg, 0.072 mmol) and 2-(4-((2-oxopyridin-1(2H)-yl)methyl)phenyl)acetic acid (17 mg, 0.072 mmol). DIEA (50 μL, 0.29 mmol) was added, followed by the addition of HATU (27 mg, 0.072 mmol) in one portion. The resulting mixture was stirred at rt for 2 h, at which time, the reaction was diluted with DMSO and purified by reversed-phase preparatory-HPLC (C18 stationary phase, ACN/water+0.1% TFA) to yield the title compound. $^1$H NMR (400 MHz, $CD_3OD$) δ 10.8 (s, 1H), 10.7 (s, 1H), 8.31 (s, 1H), 7.84 (s, 1H), 7.78-7.76 (m, 1H), 7.59-7.56 (m, 1H), 7.50 (s, 1H), 7.44-7.41 (m, 1H), 7.30-7.24 (m, 4H), 6.82 (d, J=10 Hz, 1H), 6.41 (d, J=10 Hz, 1H), 6.25 (dd, J=10.0 Hz, J=5 Hz, 1H), 5.06 (s, 2H), 3.89 (s, 2H), 3.67 (s, 1H), 2.76-2.69 (m, 1H), 2.64-2.49 (m, 1H). LCMS $[M+H]^+$=574.0 (calcd. 574.2).

Plasma Kallikrein Assay

The effectiveness of a compound of the present invention as an inhibitor of plasma kallikrein can be determined using a relevant purified serine protease, and an appropriate synthetic substrate. The rate of hydrolysis of the chromogenic or fluorogenic substrate by the relevant serine protease was measured both in the absence and presence of compounds of the present invention. Assays were conducted at rt or at 37° C. Hydrolysis of the substrate resulted in release of amino trifluoromethylcoumarin (AFC), which was monitored spectrofluorometrically by measuring the increase in emission at 510 nm with excitation at 405 nm. A decrease in the rate of fluorescence change in the presence of inhibitor is indicative of enzyme inhibition. Such methods are known to one skilled in the art. The results of this assay are expressed as the half-maximal inhibitory concentrations ($IC_{50}$), or the inhibitory constant, $K_i$.

Plasma kallikrein determinations were made in 50 mM HEPES buffer at pH 7.4 containing 150 mM NaCl, 5 mM $CaCl_2$, and 0.1% PEG 8000 (polyethylene glycol; Fisher Scientific). Determinations were made using purified Human plasma kallikrein at a final concentration of 0.5 nM (Enzyme Research Laboratories) and the synthetic substrate, Acetyl-K-P-R-AFC (Sigma #C6608) at a concentration of 100 mM.

Activity assays were performed by diluting a stock solution of substrate at least tenfold to a final concentration≤0.2 Km into a solution containing enzyme or enzyme equilibrated with inhibitor. Times required to achieve equilibration between enzyme and inhibitor were determined in control experiments. The reactions were performed under linear progress curve conditions and fluorescence increase measured at 405 Ex/510 Em nm. Values were converted to percent inhibition of the control reaction (after subtracting 100% Inhibition value). $IC_{50}$ was determined by inflection point from a four parameter logistic curve fit. Ki was calculated using the Cheng Prusoff equation, Ki=$IC_{50}$/(1+[S]/Km)).

The activities shown by this assay indicate that the compounds of the invention may be therapeutically useful for treating or preventing various ophthalmic, cardiovascular and/or cerebrovascular thromboembolic conditions in patients suffering from unstable angina, acute coronary syndrome, refractory angina, myocardial infarction, transient ischemic attacks, atrial fibrillation, stroke such as thrombotic stroke or embolic stroke, venous thrombosis, coronary and cerebral arterial thrombosis, cerebral and pulmonary embolism, atherosclerosis, deep vein thrombosis, disseminated intravascular coagulation, reocclusion or restenosis of recanalized vessels, hereditary angioedema, uveitis, posterior uveitis, wet age-related macular degeneration, diabetic macular edema, diabetic retinopathy and retinal vein occlusion.

Factor XIa Assay

The effectiveness of a compound of the present invention as an inhibitor of Coagulation factor XIa can be determined using a relevant purified serine protease, and an appropriate synthetic substrate. The rate of hydrolysis of the chromogenic or fluorogenic substrate by the relevant serine protease was measured both in the absence and presence of compounds of the present invention. Assays were conducted at rt or at 37° C. Hydrolysis of the substrate resulted in release of amino trifluoromethylcoumarin (AFC), which was monitored spectrofluorometrically by measuring the increase in emission at 510 nm with excitation at 405 nm. A decrease in the rate of fluorescence change in the presence of inhibitor is indicative of enzyme inhibition. Such methods are known to one skilled in the art. The results of this assay are expressed as the half-maximal inhibitory concentrations ($IC_{50}$), or the inhibitory constant, $K_i$.

Compounds were pre-incubated for 30 min at 25° C. with human (0.04 nM) factor XIa in 50 mM HEPES buffer with 150 mM sodium chloride, 5 mM calcium chloride, 0.1% PEG 8000, pH 7.4. factor XIa enzymatic activity was determined by addition of the substrate glycine-proline-arginine-7-amido-4-trifluoromethylcoumarin (GPR-AFC) and measurement of the fluorescence at 400/505 nm after a 60 min incubation at 25° C. The % inhibition for each data point was calculated from the data and analyzed using the log (inhibitor) vs. response four parameters equation to determine the half-maximal inhibitory concentrations ($IC_{50}$). The $IC_{50}$ were converted to equilibrium inhibitory constants (Ki) using the Cheng-Prusoff equation.

The activities shown by this assay indicate that the compounds of the invention may be therapeutically useful for treating or preventing various cardiovascular and/or cerebrovascular thromboembolic conditions in patients suffering from unstable angina, acute coronary syndrome, refractory angina, myocardial infarction, transient ischemic attacks, atrial fibrillation, stroke such as thrombotic stroke or embolic stroke, venous thrombosis, coronary and cerebral arterial thrombosis, cerebral and pulmonary embolism, atherosclerosis, deep vein thrombosis, disseminated intravascular coagulation, and reocclusion or restenosis of recanalized vessels.

Plasma Kallikrein (PKal) $IC_{50}$ (nM) and Factor XIa (FXIa) $IC_{50}$ (nM) for selected compounds are as follows:

| Example | PKal $IC_{50}$ (nM) | FXIa $IC_{50}$ (nM) |
|---|---|---|
| 1 | 19.3 | 10000 |
| 2 | 6.8 | 10000 |
| 3 | 9.5 | 10000 |
| 4 | 1.2 | 7439 |
| 5 | 3.0 | 5654 |
| 6 | 4.0 | 10000 |
| 7 | 33.5 | 10000 |
| 8 | 30.4 | 10000 |
| 9 | 7.5 | 10000 |
| 10 | 2.5 | 10000 |
| 11 | 3.9 | 10000 |
| 12 | 39.6 | 10000 |
| 13 | 81.6 | 10000 |
| 14 | 1.6 | 10000 |
| 15 | 0.6 | 10000 |
| 16 | 50.0 | 10000 |
| 17 | 16.3 | 10000 |
| 18 | 12.8 | 10000 |
| 19 | 25.6 | 10000 |
| 20 | 1.3 | 10000 |
| 21 | 2.3 | 10000 |
| 22 | 4.7 | 10000 |
| 23 | 0.5 | 10000 |
| 24 | 13.6 | 10000 |
| 25 | 16.5 | 10000 |
| 26 | 3.1 | 10000 |
| 27 | 14.3 | 10000 |
| 28 | 1.9 | 10000 |
| 29 | 5.0 | 10000 |
| 30 | 20.9 | 10000 |
| 31 | 8.6 | 10000 |
| 32 | 19.0 | 10000 |
| 33 | 25.4 | 10000 |
| 34 | 5.4 | 10000 |
| 35 | 28.4 | 10000 |
| 36 | 43.7 | 10000 |
| 37 | 44.4 | 10000 |
| 38 | 35.8 | 10000 |
| 39 | 25.8 | 10000 |
| 40 | 18.6 | 10000 |
| 41 | 35.4 | 10000 |
| 42 | 11.8 | 10000 |
| 43 | 1.7 | 10000 |
| 44 | 58.3 | 7664 |
| 45 | 15.8 | 10000 |
| 46 | 38.0 | 10000 |
| 47 | 13.8 | 10000 |
| 48 | 5.9 | 10000 |
| 49 | 8.9 | 10000 |
| 50 | 26.6 | 10000 |
| 51 | 45.9 | 10000 |
| 52 | 19.0 | 10000 |

What is claimed is:

1. A compound of the Formula I:

I

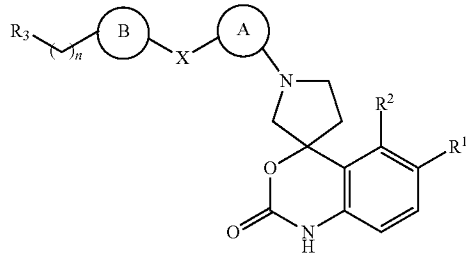

wherein X is $-CH_2-$, $-NH(C{=}O)CH_2-$ or $-(C{=}O)NHCH_2-$;

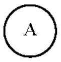 is 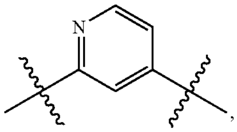,

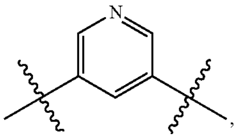, 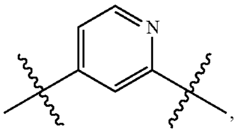,

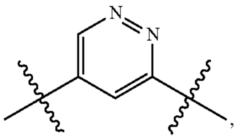, 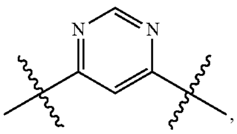,

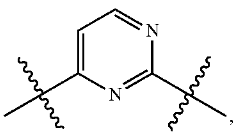, 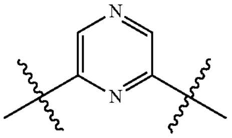 or

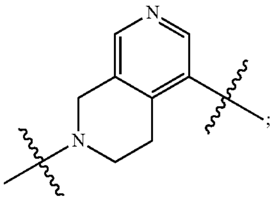;

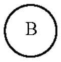

is phenyl or heteroaryl, which can be monocyclic or bicyclic, wherein said phenyl is optionally substituted with halo and said heteroaryl is optionally substituted with halo, hydroxy, $C_{1-6}$ alkyl or oxo;

$R^1$ is selected from the group consisting of hydrogen, halo, hydroxy and $C_{1-6}$ alkyl;

$R^2$ is selected from the group consisting of hydrogen, halo, hydroxy and $C_{1-6}$ alkyl;

$R^3$ is selected from the group consisting of hydrogen, heterocyclyl, which can be monocyclic or bicyclic, heteroaryl and $NR^4R^5$, wherein said heteroaryl is optionally substituted with one or two substituents independently selected from the group consisting of oxo and $C_{1-6}$ alkyl and said heterocyclyl is optionally substituted with one to three substituents independently selected from the group consisting of halo, hydroxy, cyano and $R^x$;

$R^4$ is selected from the group consisting of hydrogen, cyclopropyl and $C_{1-6}$ alkyl;

$R^5$ is selected from the group consisting of hydrogen and $C_{1-6}$ alkyl, which is optionally substituted with one to three substituents selected from the group consisting of halo, hydroxy and cyano;

$R^x$ is hydrogen or $C_{1-6}$ alkyl, which is optionally substituted with one to three substituents selected from the group consisting of halo, hydroxy and methoxy;

n is an integer from zero to two;

or a pharmaceutically acceptable salt thereof.

2. The compound of claim 1 wherein X is —(C═O)NHCH$_2$—, or a pharmaceutically acceptable salt thereof.

3. The compound of claim 1 of the Formula Ia:

Ib

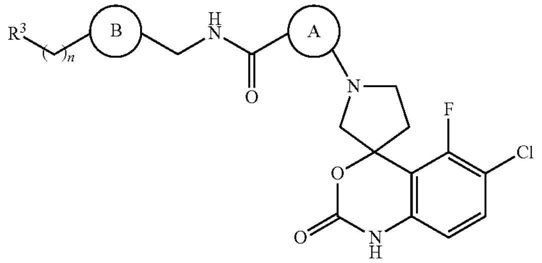

wherein 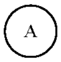 is 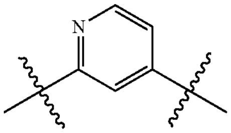,

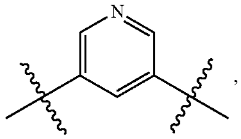, 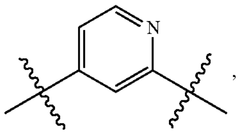,

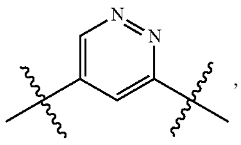, 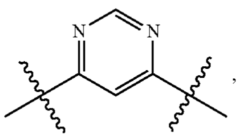,

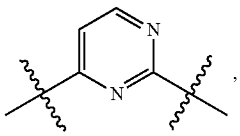, 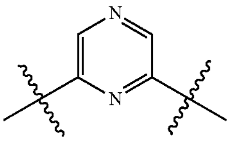 or

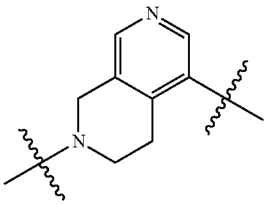;

-continued

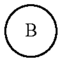 is 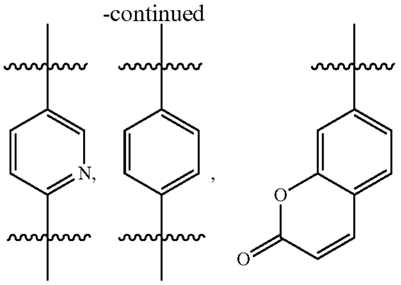

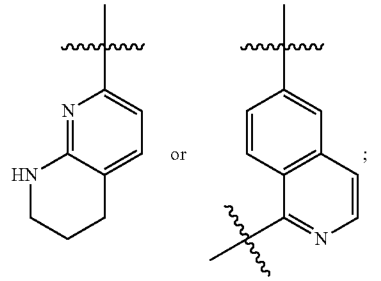;

$R^1$ is selected from the group consisting of hydrogen, halo, hydroxy and $C_{1-6}$ alkyl;

$R^2$ is selected from the group consisting of hydrogen, halo, hydroxy and $C_{1-6}$ alkyl;

$R^3$ is selected from the group consisting of hydrogen, heterocyclyl, which can be monocyclic or bicyclic, heteroaryl and $NR^4R^5$, wherein said heteroaryl is optionally substituted with one or two substituents independently selected from the group consisting of oxo and $C_{1-6}$ alkyl and said heterocyclyl is optionally substituted with one to three substituents independently selected from the group consisting of halo, hydroxy, cyano and $R^x$;

$R^4$ is selected from the group consisting of hydrogen, cyclopropyl and $C_{1-6}$ alkyl;

$R^5$ is selected from the group consisting of hydrogen and $C_{1-6}$ alkyl, which is optionally substituted with one to three substituents selected from the group consisting of halo, hydroxy and cyano;

$R^x$ is hydrogen or $C_{1-6}$ alkyl, which is optionally substituted with one to three substituents selected from the group consisting of halo, hydroxy and methoxy;

n is an integer from zero to two;

or a pharmaceutically acceptable salt thereof.

4. The compound of claim 1 of the Formula 1b:

Ib

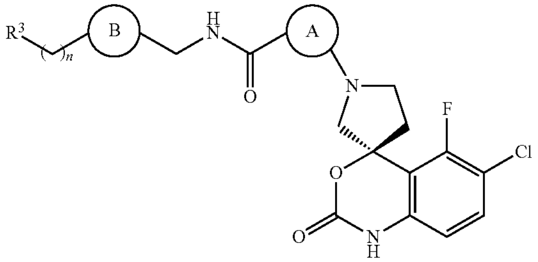

wherein 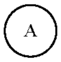 is 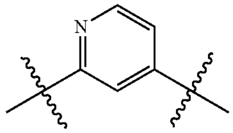,

-continued

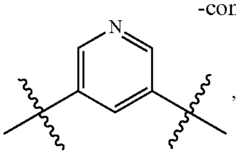,
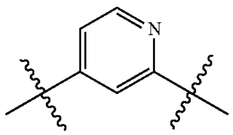,
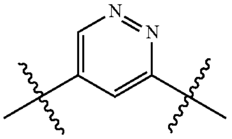,
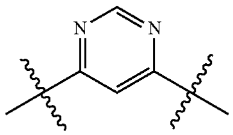,
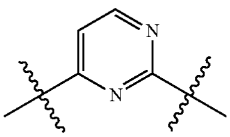,
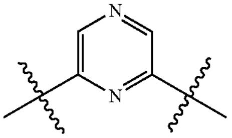 or
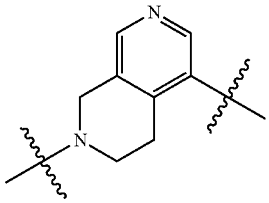;

B is 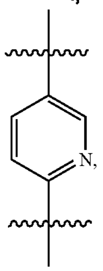, 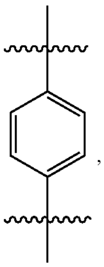, 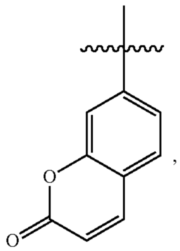, 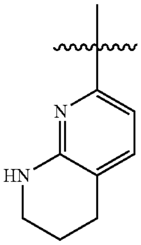 or 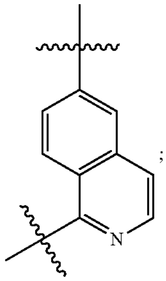;

$R^3$ is selected from the group consisting of hydrogen, heterocyclyl, which can be monocyclic or bicyclic, heteroaryl and $NR^4R^5$, wherein said heteroaryl is optionally substituted with one or two substituents independently selected from the group consisting of oxo and $C_{1-6}$ alkyl and said heterocyclyl is optionally substituted with one to three substituents independently selected from the group consisting of halo, hydroxy, cyano and $R^x$;

$R^4$ is selected from the group consisting of hydrogen, cyclopropyl and $C_{1-6}$ alkyl;

$R^5$ is selected from the group consisting of hydrogen and $C_{1-6}$ alkyl, which is optionally substituted with one to three substituents selected from the group consisting of halo, hydroxy and cyano;

$R^x$ is hydrogen or $C_{1-6}$ alkyl, which is optionally substituted with one to three substituents selected from the group consisting of halo, hydroxy and methoxy;

n is an integer from zero to two;

or a pharmaceutically acceptable salt thereof.

5. The compound of claim 1 wherein $R^1$ is halo and $R^2$ is halo, or a pharmaceutically acceptable salt thereof.

6. The compound of claim 1 wherein n is zero, and $R^3$ is heterocyclyl, which is optionally substituted with one to three halo, or $R^x$, or a pharmaceutically acceptable salt thereof.

7. The compound of claim 1 wherein n is one, and $R^3$ is heteroaryl, which is optionally substituted with methyl or oxo, or a pharmaceutically acceptable salt thereof.

8. The compound of claim 1 wherein $R^4$ is hydrogen, cyclopropyl or methyl, and $R^5$ is $C_{1-6}$ alkyl, which is optionally substituted with one to three halo, or cyano, or a pharmaceutically acceptable salt thereof.

9. The compound of claim 1 selected from:

(S)-6-(6-Chloro-5-fluoro-2-oxo-1,2-dihydrospiro[benzo[d][1,3]oxazine-4,3'-pyrrolidin]-1'-yl)-N-((6-((S-3-methylpyrrolidin-1-yl)pyridin-3-yl)methyl)pyrazine-2-carboxamide, (S)-6-(6-Chloro-5-fluoro-2-oxo-1,2-dihydrospiro[benzo[d][,3]oxazine-4,3'-pyrrolidin]-1'-yl)-N-(6-(pyrrolidin-1-yl)pyridin-3-yl)methyl)pyrazine-2-carboxamide, (S)-5-(6-Chloro-5-fluoro-2-oxo-1,2-dihydrospiro[benzo[d[1,3]oxazine-4,3'-pyrrolidin]-1'-yl)-N-((6-((S)-3-methylpyrrolidin-1-yl)pyridin-3-yl)methyl)nicotinamide, (S)-6-(6-Chloro-5-fluoro-2-oxo-1,2-dihydrospiro[benzo[d][1,3]oxazine-4,3'-pyrrolidin]-1'-yl)-N-((6-((S)-3-methylpyrrolidin-1-yl)pyridin-3-yl)methyl)pyridazine-4-carboxamide, (S)-6-(6-Chloro-5-fluoro-2-oxo-1,2-dihydrospiro[benzo[d][1,3]oxazine-4,3'-pyrrolidin]-1'-yl)-N-((6-((S)-3-fluoropyrrolidin-1-ylpyridin-3-yl)methyl)pyridazine-4-carboxamide, (S)-6-(6-Chloro-5-fluoro-2-oxo-1,2-dihydrospiro[benzo[d][1,3]oxazine-4,3'-pyrrolidin]-1'-yl)-N-6-((S)-3-difluoropyrrolidin-1-yl)pyridin-3-yl)methyl)pyridazine-4-carboxamide, (S)-6-(6-Chloro-5-fluoro-2-oxo-1,2-dihydrospiro[benzo[d][1,3]oxazine-4,3'-pyrrolidin]-1'-yl)-N-(4-(3,3-difluoropyrrolidin-1-yl)-3-fluorobenzyl)pyridazine-4-carboxamide, (S)-6-(6-Chloro-5-fluoro-2-oxo-1,2-dihydrospiro[benzo[d][1,3]oxazine-4,3'-pyrrolidin]-1'-yl)-N-(4-(3,3-difluoropyrrolidin-1-yl-2-fluorobenzyl)pyridazine-4-carboxamide, (S)-6-(6-Chloro-5-fluoro-2-oxo-1,2-dihydrospiro[benzo[d][1,3]oxazine-4,3'-pyrrolidin]-1'-yl)-N-((6-3-(trifluoromethyl)pyrrolidin-1-yl)pyridin-3-yl)methyl)pyridazine-4-carboxamide, (S)-6-(6-Chloro-5-fluoro-2-oxo-1,2-dihydrospiro[benzo[d][1,3]oxazine-4,3'-pyrrolidin]-1'-yl)-N-(4-(1-methylpyrrolidin-2-yl)benzyl)pyridazine-4-carboxamide, (S)-6-(6-Chloro-5-fluoro-2-oxo-1,2-dihydrospiro[benzo[d][1,3]oxazine-4,3'-pyrrolidin]-1'-yl)-N-((6-(1-(methylpyrrolidin-2-yl)pyridin-3-yl)methyl)pyridazine-4-carboxamide, (S)-6-(6-Chloro-5-fluoro-2-oxo-1,2-dihydrospiro[benzo[d][1,3]oxazine-4,3'-pyrrolidin]-1'-yl)-N-(4-(4,4-difluoro-1-methylpyrrolidin-2-yl)benzyl)pyridazine-4-carboxamide, (S)-6-(6-Chloro-5-fluoro-2-oxo-1,2-dihydrospiro[benzo[d][1,3]oxazine-4,3'-pyrrolidin]-1'-yl)-N-((6-(4,4-difluoro-1-methylpyrrolidin-2-ylpyridin-3-yl)methyl)pyridazine-4-carboxamide, (S)-6-(6-Chloro-5-fluoro-2-oxo-1,2-dihydrospiro[benzo[d][1,3]oxazine-4,3'-pyrrolidin]-1'-yl)-N-((6-((2-oxopyridin-1(2H)-yl)methyl)pyridin-3-yl)methyl)pyrazine-2-carboxamide, (S)-5-(6-Chloro-5-fluoro-2-oxo-1,2-dihydrospiro[benzo[d][1,3]oxazine-4,3'-pyrrolidin]-1'-yl)-N-((6-((2-oxopyridin-1(2H)-yl)methyl)pyridin-3-yl)methyl)nicotinamide, (S)-2-(6-Chloro-5-fluoro-2-oxo-1,2-dihydrospiro[benzo[d][1,3]oxazine-4,3'-pyrrolidin]-1'-yl)-N-(4-((2-oxopyridin-1(21)-yl)methyl)benzyl)isonicotinamide, (S)-6-(6-Chloro-5-fluoro-2-oxo-1,2-dihydrospiro[benzo[d][1,3]oxazine-4,3'-pyrrolidin]-1'-yl)-N-(4-((2-oxopyridin-1(2H)-yl)methyl)benzyl)pyridazine-4-carboxamide, (S)-6-(6-Chloro-5-fluoro-2-oxo-1,2-dihydrospiro[benzo[d][1,3]oxazine-4,3'-pyrrolidin]-1'-yl)-N-(4-((4-methyl-1H-pyrazol-1-yl)methyl)benzyl)pyrazine-2-carboxamide, (S)-6-(6-Chloro-5-fluoro-2-oxo-1,2-dihydrospiro[benzo[d][1,3]oxazine-4,3'-pyrrolidin]-1'-yl)-N-(4-((4-methyl-1H-pyrazol-1-yl)methyl)benzyl)pyrimidine-4-carboxamide, (S)-5-(6-Chloro-5-fluoro-2-oxo-1,2-dihydrospiro[benzo[d][1,3]oxazine-4,3'-pyrrolidin]-1'-yl)-N-((6-((4-methyl-1H-pyrazol-1-yl)methyl)pyridin-3-yl)methyl)nicotinamide, (S)-6-(6-Chloro-5-fluoro-2-oxo-1,2-dihydrospiro[benzo[d][1,3]oxazine-4,3'-pyrrolidin]-1'-yl)-N-((6-((4-methyl-1H-pyrazol-1-yl)methyl)pyridin-3-yl)methyl)pyrazine-2-carboxamide, (S)-2-(6-Chloro-5-fluoro-2-oxo-1,2-dihydrospiro[benzo[d][1,3]oxazine-4,3'-pyrrolidin]-1'-yl)-N-(4-((4-methyl-1H-pyrazol-1-yl)methyl)benzyl)isonicotinamide, (S)-6-(6-Chloro-5-fluoro-2-oxo-1,2-dihydrospiro[benzo[d][1,3]oxazine-4,3'-pyrrolidin]-1'-yl)-N-(4-((4-methyl-1H-pyrazol-1-yl)methyl)benzyl)pyridazine-4-carboxamide, (S)-2-(6-Chloro-5-fluoro-2-oxo-1,2-dihydrospiro[benzo[d][1,3]oxazine-4,3'-pyrrolidin]-1'-yl)-N-(4-((4-methyl-1H-pyrazol-1-yl)methyl)benzyl)pyrimidine-4-carboxamide, (S)-4-(6-Chloro-5-fluoro-2-oxo-1,2-dihydrospiro[benzo[d][1,3]oxazine-4,3'-pyrrolidin]-1'-yl)-N-(4-((4-methyl-1H-pyrazol-1-yl)methyl)benzil)picolinamide, (S)-5-(6-Chloro-5-fluoro-2-oxo-1,2-dihydrospiro[benzo[d][1,3]oxazine-4,3'-pyrrolidin]-1'-yl)-N-(4-((4-methyl-1H-pyrazol-1-yl)methyl)benzyl)nicotinamide, (S)-6-(6-Chloro-5-fluoro-2-oxo-1,2-dihydrospiro[benzo[d][1,3]oxazine-4,3'-pyrrolidin]-1'-yl)-N-((6-(3-(methoxymethyl)azetidin-1-yl)pyridin-3-yl)methyl)pyridazine-4-carboxamide, (S)-6-(6-Chloro-5-fluoro-2-oxo-1,2-dihydrospiro[benzo[d][1,3]oxazine-4,3'-pyrolidin]-1'-yl) N-((6-(4-methylpiperazin-1-yl)pyridin-3-yl)methyl)pyridazine-4-carboxamide, (S)-6-(6-Chloro-5-fluoro-2-oxo-1,2-dihydrospiro[benzo[d][1,3]oxazine-4,3'-pyrrolidin]-1'-yl)-N-((6-morpholinopyridin-3-yl)methyl)pyridazine-4-carboxamide, (S)-6-(6-Chloro-5-fluoro-2-oxo-1,2-dihydrospiro[benzo[d][1,3]oxazine-4,3'-pyrrolidin]-1'-yl)-N-((2-oxo-2H-chromen-7-yl)methyl)pyrazine-2-carboxamide, (S)-6-(6-Chloro-5-fluoro-2-oxo-1,2-dihydrospiro[benzo[d][1,3]oxazine-4,3'-pyrrolidin]-1'-yl)-N-((5,6,7,8-tetrahydro-1,8-naphthyridin-2-yl)methyl)pyrazine-2-carboxamide, (S)—N-((1-Aminoisoquinolin-6-yl)methyl)-6-(6-chloro-5-fluoro-2-oxo-1,2-dihydrospiro[benzo[d][1,3]oxazine-4,3'-pyrrolidin]-1'-yl)pyrazine-2-carboxamide, (S)-6-(6-Chloro-5-fluoro-2-oxo-1,2-dihydrospiro[benzo[d][1,3]oxazine-4,3'-pyrrolidin]-1'-yl)-N-((6-(3-fluoroazetidin-1-yl)pyridin-3-yl)methyl)pyrazine-2-carboxamide, (S)-6-(6-Chloro-5-fluoro-2-oxo-1,2-dihydrospiro[benzo[d][1,3]oxazine-4,3'-pyrrolidin]-1'-yl)-N-((6-(3-(methoxymethylazetidin-1-yl)pyridin-3-yl)methyl)pyrazine-2-carboxamide, (S)-6-(6-chloro-5-fluoro-2-oxo-1,2-dihydrospiro[benzo[d][1,3]oxazine-4,3'-pyrrolidin]-1'-yl)-N-((6-(3-hydroxy-3-methylazetidin-1-yl)pyridin-3-yl)methyl)pyrazine-2-carboxamide, (S)-6-(6-Chloro-5-fluoro-2-oxo-1,2-dihydrospiro[benzo[d][1,3]oxazine-4,3'-pyrrolidin]-1'-yl)-N-((6-(3-hydroxy-3-(trifluoromethyl)azetidin-1-yl)pyridin-3-yl)methyl)pyrazine-2-carboxamide, (S)—N-((6-(Azetidin-1-yl)pyridin-3-yl)methyl)-6-(6-chloro-5-fluoro-2-oxo-1,2dihydrospiro[benzo[d][1,3]oxazine-4,3'-pyrrolidin]-1'-yl)pyrazine-2-carboxamide, (S)-6-(6-Chloro-5-fluoro-2-oxo-1,2-dihydrospiro[benzo[d][1,3]oxazine-4,3'-pyrolidin]-1'-yl)-N-(6-((S)-3-fluoropyrrolidin-1-yl)pyridin-3-yl)methyl)pyrazine-2-carboxamide, (S)-6-(6-Chloro-5-fluoro-2-oxo-1,2-dihydrospiro[benzo[d][1,3]oxazine-4,3'-pyrrolidin]-1'-yl)-N-((6-(R)-3-fluoropyrrolidin-1-yl)pyridin-3-yl)methyl)pyrazine-2-carboxamide, N-((6-(3-Azabicyclo[3.1.0]hexan-3-yl)pyridin-3-yl)methyl)-6-(S)-6-chloro-5-fluoro-2-oxo-1,2-dihydrospiro[benzo[d][1,3]oxazine-4,3'-pyrrolidin]-1'-yl)pyrazine-2-carboxamide, (S)-6-(6-Chloro-5-fluoro-2-oxo-1,2-dihydrospiro[benzo[d][1,3]oxazine-4,3'-pyrrolidin]-1'-yl)-N-((6-(piperidin-1-yl)pyridin-3-yl)methylpyrazine-2-carboxamide, (S)-6-(6-Chloro-5-fluoro-2-oxo-1,2-dihydrospiro[benzo[d][1,3]oxazine-4,3'-pyrrolidin]-1'-yl)-N-((6-morpholinopyridin-3-yl)methyl)pyrazine-2-carboxamide, (S)-6-(6-Chloro-5-fluoro-2-oxo-1,2-dihydrospiro[benzo[d][1,3]oxazine-4,3'-pyrrolidin]-1'-yl-N-((6-(4-methylpiperazin-1-yl)pyridin-3-yl)methyl)pyrazine-2carboxamide, (S)-6-(6-Chloro-5-fluoro-2-oxo-1,2-dihydrospiro[benzo[d][1,3]oxazine-4,3'-pyrrolidin]-1'-yl)-N-(4-(((1,1-difluoropropyl)amino)methyl)benzyl)pyridazine-4-carboxamide, N-(4-((sec-Butylamino)methyl)benzyl)-6-((S)-6-chloro-S-fluoro-2-oxo-1,2-dihydrospiro[benzo[d][1,3]oxazine-4,3'-pyrrolidin]-1'-yl)pyridazine-4-carboxamide, (S)-6-(6-Chloro-5-fluoro-2-oxo-1,2-dihydrospiro[benzo[d][1,3]oxazine-4,3'-pyrrolidin]-1'-yl)-N-(4-(((1,1,1-trifluorobutan-2-yl)amino)methyl)benzyl)pyridazine-4-carboxamide, (S)-6-(6-chloro-5-fluoro-2-oxo-1,2-dihydrospiro[benzo[d][1,3]oxazine-4,3'-pyrrolidin]-1'-yl)-N-(4-((3-fluoroazetidin-1-yl)methyl)benzyl)pyridazine-4-carboxamide, (S)-6-(6-Chloro-5-fluoro-2-oxo-1,2-dihydrospiro[benzo[d][1,3]oxazine-4,3'-pyrrolidin]-1'-yl)-N-(4-((isopropyl(methyl)amino)methyl)benzyl)pyridazine-4-carboxamide, (S)-6-(6-Chloro-5-fluoro-2-oxo-1,2-dihydrospiro[benzo[d][1,3]oxazine-4,3'-pyrrolidin]-1'-yl)-N-(4-(((2-cyanoethyl)(cyclopropyl)amino)methylbenzyl)pyridazine-4-carboxamide, (S)-6-(6-Chloro-5-fluoro-2-oxo-1,2-dihydrospiro[benzo[d][1,3]oxazine-4,3'-pyrrolidin]-1'-yl-N-(4-((3-cyano-3-fluoroazetidin-1-yl)methyl)benzyl)pyridazine-4-carboxamide, (S)-6-(Chloro-5-fluoro-1'-(7-(4-((2-oxopyridin-1(2H)-yl)methyl)benzyl)-5,6,7,8-tetrahydro-2,7-naphthyridin-4-yl)spiro[benzo[d][1,3]oxazine-4,3'-pyrrolidin]-2(1H)-one, and (S)—N-(5-(6-Chloro-5-fluoro-2-oxo-1,2-dihydrospiro[benzo[d][1,3]oxazine-4,3'-pyrrolidin]-1'-yl)pyridin-3-yl)-2-(4-((2-oxopyridin-(2H)-yl)methyl)phenyl)acetamide, or a pharmaceutically acceptable salt thereof.

10. A pharmaceutical composition comprising a compound of claim 1 or a pharmaceutically acceptable salt thereof and a pharmaceutically acceptable carrier.

11. A method for treating diabetic retinopathy or hereditary angioedema comprising administering a composition of claim 10 to a mammal in need of thereof.

12. The composition of claim 10 further comprising another agent selected from the group consisting of anti-inflammatory agents, anti-VEGF agents, immunosuppressive agents, anticoagulants, antiplatelet agents, and thrombolytic agents.

13. The method of claim 11 further comprising another agent selected from the group consisting of anti-inflammatory agents, anti-VEGF agents, immunosuppressive agents, anticoagulants, antiplatelet agents, and thrombolytic agents.

* * * * *